US009333251B2

(12) United States Patent
Kopecko et al.

(10) Patent No.: US 9,333,251 B2
(45) Date of Patent: May 10, 2016

(54) **VACCINE FOR PROTECTION AGAINST *SHIGELLA SONNEI* DISEASE**

(71) Applicant: The United States of America, as represented by the Secretary, Dept. of Health and Human Services, Washington, DC (US)

(72) Inventors: Dennis J. Kopecko, Silver Spring, MD (US); De-Qi Xu, Columbia, MD (US); John O. Cisar, Gaithersburg, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/660,498

(22) Filed: Mar. 17, 2015

(65) Prior Publication Data

US 2015/0182611 A1 Jul. 2, 2015

Related U.S. Application Data

(60) Continuation of application No. 13/686,299, filed on Nov. 27, 2012, now Pat. No. 8,992,943, which is a continuation of application No. 13/295,811, filed on Nov. 14, 2011, now Pat. No. 8,337,832, which is a division of application No. 12/474,223, filed on May 28, 2009, now Pat. No. 8,071,084, which is a continuation of application No. 10/346,706, filed on Jan. 15, 2003, now Pat. No. 7,541,043.

(60) Provisional application No. 60/349,788, filed on Jan. 16, 2002.

(51) Int. Cl.
*A61K 39/112* (2006.01)
*C12N 1/36* (2006.01)
*A61K 39/00* (2006.01)

(52) U.S. Cl.
CPC .............. *A61K 39/0283* (2013.01); *C12N 1/36* (2013.01); *A61K 2039/522* (2013.01)

(58) Field of Classification Search
None
See application file for complete search history.

(56) References Cited

U.S. PATENT DOCUMENTS

| | | | |
|---|---|---|---|
| 4,632,830 | A | 12/1986 | Formal et al. |
| 5,672,345 | A | 9/1997 | Curtiss, III |
| 5,980,907 | A | 11/1999 | Dougan et al. |
| 6,190,669 | B1 | 2/2001 | Noriega et al. |

OTHER PUBLICATIONS

Bélanger, Myriam et al., "Functional analysis of genes responsible for the synthesis of the B-band O antigen of *Pseudomonas aeruginosa* serotype O6 lipopolysaccharide," Microbiology, 1999, vol. 145, pp. 3505-3521.

Bilge, Sima S. et al., "Role of the *Escherichia coli* O157:H7 O Side Chain in Adherence and Analysis of an *rfb* Locus," Infection and Immunity, 1996, vol. 64, pp. 4795-4801.

Black, Robert E. et al., "Prevention of Shigellosis by a *Salmonella typhi-Shigella sonnei* Bivalent Vaccine," The Journal of Infectious Diseases, 1987, vol. 155, pp. 1260-1265.

Bowie, James U. et al., "Deciphering the Message in Protein Sequences: Tolerance to amino Acid Substitutions," Science, 1990, vol. 247, pp. 1306-1310.

Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 1990, vol. 111, pp. 2129-2138.

Burrows, Lori L. et al., "Functional Conservation of the Polysaccharide Biosynthetic Protein WbpM and Its Homologues in *Pseudomonas aeruginosa* and Other Medically Significant Bacteria," Infection and Immunity, 2000, vol. 68, pp. 931-936.

Chida, Toshio et al., "The Complete DNA Sequence of the O Antigen Gene Region of *Plesiomonas shigelloides* Serotype O17 Which Is Identical to *Shigella sonnei* Form 1 Antigen," Microbiology and Immunology, 2000, vol. 44, pp. 161-172.

Creuzenet, Carole et al., "F1aA1, a New Bifunctional UDP-GlcNAc $C_6$ Dehydratase/$C_4$ Reductase from *Helicobacter pylori*," The Journal of Biological Chemistry, 2000, vol. 275, pp. 34873-34880.

DuPont, Herbert et al., "Immunity in Shigellosis. I. Response of Man to Attenuated Strains of *Shigella*," The Journal of Infectious Diseases, 1972, vol. 125, pp. 5-11.

Ertesvåg, Helga et al., "Cloning and Expression of an *Azotobacter vinelandii* Mannuronan C-5-Epimerase Gene," Journal of Bacteriology, 1994, vol. 176, pp. 2846-2853.

Formal, B. et al., "Construction of a Potential Bivalent Vaccine Strain: Introduction of *Shigella sonnei* Form I Antigen Genes into the *galE Salmonella typhi* Ty2la Typhoid Vaccine Strain," Infection and Immunity, 1981, vol. 34, pp. 746-750.

Franklin, Michael J. et al., "*Pseudomonas aeruginosa* AlgG Is a Polymer Level Alginate C5-Mannuronan Epimerase," Journal of Bacteriology, 1994, vol. 176, pp. 1821-1830.

Galán, Jorge E. et al., "Cloning and characterization of the *asd* gene of *Salmonella typhimurium*: use in stable maintenance of recombinant plasmids in *Salmonella* vaccine strains," Gene, 1990, vol. 94, pp. 29-35.

Germanier, R. and Fürer, E., "Isolation and Characterization of *Gal* E Mutant Ty 21a of *Salmonella typhi*: A Candidate Strain for a Live, Oral Typhoid Vaccine," The Journal of Infectious Diseases, 1975, vol. 131, pp. 553-558.

(Continued)

*Primary Examiner* — Brian J Gangle
(74) *Attorney, Agent, or Firm* — Swanson & Bratschun, L.L.C.

(57) ABSTRACT

Compositions and methods for protecting a susceptible host against an infection of *Shigella sonnei* are disclosed. Such compositions and methods are useful for protecting the host against bacillary dysentery and shigellosis.

3 Claims, 5 Drawing Sheets

(56) References Cited

OTHER PUBLICATIONS

Gotschlich, Emil C., "Genetic Locus for the Biosynthesis of the Variable Portion of *Neisseria gonorrhoeae* Lipooligosaccharide," The Journal of Experimental Medicine, 1994, vol. 180, pp. 2181-2190.

Hartman, Antoinette B. and Venkatesan, Malabi M., "Construction of a Stable Attenuated *Shigella sonnei* Δ*virG* Vaccine Strain, WRSS1, and Protective Efficacy and Immunogenicity in the Guinea Pig Keratoconjunctivitis Model," Infection and Immunity, 1998, vol. 66, pp. 4572-4576.

Hartman, Antoinette B. et al., "Molecular Analysis of Variant Plasmid Forms of a Bivalent *Salmonella typhi-Shigella sonnei* Vaccine Strain," Journal of Clinical Microbiology, 1991, vol. 29, pp. 27-32.

Hashimoto, Yasuhiro et al., "Complete Nucleotide Sequence and Molecular Characterization of ViaB Region Encoding Vi Antigen in *Salmonella typhi*," Journal of Bacteriology, 1993, vol. 175, pp. 4456-4465.

Heinrichs, David E. et al., "The Assembly System for the Lipopolysaccharide R2 Core-type of *Escherichia coli* Is a Hybrid of Those Found in *Escherichia coli* K-12 and *Salmonella enterica*," The Journal of Biological Chemistry, 1998, vol. 273, pp. 8849-8859.

Herrington, Deirdre A. et al., "Studies in volunteers to evaluate candidate *Shigella* vaccines: further experience with a bivalent *Salmonella typhi-Shigella sonnei* vaccine and protection conferred by previous *Shigella sonnei* Disease," Vaccine, 1990, vol. 8, pp. 353-357.

Kenne, Lennart et al., "Structural Studies of the O-Specific Side-chains of the *Shigella sonnei* Phase I Lipopolysaccharide," 1980, vol. 78, pp. 119-126.

Keren, David F. et al., "Intestinal Immunoglobulin A Responses in Rabbits to a *Salmonella typhi* Strain Harboring a *Shigella sonnei* Plasmid," Infection and Immunity, 1982, vol. 37, pp. 387-389.

Kopecko, Dennis J. et al., "Genetic and Physical Evidence for Plasmid Control of *Shigella sonnei* Form I Cell Surface Antigen," Infection and Immunity, 1980, vol. 29, pp. 207-214.

Lazar Eliane et al., "Transforming Growth Factor α: Mutation of Aspartic Acid 47 and Leucine 48 Results in Different Biological Activities," Molecular and Cellular Biology, 1988, vol. 8, pp. 1247-1252.

Li, Jin-ping et al., "Biosynthesis of Heparin/Heparan Sulfate: cDNA cloning and expression of $_D$-glucuronyl C5-Epimerase from Bovine Lung," The Journal of Biological Chemistry, 1997, vol. 272, pp. 28158-28163.

Paulsen, Ian T. et al., "A family of Gram-negative bacterial outer membrane factors that function in the export of proteins, carbohydrates, drugs and heavy metals from Gram-negative bacteria," FEMS Microbiology Letters, 1997, vol. 156, pp. 1-8.

Sansonetti, Philippe J. et al., "*Shigella sonnei* Plasmids: Evidence that a Large Plasmid is Necessary for Virulence," Infection and Immunity, 1981, vol. 34, pp. 75-83.

Seid Jr., Robert C. et al., "Unusual Lipopolysaccharide Antigens of a *Salmonella typhi* Oral Vaccine Strain Expressing the *Shigella sonnei* From I Antigen," The Journal of Biological Chemistry, 1984, vol. 259, pp. 9028-9034.

Shepherd, James G. et al., "Comparison of O-Antigen Gene Clusters of *Escherichia coli* (*Shigella*) Sonnei and *Plesiomonas shigelloides* O17: Sonnei Gained its Current Plasmid-Borne O-Antigen Genes from *P. shigelloides* in a Recent Event," Infection and Immunity, 2000, vol. 68, pp. 6056-6061.

Stroeher, Uwe H. et al., "A putative pathway for perosamine biosynthesis is the first function encoded with the *rfb* region of *Vibrio cholerae* O1," Gene, 1995, vol. 166, pp. 33-42.

Van de Verg, Lillian et al., "Specific Immunoglobulin A-Secreting Cells in Peripheral Blood of Humans Following Oral Immunization with a Bivalent *Salmonella typhi-Shigella sonnei* Vaccine or Infection by Pathogenic *S. sonnei*," Infection and Immunity, 1990, vol. 58, pp. 2002-2004.

Viret, Jean-Francois et al., "Molecular cloning and characterization of the genetic determinants that express the complete *Shigella* serotype D (*Shigella sonnei*) lipopolysaccharide in heterologous live attenuated vaccine strains," Molecular Microbiology, 1993, vol. 7, pp. 239-252.

Wang, Lei et al., "Expression of the O antigen gene cluster is regulated by RfaH through the JUMPstart sequence," FEMS Microbiology Letters, 1998, vol. 165, pp. 201-206.

Whitfield, Chris et al., "Structure, Assembly and Regulation of Expression of Capsules in *Escherichia coli*," Molecular Microbiology, 1999, vol. 31, pp. 1307-1319.

Xu, D. et al., "Abstract B-436: Genetic and Functional Studies of the *Shigella sonnei* Rfb/Rfe Gene Cluster," Abstracts of the 101$^{st}$ General Meeting of the American Society for Microbiology, May 2001, p. 138.

Xu et al. (2002) Infect. Immun. 70(8):4414-4423, "Molecular Cloning and Characterization of Genes for *Shigella sonnei* Form I O Polysaccharide: Proposed Biosynthetic Pathway and Stable Expression in a Live *Salmonella* Vaccine Vector."

Yoshida, Yoko et al., "Molecular Cloning and Characterization of Form I Antigen Genes of *Shigella sonnei*," Journal of General Microbiology, 1991, vol. 137, pp. 867-874.

Zhao, Xin et al., "WbpO, a UDP-*N*-acetyl- D-galactosamine Dehydrogenase from *Pseudomonas aeruginosa* Serotype O6," The Journal of Biological Chemistry, 2000, vol. 275, pp. 33252-33259.

U.S. Patent and Trademark Office, Non-final Office Action for U.S. Appl. No. 10/346,706, Sep. 5, 2006, 17 pages.

U.S. Patent and Trademark Office, Non-final Office Action for U.S. Appl. No. 10/346,706, May 31, 2007, 14 pages.

U.S. Patent and Trademark Office, Final Office Action for U.S. Appl. No. 10/346,706, Nov. 19, 2007, 23 pages.

U.S. Patent and Trademark Office, Advisory Action for U.S. Appl. No. 10/346,706, Mar. 21, 2008, 3 pages.

U.S. Patent and Trademark Office, Non-final Office Action for U.S. Appl. No. 10/346,706, Jul. 24, 2008, 13 pages.

Notice of Allowance for U.S. Appl. No. 10/346,706, Jan. 27, 2009, 6 pages.

VACCINE FOR PROTECTION AGAINST *SHIGELLA SONNEI* DISEASE

RELATED APPLICATION DATA

The present application is a continuation of U.S. patent application Ser. No. 13,686,299, filed Nov. 27, 2012, now U.S. Pat. No. 8,992,943, issued Mar. 31, 2015, which is a continuation of U.S. patent application Ser. No. 13/295,811, filed Nov. 14, 2011, now U.S. Pat. No. 8,337,832, issued Dec. 25, 2012; which is a divisional of U.S. patent application Ser. No. 12/474,223, filed May 28, 2009, now U.S. Pat. No. 8,071, 084, issued Dec. 6, 2011; which is a continuation of U.S. patent application Ser. No. 10/346,706, filed Jan. 15, 2003, now U.S. Pat. No. 7,541,043, issued Jun. 2, 2009; which is a nonprovisional of U.S. Provisional Patent Application No. 60/349,788, filed Jan. 16, 2002; all of the foregoing applications are incorporated herein by reference in their entireties.

STATEMENT REGARDING FEDERALLY SPONSORED RESEARCH OR DEVELOPMENT

The instant application was made with government support; the government has certain rights in this invention.

SEQUENCE LISTING

The Sequence Listing text file attached hereto, created Nov. 27, 2012, size 194 kilobytes, and filed herewith as file name "6137FDA1CON11_SEQ_20121127_ST25.txt" is incorporated herein by reference in its entirety.

TECHNICAL FIELD

This invention relates to the field of vaccines for treating and preventing bacillary dysentery. In particular, this invention provides for attenuated live bacteria expressing the *Shigella sonnei* form I-O polysaccharide that are useful for inducing an immunoprotective response against *Shigella sonnei*.

BACKGROUND

Bacillary dysentery and specifically shigellosis is a global human health problem. It has been over 100 years since the discovery of *Shiga's bacillus*, yet shigellosis remains endemic in most areas of the world including industrialized nations. An estimated 200 million people worldwide suffer from shigellosis, with more than 650,000 associated deaths annually (27). A recent CDC estimate indicates the occurrence of over 440,000 20 annual shigellosis cases in the United States alone (32), approximately 80% of which are caused by *Shigella sonnei*. All virulent *S. sonnei* strains comprise a single serotype determined by form I O-polysaccharide (O-Ps). This O-Ps is composed of a disaccharide repeating unit containing two unusual amino sugars, 2-amino-2-deoxy-L-altruronic acid (L-AltNAcA) and 2-acetamido-4-amino-2,4,6-trideoxy-D-galactose (4-n-D-FucNAc) (25). The 25 genes encoding the enzymes that produce this O-Ps are novelly located on the 180 kb virulence plasmid in *S. sonnei* (26), which also harbors the invasion genes (36). Virulent form I colonies are typically unstable and upon replating convert to rough colonies, termed form II, due primarily to spontaneous loss of the large virulence plasmid and the ensuing loss of form I O-antigen. Substantially identical genes that encode the same antigen producing enzymes are located on the bacterial chromosome in *Plesiomonas shigelloides* (termed the O17 gene cluster).

Immunity to Shigellae, acquired either by natural infection or volunteer challenge, is mediated largely by immune responses directed against the serotype specific O-Ps (9, 10). This insight has led to the development of a variety of candidate vaccines containing *Shigella* O-Ps for oral or parenteral administration including recombinant heterologous, live, bacterial carrier strains (3, 12, 18). Parenteral vaccines in the past have not been effective in protecting against bacillary dysentery because shigellosis is an infection limited to the superficial layer of the colonic mucosa. It is, therefore, not surprising that attempts to immunize man or other primates with killed whole cell *Shigella* vaccines, administered by the parenteral route, have not been successful.

In early recombinant vaccine efforts, the virulence plasmid of *S. sonnei* was transferred as part of a larger plasmid cointegrate to the attenuated vector *Salmonella enterica* serovar *Typhi* strain Ty21a (i.e. *S. Typhi* Ty21a) (12). The resulting hybrid vaccine strain, 5076-1C, expressed *S. sonnei* O antigen as a lipid-linked surface O-Ps as well as *S. Typhi* 9,12 LPS (37). Although not core-linked, this form I O-Ps was immunogenic (12) and oral immunization of volunteers with 5076-1C elicited protection against virulent *S. sonnei* oral challenge (3, 21, 40). However, the protection observed in volunteers was variable, presumably due to loss of the form I gene region from the large cointegrate plasmid in 5076-1C (17). Thus, further molecular studies are needed to stabilize the *S. sonnei* form I gene region in vaccine vector constructs. In spite of an increased molecular understanding of *Shigella* pathogenesis, there are still no licensed vaccines for protection against shigellosis in the United States.

Although the form I O-Ps-encoding locus has been studied in some detail previously (6, 24, 38, 42, 45) the biosynthetic pathway and minimal gene region for stable expression of 0-antigen have not been unambiguously defined. We show through deletion and sequence analyses and LPS expression studies that the *S. sonnei* form I biosynthetic gene region comprises a 12.3 kb operon. A detailed biosynthetic pathway, based on DNA sequence analysis of this region and the known structure of form I O-Ps, is proposed. In addition, stable expression of form I O-Ps was observed from a low copy plasmid and was associated with the removal of an adjacent 1591 resulting in small, genetically stable form I gene region constructs. We report the development and animal testing of a live attenuated *S. Typhi* vaccine vector stably expressing enzymes that produce form I O-Ps for protection against *S. sonnei* disease.

To develop a more stable living attenuated oral *Shigella* strain vaccine, the gene region encoding the enzymes that produce form I antigen was isolated from a large non-conjugative plasmid and analyzed to determine the essential genes required for biosynthesis of *Shigella sonnei* form I O-polysaccharide. Nucleic acids totaling 18 kb, were characterized genetically and used to define a minimal region encoding all of the proteins required to produce the form I antigen for development of live vaccine vector strains. Constructs comprising a 12.2 kb region encoding a consensus promoter and ten contiguous ORF's, and additional flanking DNA were generated which contained all of the information required to produce the *Shigella* form I O-Ps antigen. Significantly, attenuated *Salmonella enterica* serovar *Typhi* live vector vaccine candidate strains, containing minimal-sized form I O-Ps operon constructs, elicited immune protection in mice against virulent *S. sonnei* challenge.

SUMMARY

In one aspect of the invention, an immunoprotective composition containing an attenuated bacteria capable of expressing an antigen useful for inducing an immunoprotective response against *Shigella sonnei* (*S. sonnei*) is prepared. The antigen comprises the *S. sonnei* form I O-polysaccharide and the antigen is produced by enzymes encoded by an expression cassette containing a nucleotide fragment comprising the genes wbgT, wbgU, wzx, wzy, wbgV, wbgW, wbgX, wbgY, and wbgZ isolated from the *S. sonnei* rjb/rfc gene cluster or Plesiomonas *shigelloides* (*P. shigelloides*) O17 gene cluster which are operably linked to transcriptional promoter and termination signals. The gene containing fragment is between 10,000 and 13,700 nucleotides in length. The expression cassette containing the fragment does not include sequences that naturally flank the rfb/rfc gene cluster.

In another aspect of the invention, the attenuated bacteria in the immunoprotective composition are selected from the group consisting of *Campylobacter jejuni, Campylobacter coli, Listeria monocytogenes, Yersinia enterocolitica, Yersinia pestis, Yersinia pseudotuberculosis, Escherichia coli, Shigella flexneri, Shigella sonnei, Shigella dysenteriae, Shigella boydii, Helicobacter pylori, Helicobacter felis, Gastrospirillum hominus, Vibrio cholerae, Vibrio parahaemdlyticus, Vibrio vulnificus, Bacteroides fragilis, Clostridium difficile, Salmonella typhimurium, Salmonella typhi, Salmonella gallinarum, Salmonella pullorum, Salmonella choleraesuis, Salmonella enteritidis, Streptococcus gordonii, Lactobacillis* sp., *Klebsiella pneumoniae, Enterobacter cloacae*, and *Enterococcus faecalis*.

In one embodiment of the invention, the attenuated bacteria are *E. coli* bacteria selected from the group consisting of the strains DH5α and HB101. In another embodiment of the invention, the attenuated bacteria are *S. typhi* bacteria selected from the group consisting of the strains Ty21a, CVD 908, CVD 908-htrA, X4073 and Ty800. In a particularly preferred embodiment, the attenuated *S. typhi* bacteria are the attenuated strain of Ty2. In another embodiment, the attenuated bacteria are *S. sonnei* bacteria selected from the group consisting of strains 53GI and 53GII.

In one aspect of the invention, the gene containing fragment in the immunoprotective composition comprises SEQ ID NO:2, SEQ ID NO:3, or SEQ ID NO:4 operably linked to a promoter.

In another aspect of the invention, the gene containing fragment of the immunoprotective composition lacks SEQ ID NO:15.

In still another aspect of the invention the enzymes that produce the antigen are expressed from a recombinant plasmid. In one embodiment of the invention, the recombinant plasmid contains a selectable marker. In a preferred embodiment, the selectable marker is the aspartate β-semialdehyde dehydrogenase (asd) gene operably linked to a promoter. In still another embodiment of the invention, the enzymes that produce the antigen are encoded by a recombinant plasmid containing SEQ ID NO: 2, SEQ ID NO: 3, or SEQ ID NO: 4 operably linked to a promoter. In yet another embodiment of the invention, the recombinant plasmid lacks SEQ ID NO:15. In one embodiment, the recombinant plasmid comprises SEQ ID NO: 2 operably linked to a promoter. In another embodiment, the recombinant plasmid comprises SEQ ID NO: 3 operably linked to a promoter. In still another embodiment, the recombinant plasmid comprises SEQ ID NO: 4 operably linked to a promoter.

In another aspect of the invention, the immunoprotective composition also contains a pharmaceutical diluent.

The invention provides for a method of protecting a susceptible host against an infection of *Shigella sonnei* (*S. sonnei*) by administering to the host an immunoprotective composition containing an attenuated bacteria capable of expressing an antigen useful for inducing an immunoprotective response against *Shigella sonnei* (*S. sonnei*), where the antigen comprises the *S. sonnei* form I O-polysaccharide, the antigen is produced by enzymes encoded by an expression cassette containing a nucleotide fragment comprising the genes wbgT, wbgU, wzx, wzy, wbgV, wbgW, wbgX, wbgY, and wbgZ isolated from the *S. sonnei* rfb/rfc gene cluster or Plesiomonas *shigelloides* (*P. shigelloides*) O17 gene cluster which are operably linked to transcriptional promoter and termination signals, the gene containing fragment is between 10,000 and 13,700 nucleotides in length, the expression cassette containing the fragment does not include sequences that naturally flank the rfb/rfc gene cluster, and the composition is given in an amount sufficient to invoke an immunoprotective response in the host.

In another aspect the invention provides a method of protecting a susceptible host against an infection of *Shigella sonnei* (*S. sonnei*) comprising administering to said host an immunoprotective composition containing an attenuated bacteria capable of expressing an antigen useful for inducing an immunoprotective response against *Shigella sonnei* (*S. sonnei*), where the antigen comprises the *S. sonnei* form I O-polysaccharide, the antigen is produced by enzymes encoded by an expression cassette containing a nucleotide fragment comprising the genes wbgT, wbgU, wzx, wzy, wbgV, wbgW, wbgX, wbgY, and wbgZ isolated from the *S. sonnei* rfb/rfc gene cluster or Plesiomonas *shigelloides* (*P. shigelloides*) O17 gene cluster which are operably linked to transcriptional promoter and termination signals, the gene containing fragment is between 10,000 and 13,700 nucleotides in length, the expression cassette containing the fragment does not include sequences that naturally flank the rfb/rfc gene cluster, the expression cassette is on a recombinant plasmid, and the immunogenic composition is given in an amount sufficient to invoke an immunoprotective response in the host. In one embodiment of the method, the enzymes that produce the antigen are encoded by a recombinant plasmid containing SEQ ID NO: 2, SEQ ID NO: 3, or SEQ ID NO: 4 operably linked to a promoter. In another embodiment of the method, the immunogenic composition is in a pharmaceutically acceptable carrier. In still another embodiment of the method, the immunogenic composition is in a sterile medium. In another embodiment of the method, the immunogenic composition also contains an adjuvant.

DEFINITIONS

Figure 1:
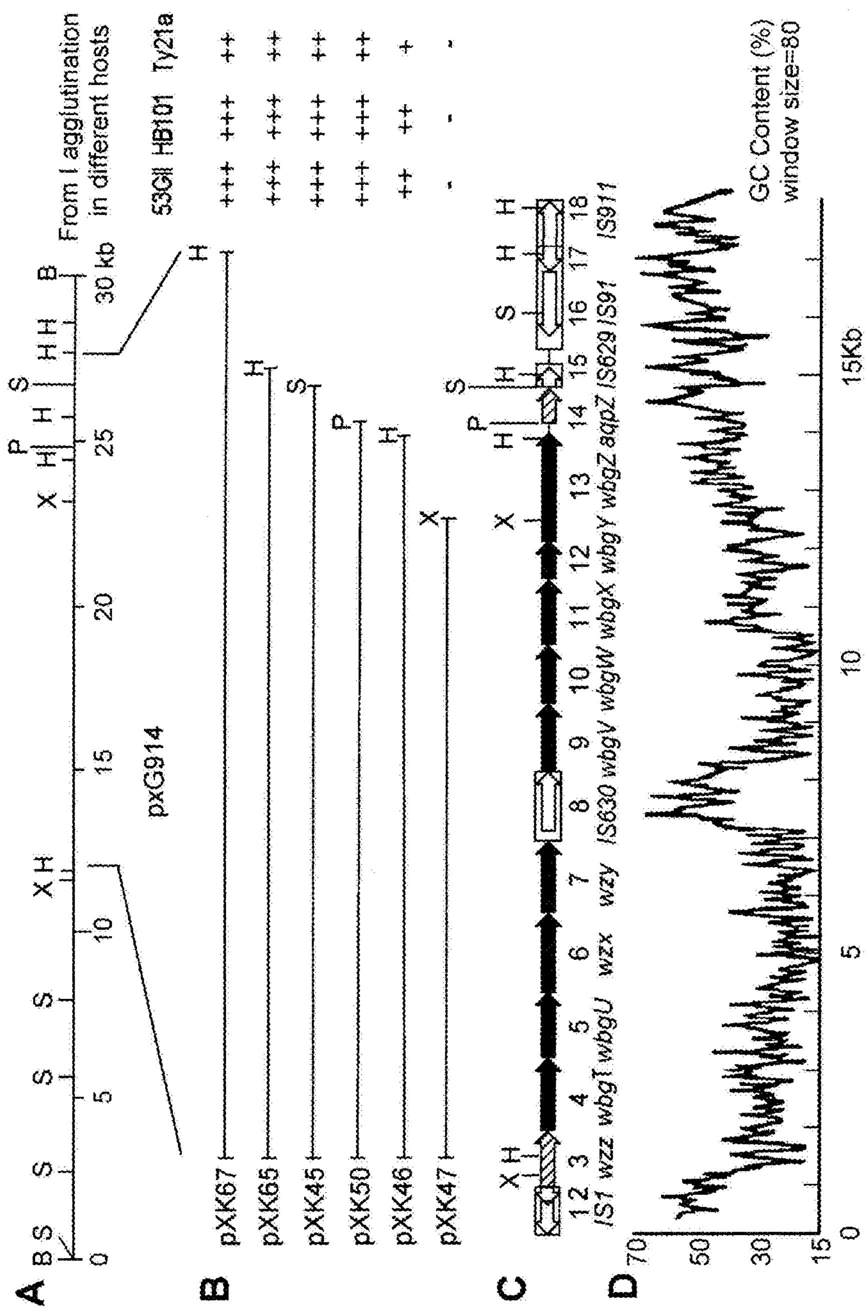
FIG. 1. Cloning and downsizing of the *S. sonnei* form I biosynthetic gene cluster for sequencing and O-antigen expression studies. (A) Restriction map of the 30 kb BamH1 insert from cosmid pXG914. (B) The inserts of plasmid subclones prepared to define a minimal essential region for form I O-antigen expression, defined by anti-form I specific bacterial agglutination of recipient *S. sonnei* 53GII, *E. coli* HB101, or *S. Typhi* Ty21a carrying each of these plasmids. (C) Map of the form I gene region showing restriction sites relative to inserts shown in panel B and the location of 18 ORFs identified by sequence analysis. Filled ORFs represent the genes required for form I O-Ps biosynthesis in plasmid bearing subclones. Restriction endonuclease sites are shown for BamHI (B), HindIII (H), PmeI (P), SmaI (S), and XbaI (X). (D) Percent GC content of the 17,986 by form I biosynthetic region and flanking sequences.

The term "operon" refers to a cluster of functionally related genes whose expression or operation is regulated by the same preceeding promoter gene. The term "rfb/rfc" is the gene symbol for the gene cluster which encodes all of the proteins required to synthesize, polymerize, and transport to the bacterial surface the form I O-Polysaccharide of *Shigella sonnei*. The rfb/rfc gene cluster comprises the genes wbgT, wbgU, wzx, wzy, wbgV, wbgW, wbgX, wbgY, and wbgZ (see Table 2 and SEQ ID NO:7). Included in the cluster but not required for production of the form I O-Ps is the transposable element IS630 (SEQ ID NO:15). Also included in the gene cluster are the promoter and operator sequences (SEQ ID NO:12) for the gene cluster located in the carboxyterminus of the wzz gene immediately upstream (5') of the wbgT gene, and the transcriptional terminator sequences are located immediately downstream (3') of the wbgZ gene (SEQ ID NO:13). Sequences which naturally flank the rfb/rfc gene cluster include those sequences found on the *S. sonnei* virulence plasmid containing the rfb/rfc gene cluster not contained in SEQ ID NO:2.

The term "form I O-Polysaccharide" refers to the *Shigella sonnei* O antigen composed of disaccharide repeating units containing two unusual amino sugars, 2-amino-2-deoxy-L-alturonic acid (L-AltNAcA) and 2-acetamido-4-amino-2,4,6-trideoxy-D-galactose (4-nD-FucNAc).

The term "form I O-Ps" is a short hand designation for and used interchangeably herein for the *Shigella sonnei* form I O-Polysaccharide surface antigen.

The term "O17 gene cluster" is the name of the gene cluster isolated from Plesiomonas *shigelloides* (*P. shigelloides*) encoding the genes wbgT, wbgU, wzx, wzy, wbgV, wbgW, wbgX, wbgY, and wbgZ (SEQ ID NO:17). The genes are located in an operon on the bacterial chromosome. The O17 gene cluster is substantially identical to the rfb/rfc gene cluster. The nucleotide sequence identity between the clusters ranges from 95% to 100% depending on the gene. The amino acid sequence identity ranges from 98% to 100%, depending on the gene and the amino acid sequence similarity ranges from 99% to 100% depending on the gene. The O17 gene cluster lacks the IS630 transposable element found in the rfb/rfc gene cluster. The genes encoded by the O17 gene cluster produce the same enzymes and are capable of producing the same form I O-Ps surface antigen as the rfb/rfc gene cluster. Sequences which naturally flank the O17 gene cluster include those sequences found on the *P. shigelloides* bacterial chromosome which are not substantially identical the sequences contained in SEQ ID NO:4.

The term "attenuated," when used with respect to a bacteria, means that the bacteria has lost some or all of its ability to proliferate and/or cause disease or other adverse effect when the bacteria infects an organism. For example, an "attenuated" bacteria can be unable to replicate at all, or be limited to one or a few rounds of replication, when present in an organism in which a wild-type or other pathogenic version of the attenuated bacteria can replicate. Alternatively or additionally, an "attenuated" bacteria might have one or more mutations in a gene or genes that are involved in pathogenicity of the bacteria. Many genes, loci, or operons are known, mutations in which will result in an attenuated bacteria. Examples of attenuated bacteria used as live vaccines include *S. typhi* carrying a mutation in its galE or htrA gene, and *V. cholerae* carrying mutations in its ctxA gene.

A "host organism" is an animal that is a target of vaccination with the attenuated vaccines of the invention. Such host organisms have an immune system that is responsive to inoculation with an immunogen. Suitable host organisms include, for example, humans, rodents, livestock, birds, and other animals in which it is desirable to vaccinate for either therapeutic or prophylactic purposes.

The term "vaccine," is used interchangeably herein with "immunoprotective composition" and as used herein, refers to an immunogen that, upon inoculation into a host organism, can induce complete or partial immunity to pathogenic agents, or can reduce the effects of diseases associated with pathogenic agents.

The terms "nucleic acid" or "oligonucleotide" or grammatical equivalents herein refer to at least two nucleotides covalently linked together. The term nucleic acid is used interchangeably with gene, cDNA, and mRNA encoded by a gene. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49(10):1925) and references therein; Letsinger (1970) J. Org. Chem. 35:3800; Sprinzl et al. (1977) Eur. J. Biochem. 81:579; Letsinger et al. (1986) Nucl. Acids Res. 14:3487; Sawai et al. (1984) Chem. Lett. 805, Letsinger et al. (1988) J. Am. Chem. Soc. 110: 4470; and Pauwels et al. (1986) Chemica Scripta 26:141 9), phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321, O-methylphosphoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31:1008; Nielsen (1993) Nature, 365:566; Carlsson et al. (1996) Nature 380:207). Other analog nucleic acids include those with positive backbones (Denpcy et al. (1995) Proc. Natl. Acad. Sci. USA 92:6097; non-ionic backbones (U.S. Pat. Nos. 5,386,023, 5,637,684, 5,602,240, 5,216,141 and 4,469,863; Angew. (1991) Chem. Intl. Ed. English 30:423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4:395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

A "exogenous DNA segment", "heterologous sequence" or a "heterologous nucleic acid", as used herein, is one that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-RJB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids (typically less than 5%, more typically less than 1%) in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (1), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3.sup.rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 15 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

The term "isolated", when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

The term "naturally-occurring" is used to describe an object that can be found in nature as distinct from being artificially produced by man. For example, an organism, or a polypeptide or polynucleotide sequence that is present in an organism (including viruses, bacteria, protozoa, insects, plants or mammalian tissue) that can be isolated from a source in nature and which has not been intentionally modified by man in the laboratory is naturally-occurring.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

A nucleic acid is "operably linked" when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

The term "recombinant" when used with reference to a bacteria indicates that the host bacteria contains a heterologous nucleic acid, or expresses a peptide or protein encoded by a heterologous nucleic acid. Heterologous nucleic acids can integrate into the host bacteria chromosome and be expressed from host or heterologous promoters. Alternatively, heterologous nucleic acids can be expressed from an autonomously replicating plasmid. Recombinant bacteria can contain genes that are not found within the native (non-recombinant) form of the bacteria. Recombinant bacteria can also contain genes found in the native form of the bacteria wherein the genes are modified and re-introduced into the cell by artificial means. The term also encompasses bacteria that contain a nucleic acid endogenous to the bacteria that has been modified without removing the nucleic acid from the bacteria; such modifications include those obtained by gene replacement, site-specific mutation, and related techniques.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide or series of peptides), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette. The recombinant expression cassette may be located on an autonomously replicating plasmid or may be integrated into the host genome.

The term "selectable marker" refers to a nucleotide sequence that encodes a protein and that confers either a positive or negative selective advantage to a bacteria expressing that marker. For example, an expression cassette comprising a selectable marker could comprise the aspartate β-semialdehyde dehydrogenase (asd) gene operably linked to a promoter. A recombinant plasmid capable of expressing asd could complement the asd phenotype of asd deletion mutants. Bacteria lacking asd would not be able to synthesize diaminopimelic acid, an essential element of the peptidoglycan of the bacterial cell wall, and would die. Examples of other selectable markers useful in bacteria include SacB, aroA, and heavy metal ion resistance genes.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mot. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology, John Wiley and Sons Inc. New York, N.Y. (2001)).

One example of an algorithm that is suitable for determining percent sequence identity and sequence similarity is the BLAST algorithm, which is described in Altschul et al., J. Mol. Biol: 215:403-410 (1990). Software for performing BLAST analyses is publicly available through the National Center for Biotechnology Information (www.ncbi.nlm.nih.gov).

A "subsequence" refers to a sequence of nucleic acids or amino acids that comprise a part of a longer sequence of nucleic acids or amino acids (e.g., polypeptide) respectively.

The term "protective immunity" means that a vaccine or immunization schedule that is administered to a mammal induces an immune response that prevents, retards the development of, or reduces the severity of a disease or infection that is caused by *Shigella sonnei*, or diminishes or altogether eliminates the symptoms of the disease or infection.

The phrase "sufficient to invoke an immunoprotective response" means that there is a detectable difference between an immune response indicator measured before and after administration of a particular antigen preparation. Immune response indicators include but are not limited to: antibody titer or specificity, as detected by an assay such as enzyme-linked immunoassay (ELISA), bactericidal assay, flow cytometry, immunoprecipitation, Ouchter-Lowny immunodiffusion; binding detection assays of, for example, spot, Western blot or antigen arrays; cytotoxicity assays, etc.

A "surface antigen" is an antigen that is present in a surface structure of a bacteria such as the *Shigella sonnei* form I O-Ps antigen, which is capable of generating an immunoprotective response when expressed by a recombinant bacteria and presented to a host organism in an immunoprotective composition.

DETAILED DESCRIPTION

This invention is directed to a living, attenuated, oral vaccine capable of inducing an immunoprotective response against *Shigella sonnei*. The invention is based on an attenuated strain of bacteria which has been genetically engineered to carry the genes encoding the enzymes capable of synthesizing the *S. sonnei* form I O-Ps antigen. These recombinant bacteria are useful in an immunoprotective composition to induce an immunoprotective response in a susceptible host organism. In addition to infections caused by *S. sonnei*, enteric infections caused by other organisms are considered amenable to treatment with a combination vaccine according to this invention. For example, genes encoding the surface antigens derived from other *Shigella* strains such as *S. flexneri, S. dysenteriae*, and *S. boydii* (see e.g., Baron et al., Infect. and Immun. 55:2797 (1987)) can be transferred into recipient bacteria independently of or concurrently with the *S. sonnei* rfb/rfc gene cluster. The resulting recombinant bacteria can then express two or more heterologous surface antigens suitable for generating an immunoprotective response in a host organism. Alternatively, the oral vaccine may contain multiple strains of attenuated bacteria, each strain expressing a different heterologous antigen. This resulting vaccine would also be suitable for generating an immunoprotective response against multiple antigens in a host organism.

Genes encoding other antigens, such as *Salmonella typhi* Vi antigen and genes encoding non-toxic variants of toxins derived from enterotoxogenic strains such as *Escherichia coli, Vibrio cholera*, and *Yersinia* can also be transferred independently of or concurrently with the *S. sonnei* rfb/rfc gene cluster into bacterial hosts (see e.g. U.S. Pat. No. 4,632,830). In a preferred embodiment, the Vi antigen or non-toxic variants of the enterotoxins should be expressed in such a way that the proteins are present on the surface of the recombinant bacteria or secreted by the recombinant bacteria. The resulting recombinant bacteria would be useful in immunogenic compositions for generating an immunoprotective response to these additional antigens. Enteric disease caused by bacterial secretion of an exotoxin exemplified by staphylococcal, clostridial or similar food poisoning are also considered amenable to treatment with an immunoprotective composition according to this invention using an approach similar to the approach used for enterotoxins.

Nucleic acids encoding the *S. sonnei* rfb/rfc gene cluster as exemplified in SEQ ID NO:2-4, the O17 gene cluster, or other antigens are typically cloned into vectors for transformation into bacterial cells for replication, expression, and cell transformation. Such vectors are typically prokaryotic vectors, e.g., plasmids that act as shuttle vectors, or for production of protein. The elements that are typically included in vectors include a replicon that functions in the recombinant bacteria, a gene encoding a selectable marker to permit selection of bacteria that harbor recombinant plasmids, and unique restriction sites in nonessential regions of the plasmid to allow insertion of recombinant sequences. Selectable markers may include a gene encoding antibiotic resistance, or may include a gene encoding a protein whose naturally occurring gene has been mutated resulting in an attenuated strain of bacteria. Examples of suitable targets for mutation include genes that would result in essential auxotrophic pathways, loci encoding regulons that exert pleiotropic effects such as the cya/crp system, the ompR/envZ system or the phoP system (see e.g. U.S. Pat. Nos. 5,672,345, 5,980,907, 6,190,669). A preferred selectable marker is the aspartate β-semialdehyde dehydrogenase (asd) gene operably linked to a promoter. A recombinant plasmid capable of expressing asd could complement the asd phenotype of attenuated bacterial strains suitable for use in vaccines and containing asd deletion mutantations. Bacteria lacking asd would not be able to synthesize diaminopimelic acid, an essential element of the peptidoglycan of the bacterial cell wall, and would die. Examples of other selectable markers useful in bacteria include SacB, aroA, and heavy metal ion resistance genes.

Alternatively, vectors containing nucleic acids encoding the enzymes that produce the form I O-Ps antigen may be transformed into bacterial cells carrying a mutation in the msbB gene. Mutations in this gene fail to myristylate lipid A. Bacteria containing this mutation may contain additional mutations resulting in attenuated bacteria and vectors containing the enzymes that produce the form I O-Ps may contain selectable markers. Form I O-Ps produced in bacteria containing a mutation in the msbB gene may be purified using techniques well known to those of skill in the art and used in an immunoprotective composition directly.

To obtain expression of the *S. sonnei* rfb/rfc gene cluster, the O17 gene cluster, or other antigens, the nucleic acids encoding the appropriate gene(s) are typically subcloned using techniques well known to those of skill in the art, into an expression vector that contains a promoter to direct transcription. Suitable bacterial promoters are well known in the art and described, e.g., in Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 2001).

The promoter used to direct expression of the *S. sonnei* rfb/rfc gene cluster, the O17 gene cluster, or other antigen depends on the particular application. Either a constitutive or an inducible promoter may be used. Preferably, a constitutive promoter is used. Alternatively, the promoter which drives the normal expression of the *S. sonnei* rfb/rfc gene cluster can be used.

The promoter typically can also include elements that are responsive to transactivation, e.g., hypoxia response elements, Gal4 response elements, lac repressor response element, and small molecule control systems such as tet-regulated systems and the like (see, e.g., Gossen & Bujard, Proc. Nat'l Acad. Sci. USA 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)).

In addition to the promoter, the expression vector typically contains a transcription unit or expression cassette that contains all the additional elements required for the expression of the nucleic acid in recombinant bacteria. A typical expression cassette thus contains a promoter operably linked, e.g., to the nucleic acid sequence encoding the rfb/rfc gene cluster, and signals required, e.g., for transcriptional termination, ribosome binding sites, or translation termination. Additional elements of the cassette may include, e.g., regulatory proteins.

Standard bacterial vectors include plasmids such as pBR322 based plasmids, pBR325, pUC18, pSKF, pET23D, and pBR322 based cosmid vectors such as pHC79 and pCVD551. Vectors based on the bacterial plasmid pSC101 such as pGB-2 may also be used.

Standard transformation methods are used to produce bacterial cell lines that express the surface antigen proteins of the invention. Transformation of prokaryotic cells are performed according to standard techniques (see, e.g., Morrison, J. Bact. 132:349-351 (1977); Sambrook et al. supra; Ausubel et al. supra). These methods include microinjection, ballistics, use of calcium chloride transformation, infection, conjugation, and electroporation of plasmid vectors, both episomal and integrative, and any of the other well known methods for introducing cloned genomic DNA, synthetic DNA or other foreign genetic material into a recombinant bacteria (see, e.g., Sambrook et al., supra, see also U.S. Pat. No. 5,049,386, U.S. Pat. No. 4,946,787; U.S. Pat. No. 4,897,355; WO 91/17424, and WO 91/16024). It is only necessary that the particular genetic engineering procedure used be capable of successfully introducing at least one gene into the recombinant bacteria capable of expressing the protein of choice.

The microorganisms which are used to express the *S. sonnei* rfb/rfc gene cluster, the O17 gene cluster and other antigens for use in immunoprotective compositions include without limitation, *Campylobacter* sp., *Yersinia* sp., *Helicobacter* sp., *Gastrospirillum* sp., *Bacteroides* sp., *Klebsiella* sp., *Lactobacillis* sp., *Streptococcus gordonii, Enterobacter* sp., *Salmonella* sp., *Shigella* sp., *Aeromonas* sp., *Vibrio* sp., *Clostridium* sp., *Enterococcus* sp. and *Escherichia coli* (see e.g. U.S. Pat. Nos. 5,858,352, and 6,051,416, and Levine et al., in "New Generation Vaccines Second Edition" ed. Levine et al., Marcel Dekker, Inc. pp 351-361 (1997), Levine et al., in "New Generation Vaccines Second Edition" ed. Levine et al., Marcel Dekker, Inc. pp 437-446 (1997), Butterton et al., in "New Generation Vaccines Second Edition" ed. Levine et al., Marcel Dekker, Inc. pp 379-385 (1997) and Fennelly et al., in "New Generation Vaccines Second Edition" ed. Levine et al., Marcel Dekker, Inc. pp 363-377 (1997)).

Preferred enteric bacteria that the various aspects of the present invention relate to are *Campylobacter jejuni, Campylobacter coli, Listeria monocytogenes, Yersinia enterocolitica, Yersinia pestis, Yersinia pseudotuberculosis, Escherichia coli, Shigella flexneri, Shigella sonnei, Shigella dysenteriae, Shigella boydii, Helicobacter pylori, Helicobacter felis, Gastrospirillum hominus, Vibrio cholerae, Vibrio parahaemolyticus, Vibrio vulnificus, Bacteroides fragilis, Clostridium difficile, Salmonella typhimurium, Salmonella typhi, Salmonella gallinarum, Salmonella pullorum, Salmonella choleraesuis, Salmonella enteritidis, Klebsiella pneumoniae, Enterobacter cloacae*, and *Enterococcus faecalis*. Preferred *Escherichia coli* include but are not limited to entero-toxic, entero-hemorrhagic, entero-invasive, entero-pathogenic or other strains.

More preferred strains of *Escherichia coli* include DH5α and HB101. More preferred strains of *Salmonella typhi* include CVD 908, CVD 908-htrA, X4073 and TY800. More preferred strains of *Shigella sonnei* include 53GI and 53 GII.

Most preferred strains of bacteria to use as live attenuated vaccines include *S. typhi*, strain Ty21a, which carries a mutation in its galE gene, and *V. cholerae* carrying mutations in its ctxA gene which prevent the expression of cholera toxin.

Attenuated vaccines can be administered directly to the mammal. The vaccines obtained using the methods of the invention can be formulated as pharmaceutical compositions for administration in any suitable manner. The preferred route of administration is oral. Other routes of administration include rectal, intrathecal, buccal (e.g., sublingual) inhalation, intranasal, and transdermal (see e.g. U.S. Pat. No. 6,126,938). Although more than one route can be used to administer a particular composition, a particular route can often provide a more immediate and more effective reaction than another route.

The immunoprotective compositions to be administered are provided in a pharmaceutically acceptable solution such as an aqueous solution, often a saline or buffered solution, or they can be provided in powder form. There is a wide variety of suitable formulations of pharmaceutical compositions of the present invention. See, e.g., Lieberman, Pharmaceutical Dosage Forms, Marcel Dekker, Vols. 1-3 (1998); Remington's Pharmaceutical Science, 17th ed., Mack Publishing Company, Easton, Pa. (1985) and similar publications. The compositions may also include an adjuvant. Examples of known suitable adjuvants include alum, aluminum phosphate, aluminum hydroxide, and MF59 (4.3% w/v squalene, 0.5% w/v Tween 80, 0.5% w/v Span 85)—these are the only ones currently licensed for use in humans. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, or Bacille Calmette-Guerin (BCG). The effectiveness of an adjuvant may be determined by measuring the amount of antibodies directed against the immunogenic antigen.

The concentration of immunogenic antigens of the invention in the pharmaceutical formulations can vary widely, i.e.

from less than about 0.1%, usually at or at least about 2% to as much as 20% to 50% or more by weight, and will be selected primarily by fluid volumes, viscosities, etc., in accordance with the particular mode of administration selected.

Formulations suitable for oral administration can consist of (a) liquid solutions, such as an effective amount of the recombinant bacteria suspended in diluents, such as buffered water, saline or PEG 400; (b) capsules, sachets or tablets, each containing a predetermined amount of the active ingredient, as lyophilized powder, liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the attenuated vaccines, when administered orally, must be protected from digestion. This is typically accomplished either by complexing the vaccines with a composition to render it resistant to acidic and enzymatic hydrolysis or by packaging the vaccines in an appropriately resistant carrier such as a liposome or enteric coated capsules. Means of protecting the attenuated bacteria from digestion are well known in the art. The pharmaceutical compositions can be encapsulated, e.g., in liposomes, or in a formulation that provides for slow release of the active ingredient.

The attenuated vaccines, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

The dose administered to a patient, in the context of the present invention should be sufficient to effect a beneficial therapeutic and/or prophylactic response in the patient over time. The dose will be determined by the efficacy of the particular attenuated vaccine employed and the condition of the patient, as well as the body weight or vascular surface area of the patient to be treated. The size of the dose also will be determined by the existence, nature, and extent of any adverse side-effects that accompany the administration of a particular vaccine in a particular patient.

In determining the effective amount of the vaccine to be administered in the treatment or prophylaxis of an infection or other condition, the physician evaluates vaccine toxicities, progression of the disease, and the production of anti-vaccine vector antibodies, if any.

The compositions are administered to an animal that is at risk from acquiring an infection caused by *S. sonnei* or to prevent or at least partially arrest the development of the infection and its complications. An amount adequate to accomplish this is defined as a "therapeutically effective dose." Amounts effective for therapeutic use will depend on, e.g., the antigen composition, the manner of administration, the weight and general state of health of the patient, and the judgment of the prescribing physician. Single or multiple doses of the antigen compositions may be administered depending on the dosage and frequency required and tolerated by the patient, and route of administration.

In particular embodiments, a therapeutically effective dose of the immunoprotective composition is administered to an individual. Amounts of live attenutated bacteria expressing the *S. sonnei* rfb/rfc gene cluster (SEQ ID NOs: 2-4), the O17 gene cluster, or other antigens present in the initial immunization generally range from about $5\times10^6$ to $5\times10^{11}$ organisms per patient, and more commonly from about $5\times10^8$ to $5\times10^9$ organisms per patient.

The existence of an immune response to the first dose of the immunoprotective composition may be determined by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like) prior to administering a subsequent dose. The existence of an immune response to the first dose may also be assumed by waiting for a period of time after the first immunization that, based on previous experience, is a sufficient time for an immune response and/or priming to have taken place—e.g. 1, 2, 4, 6, 10 or 14 weeks. Boosting dosages of the immunoprotective composition will contain from about $5\times10^6$ to $5\times10^{11}$ organisms per patient, depending on the nature of the immunogen.

The immunoprotective compositions are typically administered to an individual that is immunologically naive with respect to *Shigella sonnei*. In a particular embodiment, the individual is a human child about 1-4 years of age or younger, and the antigen compositions are administered preferrably at 12 months of age with booster doses given approximately one week apart. Usually, 2-4 doses may be sufficient, however additional doses may be required to achieve a high level of immunity. Additional booster doses may be given every 1-5 years, as necessary, to maintain a high level of immunity.

In general, administration to any individual should begin prior to the first sign of disease, or possibly at the first sign of possible or actual exposure to *Shigella.*

The toxicity and therapeutic efficacy of the attenuated vaccines provided by the invention are determined using standard pharmaceutical procedures in cell cultures or experimental animals. One can determine the $ED_{50}$ (the dose therapeutically effective in 50% of the population) using procedures presented herein and those otherwise known to those of skill in the art.

The attenuated vaccines of the invention can be packaged in packs, dispenser devices, and kits for administering genetic vaccines to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a particular infectious disease, enteric disorder, or for preventing or treating other diseases or conditions that are mediated by, or potentially susceptible to, a mammalian immune response.

EXAMPLES

The following example is offered to illustrate, but not to limit the claimed invention.

I. Materials and Methods

Bacterial Strains, Plasmids, and Growth Conditions.

The bacterial strains and plasmids utilized are described in Table 1. Wild type *S. sonnei* strain 53G form I (i.e. 53GI), harboring the 180 kb virulence plasmid, was used for cloning studies and as a positive control for LPS analysis and immunoblot assays. Studies of plasmid-based form I O-Ps expression were performed in *E. coli* strains HB101 or DH5α, *Salmonella* serovar *Typhi* strain Ty21a, and virulence plasmid-minus *S. sonnei* strain 53G form II (i.e. 53GII).

Cosmids pHC79 and pCVD551 (kindly provided by Timothy McDaniel, Center for Vaccine Development, University of Maryland, Baltimore, Md.) were employed to clone segments of the 180 kb plasmid of *S. sonnei* 53GI. Plasmid vectors pBR325, pGB2 and pUC18 were used for subcloning.

Bacterial strains were grown at 37° C. in Luria-Bertani broth (LB) or on LB agar (DIFCO®). Plasmid-containing strains were selected in media containing ampicillin (Ap, 100 μg/ml), spectinomycin (Sp, 50 μg/ml), chloramphenicol (Cm, 35 μg/ml), or tetracycline (Tc, 20 μg/ml).

Plasmid Manipulations.

Unless otherwise noted all DNA manipulations were performed essentially following the procedures outlined in Sambrook et al. (35). Restriction enzymes were used with the buffers supplied by the manufacturer (Roche). Electroporation of plasmid constructs was performed with a GENE PULSER® (Bio-Rad).

Cloning of *S. sonnei* Form I Genes.

pWR101 and pWR102 are form I antigen-expressing cosmids that contain large overlapping regions of the *S. sonnei* 180 kb plasmid from strain 53GI (D. J. Kopecko, L. S. Baron, T. L. Hale, S. B. Formal and K. Noon, Abstr. 83th Annual Meeting of the American Society for Microbiology, abstr. D 10, 1983). These recombinant cosmids, initially selected in *E. coli* recipients on antibiotic-containing media, were identified by colony immunoblotting and bacterial agglutination assays using purified form I O-antigen-specific, rabbit polyclonal antiserum (see below). The essential form I genes and flanking sequences were subcloned from the 39 kb insert of pWR101 (Table 1). First, pWR101 DNA was digested with BamH1 and a resulting 30 kb fragment was ligated to the isoschizomer BglII-digested cosmid pCVD551. DNA was packaged in lambda phage particles in vitro using a commercial kit (Gigapack II plus, Stratagene) according to the manufacturer's instructions. Lambda-packaged DNA was used to infect *E. coli* HB101 or DH5α, and the recombinants were screened for form I antigen expression by colony immunoblotting. A HindIII partial digest of one form I-expressing clone, designated pXG914, was ligated to the multicopy plasmids pUC18 and pBR325, and the low copy plasmid pGB-2 (7). Inserts representing one or more of three contiguous HindIII fragments of 12.4, 1.2 and 2.1 kb were initially obtained (i.e. pXK67 (comprising SEQ ID NO:1), pXK68 (comprising SEQ ID NO:1), pXK66 (comprising SEQ ID NO:2), pXK65 (comprising SEQ ID NO:2) and pXK46 (comprising SEQ ID NO:5)). Additional deletion derivatives (i.e. pXK45 (comprising SEQ ID NO:3), pXK50 (comprising SEQ ID NO:4) and pXK47 (comprising SEQ ID NO:6)) of this region were obtained to delimit the form I biosynthetic region (Table I).

DNA Sequencing and Analysis.

DNA sequencing was performed using Ready Reactions DyeDeoxy Terminator cycle sequencing kits (Applied Biosystems) and an ABI model 373A automated sequencer. Subclones used for sequencing studies included pXK2.1 (comprising SEQ ID NO:9), pXK1.2 (comprising SEQ ID NO:10), pXK1.4 (comprising SEQ ID NO:11), pXK47 and pXG914 (Table 1). Limited sequencing of pWR102 was also performed. Sequences were assembled and analyzed using the VECTOR NTI® suite 6.0 software (InforMax, Inc.). DNA homology searches were performed using the Basic Local Alignment Search Tool (BLAST) of the National Center for Biotechnology Information. The GENBANK® sequence accession number for the 17,986 by sequence of pWR101 identified in this work is AF294823 (comprising SEQ ID NO:7) and the accession number for the 2,964 by sequence of pWR102 is AF455358 (comprising SEQ ID NO:8).

Antisera and Slide Agglutination.

Rabbit polyclonal form I specific antiserum, kindly provided by S. Formal (Walter Reed Army Institute of Research, Washington, D.C.), was produced by repeated immunization of New Zealand white rabbits with whole cells of heat-killed *S. sonnei* 53GI. Group D-specific *Shigella* typing sera (DIFCO®) was also utilized. These rabbit antisera were absorbed with heat-treated (70° C., 30 min) *S. sonnei* form II and *E. coli* HB101 cells. Packed cells (0.1 ml) were added to 1.0 ml of undiluted or 10-fold diluted antiserum, mixed and incubated for 2 h at 37° C. and overnight at 4° C. Following centrifugation, the absorbed antiserum was stored at 4° C. for use in bacterial agglutination assays performed on microscope slides as previously described (12). Absorbed form I-specific antiserum did not agglutinate *E. coli, S. sonnei* 53GII or *Salmonella* host strains.

LPS and Immunoblot Analyses.

*Salmonella, Shigella*, and *E. coli* strains carrying various plasmid constructs were grown overnight with aeration at 37° C. in LB media containing appropriate antibiotics. Bacteria were pelleted by centrifugation and lysed in SDS-PAGE sample buffer containing 4% 2-mercaptoethanol. The sample was boiled for 5 min, treated with proteinase K for 1 h and analyzed by SDS-PAGE using a 15% gel and the Laemmli buffer system (28). Gels were silver-stained (22) or subjected to Western blotting with form I-specific antiserum.

Western blotting was performed using PVDF membranes (Schleicher & Schuell). The membranes were blocked with 5% non-fat dry milk in Tris-buffered saline (TBS; 20 mM Tris-HCl, 150 mM NaCl, pH7.5) and reacted with anti-form I serum followed by protein A-alkaline phosphatase conjugate. The developing solution consisted of 200 mg of Fast Red TR salt and 100 mg of Naphthol NS-MX phosphate (SIGMA®) in 50 ml of 50 mM Tris buffer (pH 8.0).

Recombinant clones expressing the *S. sonnei* O-Ps were identified by colony immunoblotting performed with anti-form I serum and protein A-alkaline phosphatase conjugate as described above. Colonies of recipient *E. coli, S. sonnei* 53G II, or *S. Typhi* strains alone did not react with the absorbed form I-specific antisera under these conditions.

Stability of Form I O-Ps Expression in *Salmonella.*

Several *S. Typhi* Ty21a strains, each containing a different form I-expressing recombinant plasmid, were tested for stability of form I O-Ps expression. Each form I-expressing strain was diluted to approximately 100 cfu per ml and grown for 12 h (i.e. approximately 25 generations) with aeration at 37° C. in LB media under nonselective conditions (i.e. without antibiotics). These cultures were diluted again to 100 cfu per ml in LB and grown for an additional 12 h. Samples taken after 12 and 24 h of nonselective growth were plated onto LB agar without antibiotics and incubated at 37° C. At least 100 colonies of each strain were tested at each time point for O-Ps expression by the colony immunoblot assay.

Animal Immunization Study.

Outbred ICR mice weighing from 13 to 15 g were used to assess immune protection as described previously (12). Vaccine candidate strains and control Ty21a alone were grown overnight in BHI broth (DIFCO®) supplemented with 0.01% galactose, washed, and suspended in sterile saline to a concentration of $5\times10^7$ cfu per ml. Mice were inoculated intraperitoneally with a single 0.5 ml dose of either vaccine or control cell suspensions or sterile saline. Immunized and control mice were challenged 5 weeks postimmunization with $5\times10^5$ cfu (approximately $100\times LD_{50}$) of freshly grown, mid-log phase *S. sonnei* strain 53GI in 0.5 ml of 5% hog gastric mucin (SIGMA®) in sterile saline. Survival was monitored for 96 h.

II. Results

Cloning and Genetic Downsizing for Expression of the Form I O-Antigen Locus.

To delimit the DNA region required for biosynthesis of form I antigen, we initially cloned this region from *S. sonnei* strain 53GI in cosmids (see Methods). The 30 kb BamH1 insert of pXG914, which directs the expression of typical form I LPS in *E. coli*, was partially digested with HindIII and separately ligated to low and high copy plasmid vectors pGB-2, pBR325, and pUC18. The resulting form I-expressing subclones (Table 1), containing inserts comprised of one or more of three adjacent HindIII fragments of 12.4, 1.2, and 2.1 kb (e.g. pXK67, pXK65, and pXK46 and several additional deletion derivatives (i.e. pXK45, pXK47, and pXK50) were characterized for form I expression in three host backgrounds (i.e. *E. coli, S. Typhi*, and *S. sonnei*) (FIG. 1). Plasmid inserts ranging in size from 15.7 to 12.4 kb all directed form I antigen expression in each host as shown by results of bacterial agglutination of plasmid bearing subclones with form I-specific antiserum (FIG. 1B). However, this antiserum did not agglutinate bacteria containing pXK47, which contains an 11 kb insert, like the one previously reported (24) to contain the entire form I biosynthetic region. In the present study, the smallest inserts that directed form I antigen expression were the 12.7 and 12.4 kb inserts of plasmids pXK50 and pXK46, respectively. However, form I specific agglutination of host strains containing pXK46 was weak and did not correlate with the detection of typical polymerized O-antigen as described below.

TABLE 1

Bacterial strains and plasmids

| Strain/Plasmid | Genotype/Description | Reference |
|---|---|---|
| | Strain | |
| *E. Coli* | | |
| DH5α | supE44, hsdR17, recA1, endA1, gyrA96, thi-1, relA1 | (35) |
| HB101 | supE44, hsdS20, ($r_B^-m_B^-$), recA13, ara-14, proA2, lacY1, galk2, rpsL20, xyl-5, mtl-1 | (35) |
| *S. Typhi* | | |
| Ty21a | galE, ilvD, viaB ($Vi^-$), $H_2S^-$ | (14) |
| *S. sonnei* | | |
| 53GI | Form I (phase I), virulent isolate | (26) |
| 53GII | Form II (phase II), avirulent variant | (26) |
| pGB-2 | pSC101 derivative, low copy plasmid; $Sm^r$, $Spc^r$ | (7) |
| pBR325 | pBR322-derived plasmid; $Cm^r$, $Ap^r$, $Tc^r$ | (4) |
| pUC18 | pBR322-derived cloning vector; $Lac^+$, $Ap^r$ | (41) |
| pHC79 | pBR322-derived cosmid; $Ap^r$, $Tc^r$ | (23) |
| pCVD551 | pHC79-derived cosmid; $Cm^r$ | Timothy McDaniel |
| pWR101 | *S. sonnei* form I positive cosmid clone #19; $Tc^r$ | (26) |
| pWR102 | *S. sonnei* form I positive cosmid clone #27; $Tc^r$ | (26) |
| pXG914 | 30 kb BamHI fragment of pWR101 cloned into pCVD551 cosmid; | This study |
| pXK68 | 15.7 kb HindIII fragment of pXG914 cloned into pBR325; $Ap^r$, $Cm^r$ | This study |
| pXK67 | 15.7 kb HindIII fragment of pXG914 cloned into pGB-2; $Sm^r$, $Spc^r$ | This study |
| pXK66 | 13.6 kb HindIII fragment from pXG914 cloned into pBR325; $Ap^r$, $Cm^r$ | This study |
| pXK65 | 13.6 kb HindIII fragment of pXK67 cloned into pGB-2; $Sm^r$, $Spc^r$ | This study |
| pXK45 | 13.3 kb HindIII-SmaI fragment of pXK45 cloned into pGB-2; $Sm^r$, $Spc^r$ | This study |
| pXK50 | 12.7 kb HindIII-PmeI fragment of pXK45 cloned into pGB-2; $Sm^r$, $Spc^r$ | This study |
| pXK46 | 12.4 kb HindIII fragment of pXK67 cloned into pUC18, $Ap^r$ | This study |
| pXK47 | 11.0 kb XbaI-HindIII fragment of pXK46 cloned into pUC18; $Ap^r$ | This study |
| pXK2.1 | 2.1 kb HindIII fragment of pXK67 cloned into pUC18; $Ap^r$ | This study |
| pXK1.2 | 1.2 kb HindIII fragment of pXK67 cloned into pUC18; $Ap^r$ | This study |
| pXK1.4 | 1.4 kb XbaI-HindIII fragment of pXK46 cloned into pUC18; $Ap^r$ | This study |

Figure 2:
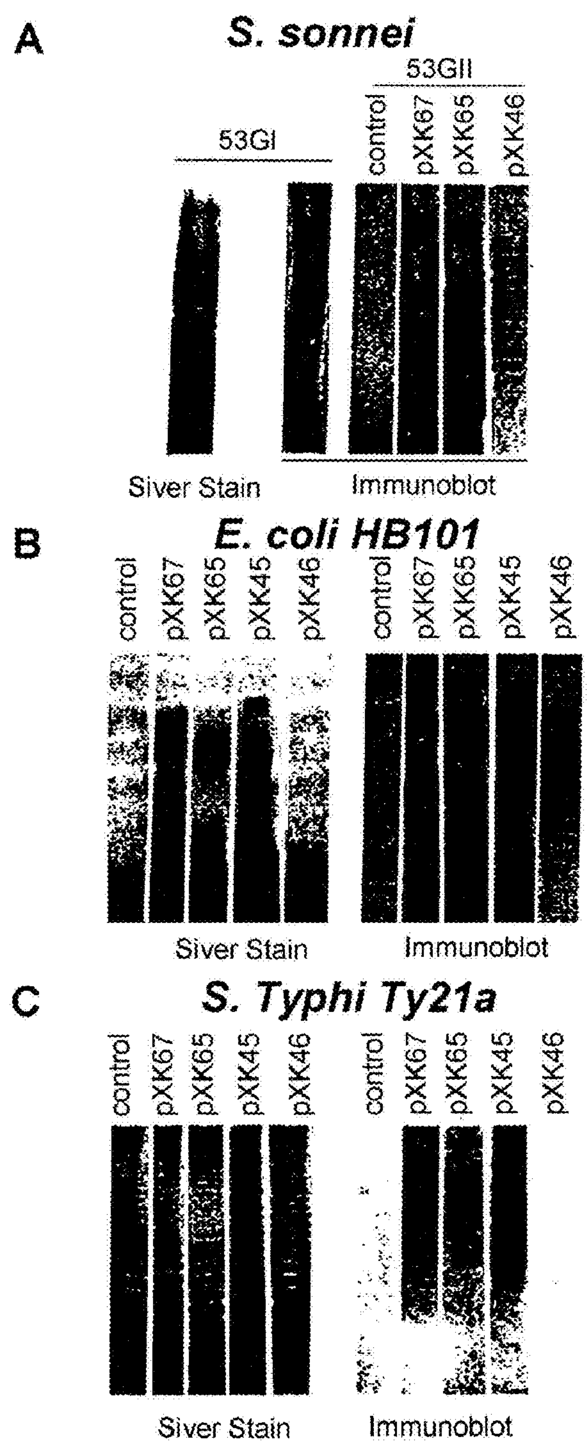
FIG. 2. Detection of SDS-PAGE separated O-Ps by silver staining and anti-form I Western immunoblotting with form I specific antiserum. O-Ps from: (A) *S. sonnei* 53GI, strain 53GII alone (control) or carrying plasmids with different form I-encoding inserts; (B) *E. coli* HB101 alone (control) or carrying different form I-encoding plasmids; (C) *S. typhi* Ty21a alone (control) or carrying different form I-encoding plasmids.

Plasmid-based expression of form I O-Ps in each host was further examined by SDS-PAGE followed by silver-staining and Western blotting with form I-specific antisera (FIG. 2). LPS from wildtype *S. sonnei* 53GI gave a typical O-antigen ladder pattern with the predominant chain length of 20 to 25

O-units as detected by silver stain or immunoblotting (FIG. 2A). Immunoblotting also detected additional material of lower mobility, well above the position of 25 O-repeats, suggesting capsule-like expression. As expected, anti-form I reactive material was not detected with *S. sonnei* 53GII or the "rough" *E. coli* HB101. However, recipient 53011 or HB101 carrying either pXK67 or pXK65 showed typical LPS ladder patterns like that seen from parent strain 53GI. Similar LPS ladder patterns were detected in further studies of *E. coli* carrying cosmid pWR101, pXG914, pXK45 containing a 13.3 kb insert (FIG. 2B) or pXK50 containing a 12.7 kb insert (data not shown). In contrast, a dramatic loss of form I immunoreactive material was noted in either *Shigella* (FIG. 2A) or *E. coli* (FIG. 2B) containing pXK46, which has a 12.4 kb insert. Moreover, host strains carrying pXK47, which has an 11 kb insert, showed no reaction by silver staining or immunoblotting (data not shown).

*S. Typhi* Ty21a exhibited a typical and distinctive 9,12 LPS ladder pattern by silver-stain analysis, but, as expected, showed no form I antigen by immunoblotting (FIG. 2C). The presence of pXK67, pXK65, or pXK45 (FIG. 2C) or the smaller pXK50 (data not shown) in Ty21a did not noticeably affect the silver-stained O-antigen pattern of this strain. However, immunoblot analysis revealed that these plasmids directed the expression of anti-form I reactive material. The form I material in *S. Typhi* did not migrate as LPS and presumably was attached to carrier lipid as proposed previously (37). No immunoreactive form I O-Ps was detected in strain Ty21a carrying pXK46. Thus, the combined results suggest that plasmids pXK67, pXK65, pXK45, and pXK50, but not pXK46, contain the essential genes for synthesizing form I O-Ps in each of the three host strains examined.

Sequence Analysis of the Form I Gene Region.

A contiguous segment of about 18 kb was sequenced to characterize the form I biosynthetic gene region and evolutionarily important adjacent regions, (see FIG. 1C; GENBANK® #AF294823). Primary analysis of this sequence revealed 18 ORFs, the properties of which are summarized in Table 2 and FIG. 1. The notably higher GC content for ORFS, ORFs 11 through 13 and other terminal sequences, compared with the remainder of the form I region, suggests different evolutionary origins for these sequences.

The inserts of all plasmids that direct the expression of typical form I antigen (FIG. 1B) begin at the HindIII site located at nucleotide position 1,310 of our sequence, in the middle of ORF3, a homolog of wzz. Ten identically oriented ORFs (i.e. ORFs 4 to 13) occur within the 12.7 kb insert of pXK50, the smallest insert that directs typical form I antigen expression. One of these ORFs (i.e. ORF 8 in FIG. 1C) represents the transposase of IS630, which is inserted nonpolarly into the C-terminus of the preceding biosynthetic ORF as noted previously (38). All remaining ORFs present within the pXK50 insert are homologs of known genes for polysaccharide biosynthesis (Table 2), except ORF9, which we suggest, encodes a C5-epimerase based on the need for such an enzyme in our proposed biosynthetic pathway (see Discussion). The presence of a putative promoter, identified by a −35 and −10 consensus sequence (ATTACCN$_{15}$TATAGT) (SEQ ID NO:12) at nucleotide positions 1,645 to 1,671 of our sequence (i.e. AF294823, SEQ ID NO:7) and a typical transcriptional terminator, identified by a stem-loop structure and adjacent poly(T) sequence at nucleotide positions 13,930 to 13,949 of SEQ ID NO:7 (and is SEQ ID NO:13) defines an essential 12.3 kb region required for form I O-Ps biosynthesis by our plasmid subclones. This region, which contains 10 intact ORFs, including the transposase of IS630, begins near the 3' end of ORF3 and ends between ORF13 and ORF14 (FIG. 1C).

Sequencing of the operon-adjacent regions revealed several interesting features that aid in understanding the evolution of the plasmid-borne form I region.

TABLE 2

Summary of *S. sonnei* 53G ORFs

| ORF | Gene Name | Location in Sequence | (G + C) % | aa no. | Selected Homolog (accession no.) | Identity % (aa[a]) | Proposed function of 53G protein |
|---|---|---|---|---|---|---|---|
| 1 | insB | 519-16 | 54.4 | 167 | IS1 (InsB), *E. coli* (AJ223474) | 98 (167) | IS1 transposase |
| 2 | insA | 713-438 | 52.5 | 91 | IS1 (InsA), *E. coli* (AJ223475) | 100 (91) | IS1 protein |
| 3 | wzz | 788-1,720 | 36.4 | 310 | Wzz, *Actinobacillus actinomycetemcomitans* (AB041266) | 35 (328) | chain length |
| | | | | | Wzz, *E. coli* (AF011911) | 26 (292) | determinant |
| 4 | wbgT | 1,756-3,069 | 36.1 | 437 | WbpO, *Pseudomonas aeruginosa* (AF035937) | 74 (418) | UDP-GalNAc |
| | | | | | WcdA, *Salmonella typhi* (D14156) | 63 (418) | dehydrogenase |
| 5 | wbgU | 3,150-4,187 | 34.1 | 345 | WbpP, *Pseudomonas aeruginosa* (AF035937) | 67 (343) | UDP-GlcNAc |
| | | | | | WcdB, *Salmonella typhi* (D14156) | 65 (338) | C4-epimerase |
| 6 | wzx | 4,276-5,556 | 28.1 | 426 | Cps19CJ, *Streptococcus pneumoniae* (AF105116) | 21 (394) | repeat unit |
| | | | | | Wzx, *Escherichia coli* (AF104912) | 19 (393) | transporter |
| 7 | wzy | 5,625-6,797 | 29.8 | 390 | Cap14H, *Streptococcus pneumoniae* (X85787) | 25 (201) | polysaccharide polymerase |
| 8 | IS630 | 6,894-7,925 | 52.8 | 343 | IS630 (ORF343), *S. sonnei* (P16943) | 99 (343) | IS630 transposase |
| 9 | wbgV | 7,958-9,202 | 29.9 | 414 | None | none | UDP-GalNAcA C5-epimerase[b] |
| 10 | wbgW | 9,186-10,181 | 26.6 | 331 | WaaV, *E. coli* (AF019746) | 27 (237) | glycosyl transfease |
| | | | | | LgtA, *Neisseria gonorrhoeae* (U14554) | 30 (142) | |
| 11 | wbgX | 10,178-11,332 | 37.6 | 384 | WlbF, *Bordetella bronchiseptica* (AJ007747) | 55 (392) | amino-sugar |
| | | | | | Per, *E. coli* (AF061251) | 34 (383) | synthetase |
| | | | | | RfbE, *Vibrio cholerae* (X59554) | 31 (380) | |
| 12 | wbgY | 11,349-11,939 | 35.4 | 196 | WlbG, *Bordetella pertussis* (X90711) | 53 (194) | glycosyl transferase |
| | | | | | WcaJ, *E. coli* K-12 (U38473) | 34 (197) | |
| | | | | | WbaP, *E. coli* K30 (AF104912) | 31 (212) | |
| 13 | wbgZ | 11,954-13,873 | 44.3 | 639 | WbcP, *Yersinia enterocolitica* (Z47767) | 68 (633) | UDP-GlcNAc |
| | | | | | WbpM, *Pseudomonas aeruginosa* (U50396) | 49 (657) | C6-dehydratase |
| | | | | | WlbL, *Bordetella pertussis* (X90711) | 49 (592) | C4-reductase |
| | | | | | FlaA1, *Helicobacter pylori* (AE000595) | 28 (297) | |
| 14 | aqpZ | 13,992-14,504 | 55.5 | 170 | ORF10P, *P. shigelloides* (AB025970) | 99 (146) | water channel |
| | | | | | AqpZ, *E. coli* (AE000189) | 71 (146) | protein |
| 15 | orfA | 14,657-14,983 | 53.8 | 108 | IS629 (ORFA), *S. sonnei* (P16941) | 99 (108) | IS629 transposase |

TABLE 2-continued

| Summary of *S. sonnei* 53G ORFs | | | | | | |
|---|---|---|---|---|---|---|
| ORF | Gene Name | Location in Sequence | (G + C) % | aa no. Selected Homolog (accession no.) | Identity % (aa[a]) | Proposed function of 53G protein |
| 16 | InsB | 16,706-15,486 | 55.0 | 406 IS91 (TnpA), *E. coli* (X17114) | 94 (406) | IS91 transposase |
| 17 | InsA | 17,071-16,706 | 53.0 | 121 IS91 (ORF121), *E. coli* (S23781) | 95 (121) | IS91 protein |
| 18 | InsB | 17,130-17,978 | 54.8 | 282 IS911 (InsB), *S. dysenteriae* (AAF28127) | 99 (271) | IS911 transposase |

[a]Length of comparable sequence in the homologous protein

[b]Proposed function based on the predicted presence of an enzyme that converts UDP-GalNAcA to UDP-AltNAcA (see Discussion)

Analysis of upstream sequences from pWR101 subclones revealed the presence of a partial wzz (933 bp) created by an IS1 insertion. Sequence homology to the plasmid R100 was noted immediately 5' of this IS1 element (Xu et al., unpublished data; FIG. 3A). Unexpectedly, the 5' region of pWR101 differed from that in pWR102. The latter plasmid contained a partial IS91 (201 bp), a partial IS630 (339 bp), a JUMPstart sequence (i.e. CAGCGCTTTGGGAGCTGAAACT-CAAGGGCGGTAGCGTA) (SEQ ID NO:14), which is characteristic of O-antigen loci and a full-length copy of wzz (1,104 bp) (FIG. 3A). The observation of a full length *S. sonnei* plasmid-borne wzz, as reported previously (38), preceded by a JUMPstart sequence and partial IS elements suggests that this pWR102-derived sequence represents that of the original 180 kb *S. sonnei* virulence plasmid and that during subcloning of this region in pWR101, an IS1 element insertion occurred within wzz causing a 5'-deletion of this gene and adjacent upstream sequences (FIG. 1C). The remnants of IS630 and IS91 found upstream of JUMPstart in pWR102 suggests the insertion of IS91 via its left inverted repeat (IRL) into a -GTTC- target site (33) originally present within IS 630 and subsequent deletion of much of the IS91 element (FIG. 3A).

Immediately downstream of the form I encoding region, a partial aqpZ gene (513 bp) was found that is virtually identical to the 5'-portion of *Pleisiomonas shigelloides* aqpZ (699 bp) (6). Further downstream a partial IS629 element (31), a small fragment of a *Pseudomonas* IS element, a full-length IS91 and partial IS911 sequences were identified (FIG. 3B). The specific target sequence of IS91, -GTTC-, was found immediately adjacent to the right inverted repeat (IRR) of this element, indicating the prior insertion of IS91 into a target site originally present in the middle of IS911. Thus, the region downstream of the form I biosynthetic operon contains numerous IS element remnants, and like the upstream region, serves as a recombinational hotspot.

Stability of Form I O-Ps Expression in a *Salmonella* Vaccine Vector.

Several recombinant plasmids were tested for their ability to direct stable form I O-Ps expression in *S. Typhi* Ty21a. Following electroporation of each plasmid into strain Ty21a, the resulting strain was grown in the absence of antibiotic selective pressure for approximately 25 and 50 generations and then examined for form I antigen expression. The percentage of form I-positive colonies was determined by immunoblot assay of colonies grown on LB agar without antibiotic. *Salmonella* harboring the 15.7 kb form I region insert in the multicopy vector pBR325 (i.e. pXK68) exhibited highly unstable form I O-Ps expression. Thus, following growth for 24 hrs, the loss of antigen expression from *Salmonella* carrying this plasmid was greater than 97% (Table 3). Deletion of IS91 from the 15.7 kb insert of pXK68 to generate the 13.6 kb fragment of pXK66 increased the stability of form I O-Ps expression. The percentage of form I positive colonies was further enhanced when these inserts were carried in the low copy vector, pGB2. The 15.7 kb insert in pGB-2 pXK67) exhibited markedly improved stability of antigen expression compared with the same insert in pBR325. Again, deletion of IS91 from the 15.7 kb insert of pXK67 to generate the 13.6 kb fragment of pXK65 increased the stability of form I O-Ps expression. In fact, as shown in Table 3, pXK65 and pXK45 directed stable form I antigen expression in *Salmonella* over 50 generations.

TABLE 3

Stability of plasmid-based form I O-Ps expression in *S. Typhi* Ty21a[a]

| Plasmid | Vector | Insert (kb) | Percent form I O-Ps positive colonies at: 12 h | 24 h |
|---|---|---|---|---|
| pXK68 | pBR325 | 15.7 | 12.5 | 2.5 |
| pXK66 | PBR325 | 13.6 | 80 | 45.5 |
| pXK67 | pGB-2 | 15.7 | 78 | 69 |
| pXK65 | pGB-2 | 13.6 | 100 | 98.5 |
| pXK45 | pGB-2 | 13.3 | 100 | 97 |

[a]A form I positive colony of each strain was inoculated in L-broth and grown for 12 h (approximately 25 generations) before dilution and regrowth in fresh L-broth for an additional 12 h. Samples taken at 12 or 24 h were plated on L-agar and the resulting colonies assayed for form I O-Ps by colony immunoblotting.

Vaccine Protection Study in Mice.

Shigellae are specific for higher primates and nonprimate models do not exist for the development of either typical dysenteric disease from low infectious doses of these bacteria or protective immunity from natural challenge. Nevertheless, mice have been employed previously to demonstrate immune stimulation by a vaccine and specific protection against parenteral challenge with virulent *S. sonnei* (12). In the present study, ICR mice were immunized with a single ip dose of viable *S. Typhi* Ty21a containing pXK65 or pXK45, Ty21a alone, or saline and challenged at 5 weeks post-immunization with $5\times10^5$ virulent *S. sonnei* 53GI (i.e. approximately $100\times LD_{50}$). This challenge resulted in 100% mortality in negative control mice immunized with saline or strain Ty21a alone (Table 4). In contrast, all mice that received Ty21a harboring the stable form I inserts deleted for IS91 and carried by pGB-2 were protected from the *S. sonnei* challenge.

TABLE 4

| Mouse protection against virulent *S. sonnei* challenge | |
|---|---|
| Vaccine (plasmid)/control[a] | Suvivors/total[b] |
| *S. Typhi* Ty21a (pXK45) | 8/8 |
| *S. Typhi* Ty21a (pXK65) | 8/8 |
| *S. Typhi* Ty21a | 0/8 |
| Saline | 0/8 |

[a]Vaccine strains containing plasmids or control Ty21a alone were suspended in saline to a concentration of $2.5 \times 10^7$ cells per 0.5 ml dose for intraperitoneal immunization. Saline (0.5 ml) served as control.
[b]Each mouse was challenged intraperitoneally with $5 \times 10^5$ CFU *S. sonnei* 53GI (i.e. 100 × $LD_{50}$) in 0.5 ml saline containing 5% hog gastric mucin and monitored for four days.

III. Discussion

Figure 4:
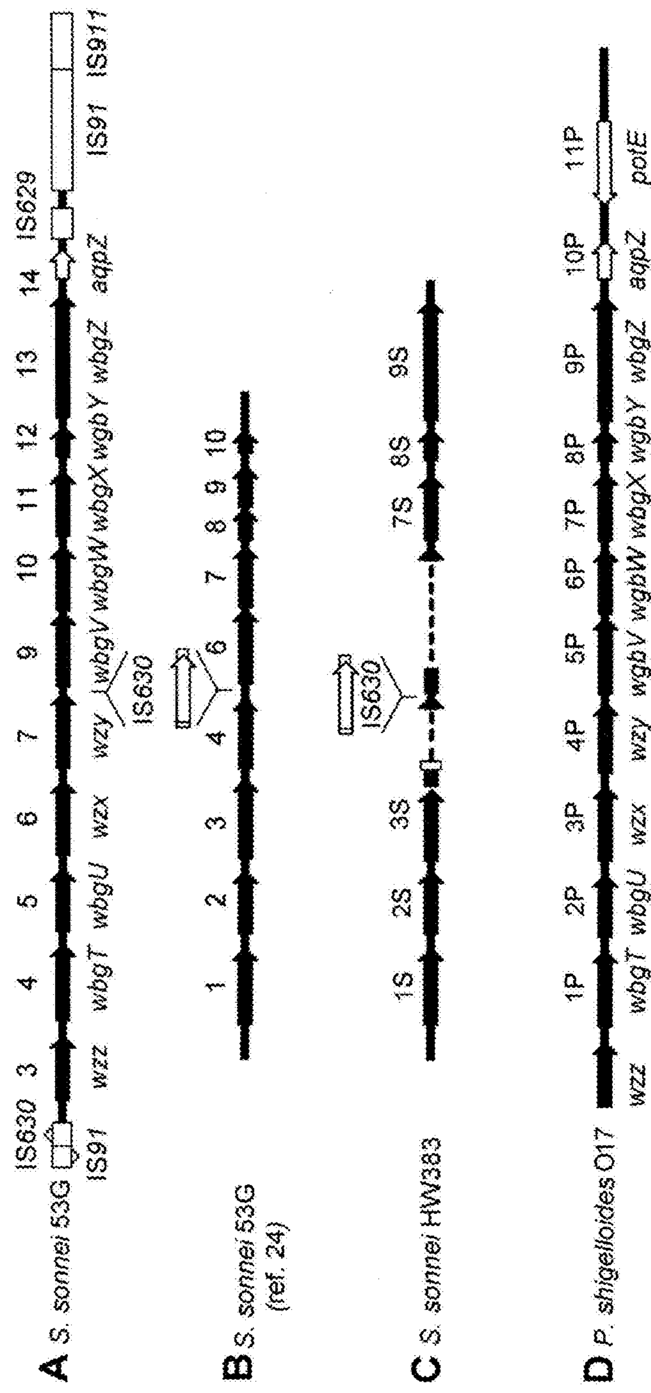
FIG. 4. Comparison of gene clusters for biosynthesis of the *S. sonnei* form I O-Ps and the substantially identical *P. shigelloides O*17 Ps: (A) Composite *S. sonnei* 53G form I gene cluster and flanking regions derived from GENBANK® accession numbers AF285971 (SEQ ID NO:16), AF294823 (SEQ ID NO:7) and AF455358 (SEQ ID NO:8). ORFs are identified numerically as defined in Table 2 and also by gene designations (38). (B) *S. sonnei* 53G form I gene cluster reported by Houng and Venkatesan (24). (C) partial *S. sonnei* HW383 form I gene cluster determined by Chida et al. (6). (D) Composite *P. shigelloides O*17 Ps gene cluster derived from GENBANK® accession numbers AF285970 (SEQ ID NO:17) and AB025970 (SEQ ID NO:18). ORFs are identified numerically and by gene names (38). The ORFs for form I O-Ps biosynthesis by plasmid-bearing subclones are shaded.

The genes controlling form I O-Ps biosynthesis have previously been cloned and sequenced to varying extents as summarized in FIG. 4 (D. J. Kopecko, L. S. Baron, T. L. Hale, S. B. Formal and K. Noon, Abstr. 83th Annual Meeting of the American Society for Microbiology, abstr. D 10, 1983) (6, 24, 38, 42, 45). However, reported sequence differences in the *S. sonnei* form I gene region (FIGS. 4 A and B), combined with limited analyses of LPS expression, have resulted in confusion regarding the essential genes for form I antigen biosynthesis. Houng and Venkatesan (24) reported that these genes were contained within an 11 kb region of the *S. sonnei* 53GI virulence plasmid; DNA sequencing revealed ten ORFs including IS630 (FIG. 4B). However, our findings, which support other recent sequencing studies of the form I gene region in *S. sonnei* strains 53GI and HW383 (FIGS. 4A and C), as well as the corresponding gene region of *P. shigelloides* (FIG. 4D), suggest that the form I biosynthetic region contains an additional gene, designated wbgZ (FIG. 4A), homologs of which occur in many Ps gene clusters (5) but not in the sequence of Houng and Venkatesan (24) (FIG. 4B).

Antibody to form I O-Ps was previously reported to agglutinate subclones expressing an 11 kb form I insert (24), which lacks wbgZ. In contrast, we found that such subclones (i.e. pXK47) were not agglutinated by specific anti-form I antibody, prepared by absorption with form II *S. sonnei* cells. Further, LPS analysis by silver stain or immunoblot showed no detectable form I material from subclones expressing the 11 kb insert, but typical form I LPS from pXK50 subclones expressing the 12.7 kb insert thereby indicating that wbgZ (but not aqpZ) is required for form I O-Ps biosynthesis. The right-hand end of the form I gene region, between wbgZ and aqpZ, is further defined by the presence of a transcriptional terminator in this region and the dramatic effect on form I O-Ps synthesis seen from the short truncation of wbgZ in subclones expressing the 12.4 kb insert (FIG. 2, pXK46).

The left-hand end of the essential form I region is defined by plasmid inserts that begin in the middle of wzz (FIG. 1B) but direct the synthesis of typical form I LPS. The wild type distribution of LPS chain length seen in our *S. sonnei* subclones (FIG. 2A) can be explained by the expression of the previously described chromosomal wzz (38), which apparently determines the chain length of form I LPS. Whereas JUMPstart, a presumed transcriptional antiterminator (43), and plasmid borne wzz may play a role in biosynthesis of LPS by wild type *S. sonnei* and *P. shigelloides* 017, our studies indicate that neither of these loci is essential for form I O-Ps expression from our subclones. Such observations also suggest the presence of a promoter at the 3' end of plasmid borne wzz (6), immediately ahead of wbgT, the first essential gene for plasmid-based form I O-Ps biosynthesis. The IS630 element inserted in the C-terminus of ORF7 (nucleotides 6894-7925 of SEQ ID NO:7 which is SEQ ID NO:15) (i.e. wzy) (38) is evidently also not essential for form I O-Ps biosynthesis as the comparable region of *P. shigelloides*, which lacks IS630, also directs the production of typical LPS. Thus, the available data from studies of LPS biosynthesis clearly indicate that nine genes beginning with wbgT (ORF4) and ending with wbgZ (ORF13) (FIG. 4A) are required for form I antigen biosynthesis in each of the three host genera examined.

Figure 5:
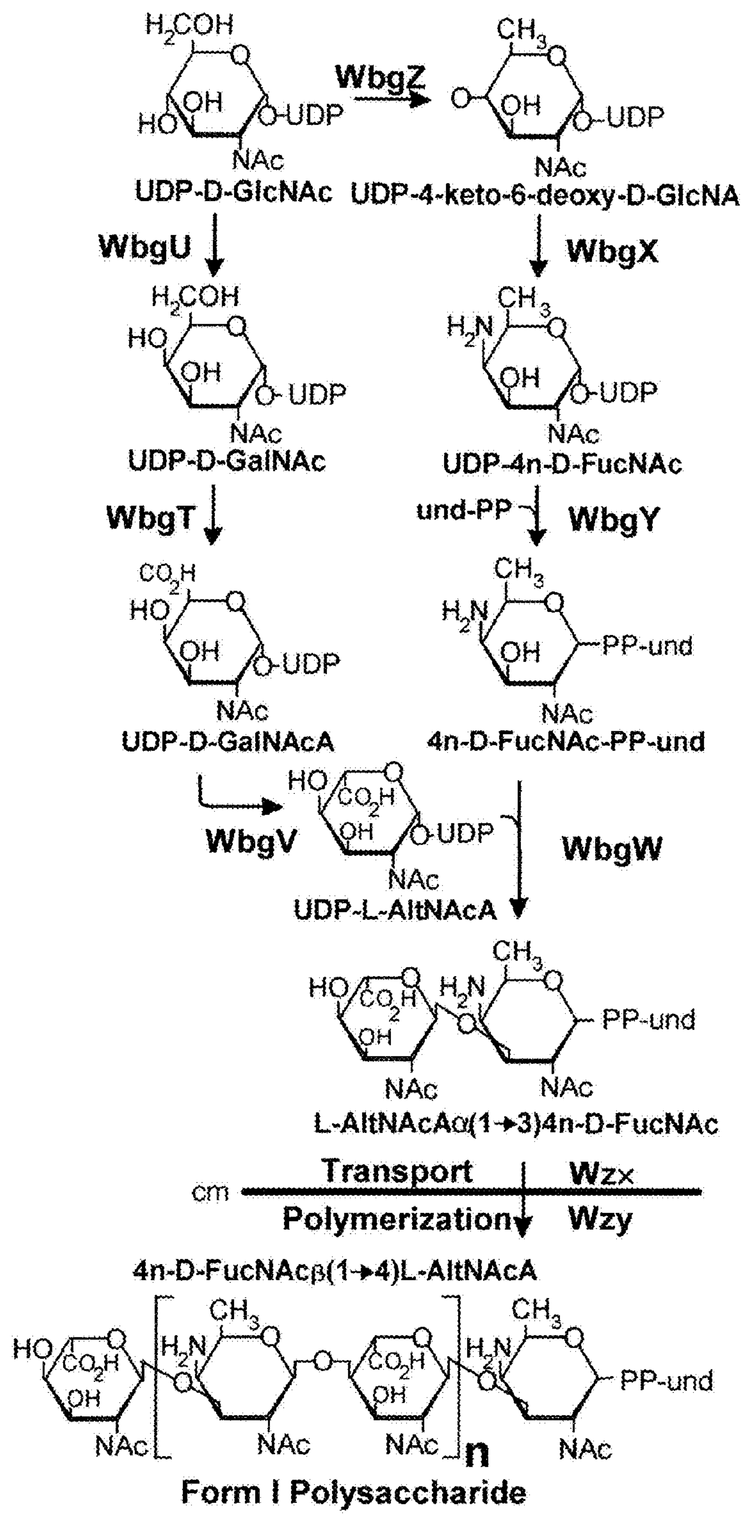
FIG. 5. Proposed pathway for biosynthesis of undecaprenyl phosphate (und-P)-linked, *S. sonnei* form I O-Ps. The pathway is based on the predicted enzymatic activities of *S. sonnei* 53G proteins as summarized in Table 2 and the structural steps required for conversion of UDP-GlcNAc to the putative form I O-Ps precursors, UDP-L-AltNAcA and UDP-4-n-D-FucNAc.

The properties of these nine essential genes (Table 2) provide the basis for the detailed biosynthetic pathway presented as a working hypothesis in FIG. 5. These genes include two (i.e. wbgW and wbgY) for putative glycosyl transferases and two (i.e. wzx and wzy) for proteins that function in the transport and polymerization of form I repeating units. Thus, the remaining five genes of the form I cluster may function to convert available nucleotide-linked sugars to the 4n-D-FucNAc- and L-AltNAcA-containing precursors of the form I disaccharide repeating unit (25). The initial step in formation of UDP-4-n-D-FucNAc was previously proposed to involve conversion of UDP-GlcNAc to UDP-4-keto-6-deoxy-GlcNAc by the action of wbgV (38). Rather than wbgV, we suspect that wbgZ catalyzes this reaction. Homologs of wbgZ, which include FlaA1 of *Helicobacter pylori* and WbpM of *Pseudomonas aeruginosa*, are associated with synthesis of the 2,6-deoxysugars QuiNAc, D-FucNAc, and structurally related derivatives such as 4-n-D-QuiNAc (5), the C4-epimer of 4-n-D-FucNAc. Significantly, FlaA1 of *H. pylori* has recently been identified as a bifunctional UDP-GlcNAc C6-dehydratase/C4-reductase that catalyzes the conversion of UDP-GlcNAc 25, to UDP-QuiNAc through the stable intermediate, UDP-4-keto-6-deoxy-GlcNAc (8). Consequently, the predicted intermediate product of wbgZ, UDP-4-keto-6-deoxy-GlcNAc, is the putative substrate of wbgX (38), which likely catalyzes the formation of 4-n-D-FucNAc (FIG. 5) in a manner similar to the conversion of GDP-4-keto-6-deoxymannose to GDP-perosamine by perosamine synthase of *V. cholerae* 01 (39) and *E. coli* (2).

Homologs of two other *S. sonnei* biosynthetic genes, wbgT and wbgU, occur in a number of bacteria that synthesize N-acetylgalactosamine uronic acid (GalNAcA) including *P. aeruginosa* serotype 06 (1) and Vi-capsule-expressing *Salmonella* serovars (19) (Table 2). The relevant biosynthetic pathway, proposed from studies of *P. aeruginosa* (1), involves the conversion of UDP-GlcNAc to UDP-GalNAc by WbpO and subsequent conversion of UDP-GalNAc to UDP-N-GalNAcA by WbpP. Indeed, recent biochemical studies confirm the identification of WbpP as a UDP-GlcNAc C4-epimerase (8) and WbpO as a UDP-GalNAc dehydrogenase (46). Significantly, D-GalNAcA, the predicted product of WbgT, is the C5-epimer of L-AltNAcA, a constituent of form I O-Ps. Thus, the corresponding precursor, UDP-L-AltNAcA, would be obtained by the action of a C5-epimerase on UDP-GalNAcA. We predict that this activity is provided by WbgV (FIG. 5), the only *S. sonnei* ORF that failed to retrieve significant homologs from the database (Table 2). Although weak homology between WbgV and plant NADH dehydrogenases was previously reported (38), we found that WbgV is not affiliated with these or other NADH-containing enzymes in the Blocks Data Base (Fred Hutchinson Cancer Research Center) thereby questioning the identification of WbgV as a dehydrogenase. Intracellular C5-epimerases that act on nucleotide-linked sugars have not been described to our knowledge, which may contribute to the apparent absence of WbgV homologs in the database. Extracellular C5-epimerases that act on polysaccharides are, however, well documented and include the enzymes of *P. aeruginosa* (13) and *Azotobacter vinelandii* (11) that convert D-mannuronic acid to L-guluronic acid in alginate polymers as well as mammalian enzymes that convert D-glucuronic acid to L-iduronic acid in heparin and heparin sulfate (30).

That the form I O-Ps is linked to the phase II core of *S. sonnei* (25) through 4-n-D-FucNAc suggests that 4-n-D-FucNAc is the first sugar attached to the acyl carrier lipid. This step almost certainly depends on WbgY, which is a homologue of several well-studied glycosyl transferases that link the first sugar of different O-antigen repeating units to carrier lipid (Table 2). WbgW, the other predicted glycosyl transferase (Table 2) presumably completes the biosynthetic unit by transferring L-AltNAcA thereby forming L-AltNAcAα (1→3)4-n-D-FucNAc-PP-und. Indeed, the predicted α(1→3) transfer of L-AltNAcAα by WbgW would resemble the known β(1→3) transfer of D-sugars by WaaV (20) of *E. coli* and LgtA of *N. gonorrhoeae* (16) (Table 2). Wzx, a member of the PST(2) subfamily of polysaccharide transport proteins (34), based on its predicted size (Table 2) and hydropathy profile (results not shown), would then be expected to flip the lipid-linked repeating unit from the cytoplasmic to periplasmic face of the plasma membrane without the aid of auxiliary export proteins. Wzx-mediated transport would provide the substrate for Wzy-dependent polymerization resulting in the formation of a β1-4 linkage between each adjacent repeating unit, thereby completing the form I O-Ps structure (FIG. 5).

Plasmid-based expression of form I O-Ps in *S. typhi* Ty21a, which has a core that is chemically dissimilar to that of Shigellae, resulted in the production of a lipid-linked surface Ps (37) rather than typical form I LPS (FIG. 2C). In contrast, a significant fraction of form I O-Ps synthesized in *S. sonnei* and *E. coli* was ligated to core-Lipid A. However, even from these species, a slow migrating band of form I immunoreactive material, apparently unlinked to core-Lipid A, was detected (FIGS. 2A and B). It is unclear whether this band of core-nonlinked form I material is surface bound through the acyl carrier lipid, or alternatively through another molecule as an O-antigen capsule. As pointed out in a recent review (44), O-Ps capsules are easily overlooked because serological and structural studies have generally been interpreted with the expectation that all surface O antigen is core-lipid A linked. However, examples such as *E. coli* serotype O111 have long been recognized (15) in which the same O-Ps is surface expressed in a LPS form and in an LPS-unlinked capsular form. Clearly, further studies of *S. sonnei* form I O-Ps are needed to clarify this possibility.

Figure 3:
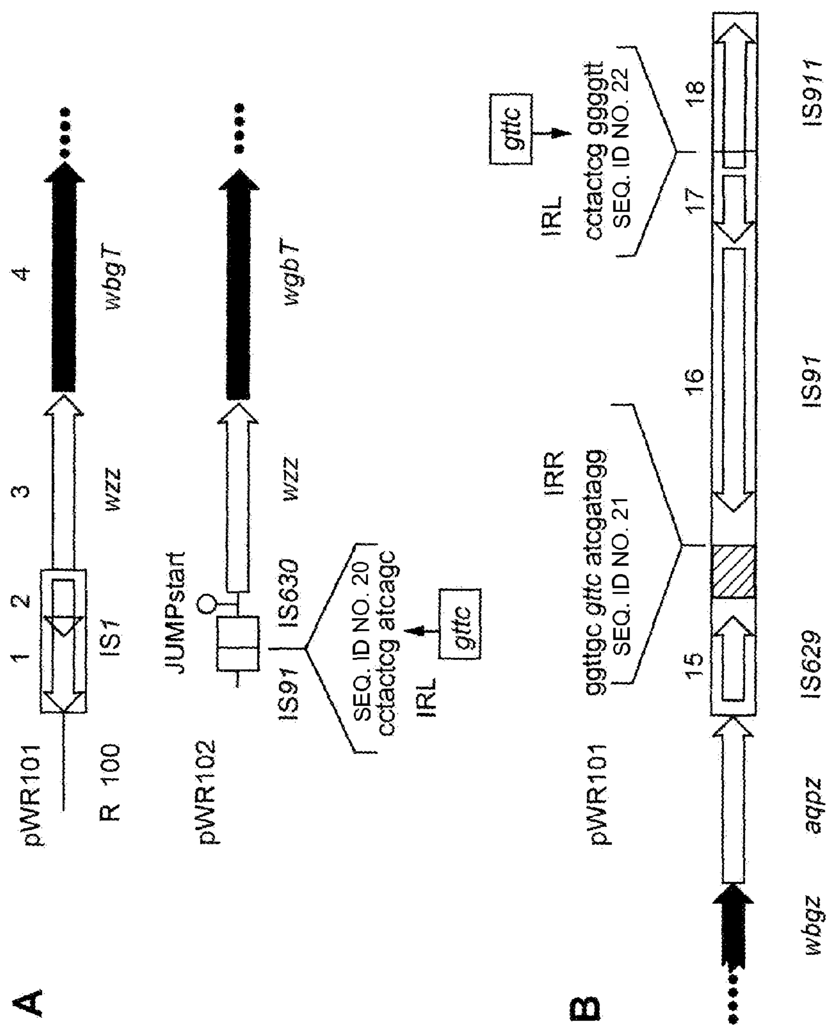
FIG. 3. ORF diagrams of the regions flanking the *S. sonnei* form I biosynthetic gene cluster. (A) Regions of pWR101 and pWR102 upstream of wbgT, (B) Region of pWR101 downstream of wbgZ. The sequences of the left and right inverted repeats (IRL and IRR) of IS91 are shown in bold type. The -gttc- target sequence of IS91 is italicized. The original -gttc- sites within IS630 and IS911 for insertion of IS91 are boxed. A sequence homologous to a *Pseudomonas* IS element occurs within the hatched region.

High homology between the gene regions for O-Ps biosynthesis in *S. sonnei* and *P. shigelloides* (6, 38), over the region from wzz to aqpZ (FIG. 4), supports the proposal of Reeves and coworkers (29) that *S. sonnei* evolved from *E. coli* by the acquisition of the form I biosynthetic region from *P. shigelloides*. The form I operon adjacent sequences obtained herein (FIGS. 1B and 3) provide an improved definition of the limits of the gene transfer event. Comparison of the available *S. sonnei* form I gene region sequences (FIG. 4A) with the analogous *Pleisiomonas* region (FIG. 4D) suggests the transfer of approximately 12.6 kb of *P. shigelloides* chromosomal DNA. The right-hand endpoint apparently occurred at by 513 within aqpZ where sequence homology between *P. shigelloides* and *S. sonnei* ends abruptly. The left-hand junction apparently occurred upstream of JUMPstart where partial IS elements were identified in pWR102 (FIG. 3). Since remnants of IS91, IS630, and other elements have been shown to flank the form I operon in *S. sonnei* (FIGS. 3 and 4A), any of these elements could have been involved in transposition of this region, likely from the *Pleisiomonas* chromosome to a plasmid, which was then transferred to the evolving *E. coli* recipient.

Form I antigen expression is frequently lost in *S. sonnei* mainly by spontaneous loss of the large virulence plasmid (26). Instead of stabilizing form I expression in attenuated *Shigella* for use as a live vaccine, our approach has been to transfer the form I genes into S. *Typhi* Ty21a. Ty21a (14) is a proven safe and effective, mucosally-delivered, live bacterial vaccine which stimulates long-term protection against typhoid fever. In addition, Ty21a has the advantage of oral administration, eliminating the need for needles, syringes and a skilled health professional for immunization. A live, oral candidate vaccine strain, 5076-1C, was previously constructed by introducing the large *S. sonnei* virulence plasmid into Ty21a. The resulting strain was protective in humans challenged with virulent *S. sonnei* (3, 12, 21) but was genetically unstable, resulting in loss of form I O-Ps expression (17). The current study has allowed us to create stable, minimal-sized *S. sonnei* form I region constructs in Ty21a. The stability of plasmid-based expression of form I O-Ps was enhanced by deletion of the downstream IS91 from form I inserts and was further stabilized by use of the low copy vector pGB-2 (Table 3). Animal studies (Table 4) have provided preclinical evidence that these minimal-sized form I region constructs in *S. Typhi* induced protective immunity in a stringent mouse challenge model.

REFERENCES

1. Belanger, M., L. L. Burrows, and J. S. Lam. 1999. Functional analysis of genes responsible for the synthesis of the B-band O antigen of *Pseudomonas aeruginosa* serotype O6 lipopolysaccharide. Microbiology. 145:3505-21.
2. Bilge, S. S., J. C. Vary, Jr., S. F. Dowell, and P. I. Tan. 1996. Role of the *Escherichia coli* 0157:H7 O side chain in adherence and analysis of an rfb locus. Infect Immun. 64:4795-801.
3. Black, R. E, M. M. Levine, M. L. Clements, G. Losonsky, D. Herrington, S. Berman, and S. B. Formal. 1987. Prevention of shigellosis by a *Salmonella typhi-Shigella sonnei* bivalent vaccine. J Infect Dis. 155:1260-5.
4. Bolivar, F. 1978. Construction and characterization of new cloning vehicles. III. Derivatives of plasmid pBR322 carrying unique Eco RI sites for selection of Eco RI generated recombinant DNA molecules. Gene. 4:121-36.
5. Burrows, L. L., R. V. Urbanic, and J. S. Lam. 2000. Functional conservation of the polysaccharide biosynthetic protein WbpM and its homologues in *Pseudomonas aeruginosa* and other medically significant bacteria. Infect Immun. 68:931-6.
6. Chida, T., N. Okamura, K. Ohtani, Y. Yoshida, E. Arakawa, and H. Watanabe. 2000. The complete DNA sequence of the O antigen gene region of *Plesiomonas shigelloides* serotype O17 which is identical to *Shigella sonnei* form I antigen. Microbiol Immunol. 44:161-72.
7. Churchward, G., D. Belin, and Y. Nagamine. 1984. A pSC101-derived plasmid which shows no sequence homology to other commonly used cloning vectors. Gene. 31:165-71.
8. Creuzenet, C., M. Schurr, J. Li, W. W. Wakarchuk, and J. S. Lam. 2000. FlaA1, a new bifunctional UDP-GlcNAc C6 dehydratase/C4 reductase from *Helicobacter pylori*. J Biol. Chem. 275:34873-80.
9. DuPont, H. L., R. B. Hornick, M. J. Snyder, J. P. Libonati, S. B. Formal, and E. J. Gangarosa. 1972. Immunity in shigellosis. L Response of man to attenuated strains of *Shigella*. J Infect Dis. 125:5-11.
10. DuPont, H. L., R. B. Hornick, M. 3. Snyder, J. P. Libonati, S. B. Formal, and E. J. Gangarosa. 1972. Immunity in shigellosis. H. Protection induced by oral live vaccine or primary infection. J Infect Dis. 125:12-6.

11. Ertesvag, H., B. Doseth, B. Larsen, G. Skjak-Braek, and S. Valla. 1994. Cloning and expression of an *Azotobacter vinelandii* mannuronan C-5-epimerase gene. J Bacteriol. 176:2846-53.

12. Formal, S. B., L. S. Baron, D. J. Kopecko, O. Washington, C. Powell, and C. A. Life. 1981. Construction of a potential bivalent vaccine strain: introduction of *Shigella sonnei* form I antigen genes into the galE *Salmonella typhi* Ty21a typhoid vaccine strain. Infect Immun. 34:746-50.

13. Franklin, M. J., C. E. Chitnis, P. Gacesa, A. Sonesson, D. C. White, and D. E. Ohman. 1994. *Pseudomonas aeruginosa* AlgG is a polymer level alginate C5-mannuronan epimerase. J Bacteriol. 176:1821-30.

14. Germanier, R., and E. Furer. 1975. Isolation and characterization of Gal E mutant Ty 21a of *Salmonella typhi*: a candidate strain for a live, oral typhoid vaccine. J Infect Dis. 131:553-8.

15. Goldman, R. C., D. White, F. Orskov, I. Orskov, P. D. Rick, M. S. Lewis, A. K. Bhattacharjee, and L. Leive. 1982. A surface polysaccharide of *Escherichia coli* 0111 contains O-antigen and inhibits agglutination of cells by O-antiserum. J Bacteriol. 151:1210-21.

16. Gotschlich, E. C. 1994. Genetic locus for the biosynthesis of the variable portion of *Neisseria gonorrhoeae* lipooligosaccharide. J Exp Med. 180:2181-90.

17. Hartman, A. B., M. M. Ruiz, and C. L. Schultz. 1991. Molecular analysis of variant plasmid forms of a bivalent *Salmonella typhi-Shigella sonnei* vaccine strain. J Clin Microbiol. 29:27-32.

18. Hartman, A. B., and M. M. Venkatesan. 1998. Construction of a stable attenuated *Shigella sonnei* DeltavirG vaccine strain, WRSS1, and protective efficacy and immunogenicity in the guinea pig keratoconjunctivitis model. Infect Immun. 66:4572-6.

19. Hashimoto, Y., N. Li, H. Yokoyama, and T. Ezaki. 1993. Complete nucleotide sequence and molecular characterization of ViaB region encoding Vi antigen in *Salmonella typhi*. J Bacteriol. 175:4456-65.

20. Heinrichs, D. E., M. A. Monteiro, M. B. Perry, and C. Whitfield. 1998. The assembly system for the lipopolysaccharide R2 core-type of *Escherichia coli* is a hybrid of those found in *Escherichia coli* K-12 and *Salmonella enterica*. Structure and function of the R2 WaaK and WaaL homologs. J Biol Chem. 273:8849-59.

21. Herrington, D. A., L. Van de Verg, S. B. Formal, T. L. Hale, B. D. Tall, S. J. Cryz, E. C. Tramont, and M. M. Levine. 1990. Studies in volunteers to evaluate candidate *Shigella* vaccines: further experience with a bivalent *Salmonella typhi-Shigella sonnei* vaccine and protection conferred by previous *Shigella sonnei* disease. Vaccine. 8353-7.

22. Hitchcock, P. J., and T. M. Brown. 1983. Morphological heterogeneity among *Salmonella* lipopolysaccharide chemotypes in silver-stained polyacrylamide gels. J Bacteriol. 154:269-77.

23. Hohn, B., and J. Collins. 1980. A small cosmid for efficient cloning of large DNA fragments. Gene. 11:291-8.

24. Hornig, H. S., and M. M. Venkatesan. 1998. Genetic analysis of *Shigella sonnei* form I antigen: identification of a novel IS630 as an essential element for the form I antigen expression. Microb Pathog. 25:165-73.

25. Kenne, L., B. Lindberg, K. Petersson, E. Katzenellenbogen, and E. Romanowska. 1980. Structural studies of the 0-specific side-chains of the *Shigella sonnei* phase I lipopolysaccharide. Carbohydr. Res. 78:119-26.

26. Kopecko, D. J., O. Washington, and S. B. Formal. 1980. Genetic and physical evidence for plasmid control of *Shigella sonnei* form 1 cell surface antigen. Infect Immun. 29:207-14.

27. Kotloff, K. L., J. P. Winickoff, B. Ivanoff, J. D. Clemens, D. L. Swerdlow, P. J. Sansonetti, G. K. Adak, and M. M. Levine. 1999. Global burden of *Shigella* infections: implications for vaccine development and implementation of control strategies. Bull World Health Organ. 77:651-66.

28. Laemmli, U. K. 1970. Cleavage of structural proteins during the assembly of the head of bacteriophage T4. Nature. 227:680-5.

29. Lai, V., L. Wang, and P. R. Reeves. 1998. *Escherichia coli* clone *Sonnei* (*Shigella sonnei*) had a chromosomal O-antigen gene cluster prior to gaining its current plasmid-borne O-antigen genes. J Bacteriol. 180:2983-6.

30. Li, J., A. Hagner-McWhirter, L. Kjellen, J. Palgi, M. Jalkanen, and U. Lindahl. 1997. Biosynthesis of heparin/heparan sulfate. cDNA cloning and expression of D-glucuronyl C5-epimerase from bovine lung. J Biol Chem. 272:28158-63.

31. Matsutani, S., and E. Ohtsubo. 1990. Complete sequence of IS629. Nucleic Acids Res. 18:1899.

32. Mead, P. S., L. Slutsker, V. Dietz, L. F. McCaig, J. S. Bresee, C. Shapiro, P. M. Griffin, and R. V. Tauxe. 1999. Food-related illness and death in the United States. Emerg Infect Dis. 5:607-625.

33. Mendiola, M. V., Y. Jubete, and F. de la Cruz. 1992. DNA sequence of IS91 and identification of the transposase gene. J Bacteriol. 174:1345-51.

34. Paulsen, I. T., J. H. Park, P. S. Choi, and M. H. Saier, Jr. 1997. A family of gram-negative bacterial outer membrane factors that function in the export of proteins, carbohydrates, drugs and heavy metals from gram-negative bacteria. FEMS Microbiol Lett. 156:1-8.

35. Sambrook, J., E. F. Fritsch, and T. Maniatis. 1989. In Molecular Cloning: A Laboratory Manual. 2nd edition.

36. Sansonetti, P. J., D. J. Kopecko, and S. B. Formal. 1981. *Shigella sonnei* plasmids: evidence that a large plasmid is necessary for virulence. Infect Immun. 34:75-83.

37. Seid, R. C., Jr., D. J. Kopecko, J. C. Sadoff, H. Schneider, L. S. Baron, and S. B. Formal. 1984. Unusual lipopolysaccharide antigens of a *Salmonella typhi* oral vaccine strain expressing the *Shigella sonnei* form I antigen. J Biol Chem. 259:9028-34.

38. Shepherd, J. G., L. Wang, and P. R. Reeves. 2000. Comparison of O-antigen gene clusters of *Escherichia coli* (*Shigella*) *sonnei* and *Plesiomonas shigelloides* O17*: sonnei* gained its current plasmid-borne O-antigen genes from *P. shigelloides* in a recent event. Infect Immun. 68:6056-61.

39. Stroeher, U. H., L. E. Karageorgos, M. H. Brown, R. Morona, and P. A. Manning. 1995. A putative pathway for perosamine biosynthesis is the first function encoded within the rib region of *Vibrio cholerae* O1. Gene. 166:33-42.

40. Van de Verg, L., D. A. Herrington, J. R. Murphy, S. S. Wasserman, S. B. Formal, and M. M. Levine. 1990. Specific immunoglobulin A-secreting cells in peripheral blood of humans following oral immunization with a bivalent *Salmonella typhi-Shigella sonnei* vaccine or infection by pathogenic *S. sonnei*. Infect Immun. 58:2002-4.

41. Vieira, J., and J. Messing. 1982. The pUC plasmids, an M13mp 7-derived system for insertion mutagenesis and sequencing with synthetic universal primers. Gene. 19:259-68.

42. Viret, J. F., S. J. Cryz, Jr., A. B. Lang, and D. Favre. 1993. Molecular cloning and characterization of the genetic determinants that express the complete *Shigella* serotype D (*Shigella sonnei*) lipopolysaccharide in heterologous live attenuated vaccine strains. Mol Microbiol. 7:239-52.

43. Wang, L., S. Jensen, R. Hallman, and P. R. Reeves. 1998. Expression of the O antigen gene cluster is regulated by RfaH through the JUMPstart sequence. FEMS Microbiol Lett. 165:201-6.

44. Whitfield, C., and I. S. Roberts. 1999. Structure, assembly and regulation of expression of capsules in *Escherichia coli*. Mol Microbiol. 31:1307-19.

45. Yoshida, Y., N. Okamura, J. Kato, and H. Watanabe. 1991. Molecular cloning and characterization of form I antigen genes of *Shigella sonnei*. J Gen Microbiol 137:867-74.

46. Zhao, X., C. Creuzenet, M. Belanger, E. Egbosimba, J. Li, and J. S. Lam. 2000. WbpO, a UDP-N-Acetyl-D-galactosamine dehydrogenase from *Pseudomonas aeruginosa* serotype 06. J Biol Chem. 275:33252-9.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. An immunoprotective composition comprising an attenuated bacterium expressing a first antigen useful for inducing an immunoprotective response against *Shigella sonnei* (*S. sonnei*) O-polysaccharide and a second antigen useful for inducing an additional immunoprotective response against *S. sonnei* and/or at least one bacterial strain selected from the group consisting of *Shigella flexneri, Shigella dysenteriae, Shigella boydi, Salmonella typhi, Escherichia coli, Vibrio cholerae*, and *Yersinia*, the second antigen comprising a heterologous surface protein antigen expressed in bacteria selected from the group consisting of *S. sonnei, Shigella flexneri, Shigella dysenteriae, Shigella boydi, Salmonella typhi, Escherichia coli, Vibrio cholerae*, and *Yersinia,* wherein the first antigen is the O-polysaccharide produced from enzymes encoded by an expression cassette comprising a polynucleotide fragment encoding the genes wbgT, wbgU, wzx, wzy, wbgV, wbgW, wbgX, wbgY, and wbgZ isolated from the *S. sonnei* rfb/rfc gene cluster or the related *Plesiomonas shigelloides* (*P. shigelloides*) O17 rfb/rfc gene cluster operably linked to transcriptional promoter and termination signals, wherein the expression cassette does not include sequences that naturally flank the rfb/rfc gene cluster, and wherein the second antigen is a heterologous surface protein antigen encoded by genes carried by the at least one bacterial strain.

2. A multivalent vaccine comprising the composition of claim 1, wherein the vaccine protects against more than a single disease agent.

3. An immunoprotective composition comprising more than one attenuated Ty21a strains, wherein each strain expresses one heterologous LPS O-antigen, and one strain additionally expresses a protein surface antigen that will cross-protect against more than one *Shigella* serotype strain.

* * * * *

SEQUENCE LISTING

```
<160> NUMBER OF SEQ ID NOS: 22

<210> SEQ ID NO 1
<211> LENGTH: 15690
<212> TYPE: DNA
<213> ORGANISM: Shigella sonnei
<220> FEATURE:
<221> NAME/KEY: misc_feature
<223> OTHER INFORMATION: 15.7 kb HindIII fragment from AF294823 (SEQ ID
      NO:7 positions 1310-16999) encoding Shigella sonnei O antigen gene
      cluster

<400> SEQUENCE: 1

aagcttgatc aaatagctca tattcagcga gatttaacaa ctgcggaaca agccggaatc     60

attgattatc gctctagcaa aggcggcttc gataatgcgc aaagtagcta taagttcttg    120

ctcggcgaaa aactgttatc agcagagcta aaagcaacta aagatgcgcc aattatttac    180

ccatttagat attacgaagt gaaacgtcaa attgatgagt tagaaggaat gttacgcgat    240

aacattcagg cgcaagcata tcgatatcaa atgaagccat ctgagccagt tataaaagac    300

aaacccaaca aagcattaat tttgattctt ggtgcattac caggggcaat gtttgctata    360

gttggtacat tagtttatgc gacattaaaa gataaaacca agttagatta aactgggtta    420

cgtattgttg tgtcaatgcg aaatagatgt tctatgtgca ctttatgatg gataagaaaa    480

tgaaattcga tactttgaat gcgaaaattg ggattatagg ccttggttat gttggattgc    540

ctcttgctgt tgagtttgga aagaaagtaa cgacgattgg atttgatatt aataagtctc    600

gtattgatga attacgaaat ggtcacgata gtacattaga gtgctcaaat ttagagttgt    660

tagaagcaac taaattgacg tacgcctgtt cattagatgc actaaaagag tgtaatgtat    720

ttattgtaac tgttccaact ccaattgata aacataaaca gccagatcta acacctctaa    780

ttaaagcatc tgaaacattg ggtaagataa taaagaaagg cgatgttatt atttatgagt    840

caacagttta ccctggagcg acagaagaag attgtatacc agttgtagag aaagtatcag    900

gtcttaagtt taatattgat ttttttgccg gttattcacc tgagcgtatt aatcctgggg    960

ataaagagca tcgtgtaact aatatcctta aggtgaccag tggatctaca ccggatgttg   1020

ctgagtatgt agatcagcta tataaattaa taattactgt cggtacgcat aaagcatcat   1080

cgataaaagt agcagaggct gcaaaagtaa ttgaaaacac gcagcgagat gtcaatattg   1140

cattgattaa tgagttatct attatattta ataagttagg gattgatacc ttagaggttc   1200

ttgaggctgc aggtacgaag tggaattttt tacctttttag gcccggttta gtaggtggcc   1260

actgtatagg tgtagatcct tattatctta cacataaagc gcaaagtgtc ggctatcatc   1320

cggagatgat tttagccgga cgtcgtttaa atgatagtat ggggcagtat gtcgtttccc   1380

agttagtcaa aaaaatgttg aaacaacgga ttcaagttga aggggcgaat gtgttagtga   1440
```

```
tggggcttac atttaaagag aattgcccag atctacgaaa cactaaagtg attgatatta   1500
tttcagagtt aaaagaatac aatatcaata tagatattat agatccatgg tgttctaccg   1560
atgaggcaca acatgaatat ggattaactt tatgtgaaga tcctaaagtt aatcattatg   1620
atgcaataat tatcgctgtt gcacacaatg agtttcgcga gatgggagag agcgctattc   1680
gtgcattagg taaagacgag cacgttttgt tcgatttaaa atatgtgctt gataaaaaaa   1740
gtatcgatat gcgcttgtaa gagtgattaa aaaaatcaaa tcctctttga tatgatacac   1800
ctcagcattt tatgctaggt ttagcacttg attaatatac atggatattt atatgtctcg   1860
ctatgaagag attacacagc agttaatttt ttcaccgaaa acttggttaa ttactggtgt   1920
cgctggcttt ataggatcaa atcttttaga aaagttactt aaattaaacc aggttgttat   1980
tgggttagat aacttttcca cgggacatca atataatctt gatgaagtta aaacattagt   2040
ttccactgaa cagtggagtc gattttgctt tatagaaggt gatattcgag atctcactac   2100
ctgtgagcaa gttatgaaag gtgttgatca tgtcttacat caggctgcgc taggttctgt   2160
acctcgttca attgttgatc ctataacaac caatgcaact aatattactg gatttttgaa   2220
tatcttacat gcggctaaaa atgcacaagt acaaagtttt acttatgctg catcaagctc   2280
aacttatgga gatcatcccg cactaccaaa agtagaggaa aacattggta atccactttc   2340
tccttatgca gttactaaat atgttaacga gatttatgct caggtatatg ctcgaacata   2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgatttttgt tatatagata atgttataca   2580
aatgaatata ttatctgcat tagcgaagga cagtgctaaa gataatatat ataatgttgc   2640
agttggtgat agaacaacgt taaatgaatt atctggttac atttatgatg agcttaattt   2700
aattcaccat atcgataaat tgagcattaa gtatagagag tttagatctg gagatgttag   2760
gcattctcag gctgatgtta ctaaggctat agatttacta aagtatagac caaatataaa   2820
aatcagagag ggattacgac tttcaatgcc gtggtatgtg agatttttaa aaggctaaat   2880
tatattaaca tgaataaata atctatttca cctctgttat taatgcaggg gtgaaaatcc   2940
atgtatttat tctaaatggt cagtgtatgt ttagaaaaat gattgatgca ggtggtacat   3000
ttttacttaa agcaatattt caaataggag tttttgttta tttcacacat gtgtcagata   3060
ttactacatt tggtattatt agttatgtgt ttactgttta ttggtttgtg cttaacttct   3120
ctgattatgg atttagaaca aaattagtga aagatatttc tgataatagt tattctgcat   3180
cagaattatt atcaagaagt gatggagtta aaacatatgt ttttttcttc atttttataa   3240
tcttcatgtt ttattcttat gtttctgatt caatttcatt aactctgctt gtttatattt   3300
catctgcata ttttgtttgt atttcaagtg gtagatttag cttgctacag gctgttggtc   3360
ggtttagatg tgaattatat ataaatatct actcaacaat tatatatatt gggtgtaatt   3420
tatttttatc tctgtttatc gaacctctat attatagtgc gatatcaata ttcatatact   3480
caatttcgct tttggttttc tcatcacata aatgcaatgt gccatgtttt catataaaaa   3540
gaccaagtat tttagtttat aaagattttt tggatgcaac tccgttcgct attctggtgt   3600
tactaaatgt tgttttatct agtattgacc tttttatatt aaaagaatat ttctcttata   3660
atagtgttgc tatatatcag gtggtaacta gggttaatac cggtctaata atagtgttta   3720
atgttattta tactgtttta ttgccttcat tttcttatta tctgaaaaat tctgaatggg   3780
```

```
gtaatataag gaaattacaa cgatatatat cactgttagt cttattacta tgtttatgct   3840
attatttttt tggcatctat ttcgtaggga tattgtttgg tgatgagtat aaggtaatat   3900
cttctgcaac atttttgata atgtttatgg ctcttattaa atataatttt tggctaataa   3960
atgaacttta tcttgtgtgt agtggaaatc aaagcgagcg agttaaatcg tattgtattg   4020
gtgtggtcat ttcaatggcg gttttctttt attttatacc tcggtatgga tggagtgggg   4080
cggtttttgg aagtgccatt gcaacattag taattggaat attttatatt atttctgtga   4140
aaaaagattg tgggaaaatt cttcatgata agtattcact aatgatgatc tttgtcccaa   4200
ttttctttta ttttattatt aatggtcagc agcggttgtt atattaatat gttgtggttt   4260
tatatcgttc cattaatatg tttagactcg attggaagcc taataaaggt taagtatgtt   4320
aatataccta tatcctgtac ttttgttatt taatatcctt ccggtttttt tttatggaca   4380
aatgaactct gatttagagc gttttttttgg agttcctatt ggctatattc cagatctaat   4440
attttatttc tttgttgttt taacatctat aataacgttg aggtttcacg tttctctgtg   4500
gacaaagaaa ttattatttt taggcatcat attcctgatt tatatcagca ttcagatgtt   4560
gttgttatca gcggatatat caggtgtcgt aattttatta tcgttttttt ctaattttat   4620
agctttggtt cttttggtgt cattttgcat tggtaaagat gagctttatt taactcattc   4680
ggttagaaat ataaatgttg taatgtgttt tggtattatc tgtggagttg taaaattatt   4740
tattggttat tctgaagata gtaattttat agtttattta aatagaaatg ccaccgcaat   4800
tatagtagtg tgcttttatt gtgtatattc atacttttat cgtggtcgaa agtcttggta   4860
tgtctcatct gtattgtact ctctgttctt tctttttctg gatagccgag caggaataat   4920
atcatttgct atatcgttgt tttttgtttt tcttcagtta acaaagaagg aaaagttatt   4980
aatatcattg ttttttgttc ctcttctaac tttaggtatt tcttttactg atataggcac   5040
tcgtcttgaa cgaatgctgt cttcgtcaca ggttatattc tctggtggta acactcttac   5100
aaaaagtcag aatgattatc gtcgagttga gttagtattt attggggttg atgttttaaa   5160
agaaaattat ttaattggca ctggattagg tgttgcaaat tatgtaaagg ctatagataa   5220
aaagttttta ggaagtacca actttgggtt ggcgcataat ttttatttat cttattcggc   5280
tcagttaggg attattggtt ttattttgct tatttctgta ttttatataa tgctgtctcc   5340
aatttttaaa tgcggagggt atattggtaa aggatgcgtt tttgctttgg ctttctatgt   5400
ctttttaat gagtatatat tgacgccagc gatatatatt tatatttcta ttttttttatc   5460
ggtggttttt atacgtaatt ctaaatagct gcgcggaata gtagatcact ttgagggaac   5520
ttagcccgga ttgtgcgatc tgatcaatcg ccaaatcaaa acaaatcacc aaccggactg   5580
agcaatgccg atcatagcac caatttcccg tgacgaacga cgcctgatgc agaaagccat   5640
ccataaaaca cacgataaaa attatgcccg cagactgact gccatgctga tgctgcaccg   5700
gggcgaccgt gtcagcgacg ttgccagaac gctctgctgc gcccgttcct ctgttggacg   5760
ctggattaac tggttcacgc agtcgggtgt tgagggactg aaatcattac ctgccgggcg   5820
tgcccgtcgc tggccgtttg agcatatctg cacactgtta cgtgagctgg taaaacattc   5880
tcccggcgac tttggctacc agcgttcacg ctggagtaca gaactgctgg caataaaaat   5940
caatgagata accggttgcc agttaaatgc cggaaccgtt cgccgctggt tgccgtctgc   6000
ggggattgtg tggcgaaggg ctgcgccaac tctgcgtatc cgtgacccgc ataaagatga   6060
aaagatggca gcaatccata aagcactgga cgaatgcagc gcagagcatc cggtctttta   6120
tgaagatgaa gtggatatcc atcttaatcc caaaatcggt gcggactggc aactgcgcgg   6180
```

```
acagcaaaaa cgggtggtca cgccgggaca gaatgaaaaa tattatctgg ccggagcgct   6240
gcacagcggg acaggtaaag tcagctgtgt gggcggcaac agcaaaagtt cggcgctgtt   6300
catcagcctg ctgaagcggc ttaaagcgac ataccgtcgg gcgaaaacca tcacgctgat   6360
cgtggacaac tacattatcc acaaaagccg ggaaacacag agctggctga aggagaaccc   6420
gaagttcagg gtcatttatc agccggttta ctcgccatgg atgaatcatg ttgaacggct   6480
atggcaggca cttcacgaca caataacgcg taatcatcag tgcagctcaa tgtggcaact   6540
gttgaaaaaa gttcgccatt ttatggaaac cgtcagccca ttccccggag gcaaacatgg   6600
gctggcaaaa gtgtagcggt attaagcgca gctatttagg atgagaatat gttgttagaa   6660
tatgttgaaa gaaaaatttc cttagccttg agtaagtatc ctaaggtaag ggatgttatt   6720
aagttctttt atttatatat cgcatcatta ttcggaatta ttttgaataa aaataagacg   6780
gttattcaat caaaaatata cgagatttca attgatgatt ctgaagaatc attttttggc   6840
tattatgacc atagtccaat gagctctaat gggcggtacg tattgttcca ctctagtgcg   6900
tttagcacta aacgacatcc aaagaaagtt aagtatatat ctatttgcgt aaaagacctt   6960
cttaataaca aagtttataa gctatatgat acgcgagcat ttaattggca gcagggaagc   7020
cgattaatgt ggattgatga tgacaatata atttttaatg actatgaaaa taatggatac   7080
attagtgttg tctattcttt gtctttgatg aaggttataa aaaaaataaa ctatccgatt   7140
tatgatgtga ataattacaa ggctgtgacg ttagatttct catggctggc taaatatgat   7200
agcgattatg gttattataa taaaaaatca ttttctacag atatttcaat cattaatttg   7260
aatacggggg gaatagaatt atttttatcc ttagacgaaa tgctaaagag aactaatttt   7320
aaatgtaata ttgatgttga acatgtggtc aatcatttta tgtttgctcc cgatggacgt   7380
tccgttatgt tcatacatcg atactataca cctaaaggaa agcgtgaaag gttaatacat   7440
tggaatttaa taaatgataa tgttcgagtc ctaataaatg aatcgattat tagtcattgt   7500
tgttggaatg ggaatgatga aattataggt ttttttggtg cagaaataga ttcgctaaat   7560
tattatagat tgtcaattga atcctgtaat acagagaaat tgttttttga tgcaagaaaa   7620
tattctgatg gacatcctac tatagttcat aatagatata ttatatctga tacttaccca   7680
gataaaaata gaattaaaaa gttgtttgtt tatgaccttg tcaaaaatga ttatcgcgag   7740
cttggattat tttatgagtc aatgagtttt ttttcttatt ctcgatgtga cttacatcca   7800
aggatctcgg ttgataatag atttttgttt gttgattcag ttcactcagg gaaaagaaaa   7860
ctatatttta tgaggagtgg tatttgtgag tgatgttcta gtatctttaa ttatagtttg   7920
ctttaatgca gagaagtata ttgaaaaatc tcttttggca tttattaatc aagatgttgg   7980
attagataaa tttgaattga ttattgtaga tggggattca tctgataata caatatctat   8040
tgttcaggat gttttttcta aacatagcaa cattaagcat aaaattatca ataataaaaa   8100
aagaactctt gctacgggtt ggaatattgg ggtgctagaa gctaatggta agtttgtgtg   8160
tagagttgat gcacatagtg atattccaaa taactatata tctaaattat tagatgatta   8220
ttttaatatt atgcagtttg atgatagcgt tgttggtgtt ggaggtgtat taactaattc   8280
ttataaaact aagtttggtt caattgtagc ggatttttat gcatcgaaat ttggtgttgg   8340
taattctcca tttaggtgcg tagacaaaaa taatcgacta aaaaaaacag atacagctgt   8400
ctttgcttta tataataaag atgtgttttt tgatgttgga ctttttaatg aagtattaga   8460
tagaaatcaa gatattgatt ttcataagag agttttaagc aataatttgt cattatatac   8520
```

```
agataatagt ttatttgttg agtattatgt tagagataat tttaaagatt tcataaagaa   8580
aggttttctt gatggttttt gggttgttat gtctggagca tattatttta gacatatagt   8640
gccacttttt tttgttttgt atttaattgt atctttttct cttttctttg ctactggtga   8700
ttatatatat ttatcttttt tatttttta ttttcttatt tctattttgt tttcaattcg   8760
agatgggcga agttttatag gtagagtatt tcttcctttt atatttttgt cttatcatat   8820
ttcttatgga tgtggatcgt tattatcttt tttgaaaagg tattttaaat gaaaaatttt   8880
attcctttg cgttacctga aattggcgaa gaagaaattg cagaggtaat tgactcttta   8940
cgttcaggtt ggattacgac aggtcctaag gctaagcaat ttgaacaaga attttctaat   9000
tacctaggag cgaacgttca atcattagct gttaactctg ctacgtcggg cttacatttg   9060
gctcttgaag ctgttggcgt aaagccggga gaccaagtta ttgtcccatc atatacattc   9120
actgctactg ccgaaattgt caggtacctt ggtgctgatc ctgtaattgt tgatgtagat   9180
cgtaaaacat ttaatatatc agttgatgcc attgagaagg ctattactaa tgaaacaaag   9240
gcgattattc cagtacactt cgctggatta gcttgtgaca tggattcaat cttatcaatt   9300
gctaaaaaat atgacctaaa ggttgtcgag gatgccgctc atgcatttcc tacaacatat   9360
aaaggaagta agataggaac gcttgattca gatgctacgg tttttagctt ctacgccaat   9420
aaaactatga caaccggtga aggcggaatg gttgtttcaa aaaataaaga tataattgag   9480
cgttgtaagg taatgcgttt acatggaatc agtcgtgacg cttttgaccg gtaccagtct   9540
aaaactcctt cttggtttta tgaggttgta gctccagggt ttaaatacaa tatgcctgat   9600
atctgtgcgg caatcggtat tcatcaactt agaaagatcg atgattttca gaaaaaacgt   9660
caacgaatgg caaaaattta cgatgatgcg ttaaaagaat tgccacttga attgcctgaa   9720
tggcctacta atgctagtga tattcatgct tggcatctat atcctatccg cttaaaaact   9780
gattcggcta ttaatcgcga tgattttatt aagaagttat cagatcttgg aattggttgt   9840
tctgtccatt ttataccgtt gcataagcaa ccggtttggc gtgatacata taatttgaac   9900
gccagtgact ttccagtttc tgaggagtgt tatttaaatg aaatatctat tcctctttat   9960
actaaaatga cggatcaaga tcagttgttc gttatcaaat cgattagaca attatttatg  10020
taatggtatt ttatattaaa tgaaacgtat ttttgatgtt atcgtggcag gcttaggcct  10080
gctttttcta tttcctgttt ttatcattgt gtcaatgtta attgttgctg attctaaagg  10140
gggggttttt tttaggcagt atagagttgg gagatttggg aaagatttta ggatacataa  10200
atttagaacg atgtttatcg attcagaaaa aaaaggacgg ataacagttg gtcaagatgc  10260
tcgggtaacc agagttggat ggtatttacg gaagtacaaa atcgatgagc ttcctcaatt  10320
gatagatgtt ctttctggaa caatgagttt ggttggccca agaccggaag tgagggagtt  10380
tattgatgag tatcctgatg atataaggga aaaagtttta tcggttaggc cagggataac  10440
tgacttagca tctatagaaa tggtagatga aaatgagatt ttgtctagtt atgatgaccc  10500
acgtagggct tatatagata taattcttcc aatcaagcaa agatattatt tagattatgt  10560
tgctaacaat tcagtaaagt atgattgtgt gataatttgg aaaactatta ttaagatttt  10620
gtcgcgataa taaggtagtg taggatgatt gatagaatat tggagctgcc aagaattgtt  10680
aagagaggta tcatcatctg cattgatgta gttatggtga tattctcatt ttggttgtct  10740
tattggttga ggcttgatga gcaaacggct tttcttagtg caccgatgtg gtttgctgca  10800
gctattctta ccatatttac cgtgtttata tttatcagga ttgggcttta tcgggcagtc  10860
ttacggtatg ttagtgcaaa gataatgttg ctaataccag ttggtattct ggcctcaacg  10920
```

```
ttatctcttg tcgttatatc atattcgcta tccataatgt tgccgcgcac tgttgtcgga  10980
atttattttt tggttttact tttactgaca tcaggctcta gattgctttt tagaatgata  11040
cttaactatg gagttaaggg tagtgcgcct gttttgattt atggcgctgg tgaatctggc  11100
cgacaattat tgccagcatt aatgcaggca aaagaatatt ttcctgtggc atttgtggat  11160
gataatcctc gcttgcataa ggctgtcatt catggtgtaa cagtttatcc ctcggataaa  11220
ctgagttacc ttgtagatcg ctatggtata aagaaaattc ttttggcgat gccgagcgtc  11280
agtaagtcac aaaggcagaa agtgattact cgtttagagc atctaccgtg tgaagttctc  11340
tctattccgg gtatggtcga tttagtcgaa ggtcgagcac aaatcagtaa tctaaaaaaa  11400
gtatcgattg atgacttact aggtcgtgat ccggttgctc ctgatgccaa attgatggcc  11460
gaaaacatta ctggcaaagc cgttatggtc actggggcgg gaggctcgat cggctctgag  11520
ctttgtcgtc aaattgttcg atataagccg gccaaattgg ttctatttga actgtctgaa  11580
tatgccctct acgctattga gaaagagctc tcggcgctgt gcgacaaaga agttttgaat  11640
gttccagtga tccctctgtt gggctcggtg cagcgtcaga atcgcttaca gatggtgatg  11700
aagtcctttg gtattcaaac ggtttatcat gcggccgctt ataaacatgt gcctctggtt  11760
gagcataatg tggtggaagg ggtacgtaat aacgtgtttg gtaccttgta ctgcgctgag  11820
tcagcgatcg aaagtggcgt tgaaactttt gtgttgattt ccaccgataa agcggtgcgc  11880
ccgaccaaca ctatggggac aactaagcgt ctggccgaat tggtattgca ggctttgtct  11940
gcacggcaaa gccaaactcg cttttgtatg gtgcgatttg gtaatgtact cggttcttcg  12000
ggctctgtcg tgccgttgtt tgaaaaacag attgcccaag gtgggccagt taccttgact  12060
catcgtgaca ttattcgcta tttcatgaca attccggaag catcacagtt ggtgattcaa  12120
gcgggggcga tggggcatgg cggcgatgtc tttgtcttag acatgggcga tccggtcaag  12180
atttatgact tagccaaacg catgatccgg ttaagtggct tgagtgtacg ggatgataaa  12240
aatccagatg gcgatattgc cattgaagtt acgggattac gtccagggga gaaactgtat  12300
gaagaattac tgattggtga ttcagttcaa ggtacctctc atccacgaat tatgacggcc  12360
aacgaagtga tgctaccgtg gcaggatcta tcgctcttac ttaaagagct ggatcaagct  12420
tgtcatgact ttgatcatga gcgaattcgc agtttgttgt tacaagcacc agcggcattc  12480
aatccaactg atgatatttg cgatctagtt tggcagcaga aaaaatcgct gttatcacaa  12540
gcgagcaatg tcattcgcct gtgattgctt aggtttaacc ttccacacca attcttcacc  12600
tctcttacaa atccccgcta ggcggtacat cgtgaccgcc tttagcctga tgcctgctct  12660
ttaacaaaca ggacatcagt gtatgtttaa accttttagc gccgaatttt tcggcacttt  12720
ctggctggtt ctgggtggct gtggtagcgc cttgatctct gctgctttcc cacagttagg  12780
tataggcttt ttgggcgtgg cgttggcgtt tggtctgaca gtagtcacca tggcttatgc  12840
ggtcgggcac atctctggtg cgcattttaa ccccgcggtg accttgggtc tgtgggccgg  12900
tggacgcttc ccagcagcgc gcgtgttacc ttacattatc gctcaggtta tcggcggtat  12960
tgccgctgcg gcagtgctgt atggtatcgc cagcggtaag gctgggtttg atgcgacaac  13020
cagcggtttt gcggctaatg gttatggcct ccattcacct ggcggctatg cgttaagcgc  13080
ctgtatgctg agcgagtttg tcctcagtgc gttttttgtc cggagcgaca gaaaaacgcg  13140
ctcctgcggg ctttgcgcca ctggcgattg gtctggtaat caccccgtaa attaaccagc  13200
gtcaaaagta gaattttctc gtaccataaa cgcaggagat tctttatgca aacatcaaaa  13260
```

```
tttaccgaca agcaaatcat ggcgatcctc aaatgaaccc ccccgggaat cctggagact  13320
aaacttcctg agaaagaggt aaacaggatg actaaaaata ctcgtttttc ccccgaagtc  13380
cgtcaacggg cagtccgtat ggttctggaa agtcagggcg aatatgactc acaatgggcg  13440
acaatttgtt ccattgctcc aaagattggc tgtacgccgg agactctgcg tgtccgggtt  13500
cgccagtatg agcgggatac cgggggcggt gatggagggc tcaccaccgc tgaacgtcag  13560
cgtctgaaag agctggagcg tgaaaatcgt gaactgcgcc gcagtaacga tatccttcgc  13620
caagcttccg cttattttgc gaaggcggag ttcgaccgcc tctggaaaaa atgatgccac  13680
tgctggataa gctgcgtgag cagtacgggg tcggaccgct atgcagcgaa ctgcatattg  13740
ccccgtcaac gtattaggga tttgaagccc aaccgtacga aaacgtacgc taagttcatt  13800
tcttgaacaa cctggctgac tctatgtatt tgtacagcgt tggcctcgat atccccatca  13860
acacacaaat ctgcgcaact gtatgttttt tctcgttata gagttgaaca gcaagggcct  13920
gtttatcctt actcagtgtt ttcggcctgc cgcccttacg tcctctggct cgtgctgctt  13980
gaagcccgac ctgagttctc tctcttgtca ggttgcgttc atcgatagga attaaaaccc  14040
caaaaagatt aaaaaaacac cacaaaacgg atgtttcttc aacaccactt ttgctccata  14100
tgaacggaac cgacgattaa actggatggc tctgattgat tcagggtatg aatggcggtt  14160
ttttgctccg tttccctcaa aatggacgca acttcccctc tgcggctctc agccgcacca  14220
ccgcatccgg gccaagcagc tcatgcatca ggacctgctc tgccagacgg tagccccgct  14280
tcagccccgt aaaacgcatc tgactcccgc acagcacgca cttcagcggg tcaaccttca  14340
gtaacctctg atacatccct ctccaggtga tttgcatcgc cgtttttctc actgtctccg  14400
ttatgatgta caccacttct tccagtaacc gccgtttcgc cggactcaaa aaaccgtagt  14460
acctcaccat acggaacccc ttatccgcca catgccagga gaacctttcc atgaactcat  14520
ctccactcat caacaggtat tcttcccgtt ttgttcggtg actgttgtaa cgcagaccga  14580
tttcatcctg accggcataa tgctccagac gactcatcgg cactggtggc tttttcaggt  14640
aagagccaaa gtacaccgcc acatgggtgg cattatccat cacccgggat acgttgacat  14700
tccagccacg gcggtaatgc gtgtccagga agcgattcca ttcccgttta ctgcttcctt  14760
ctgctgccag cgcatccggc atcaccaggt cagggtattt ccgtgacagc aaccgtgtta  14820
tccggtagcg ccacatgctc atcaccttac gggcgtaaaa atgaagattt ttccaggtgt  14880
ggcccgacgt cacaccaccg gcagttgtcg ataaatggat atgcggatgc cactgctggt  14940
cacgccccca tgtgtggatc accgtgaata tccccgactc cacatctgcc tgatggcaga  15000
tttccagtat cacatccgct gcaatgcggc tcatctctgt cagtaaccac cggttgtgga  15060
acaccaggga ccagtactgg cagggaagtg tgaacacaat atgctgccac gggcagtcgg  15120
ggaccaggct cagcagatac tgtatccact gtgcgccagc cttcaccccg cagtgcgggc  15180
aggagcggct tttacaccgg aagcagacct tttttgtatg gcaacagtcc ggtgatgaac  15240
agcaccactg tgtatacccc atcagtgtgg tcccgcacgc catgattttg gtcaccgact  15300
caatcaccac cggacgtact gccccttccg gctgcttctc cagccagtta agccagcggt  15360
ttccctgctg aaagatatcg gcaaaacggg gaagcatcag aagggcgggg cgactccgtc  15420
cggccagtga accgtgccac actccgggca gtacataccg ccggcgctga taccggaaag  15480
aatggtcgca aattcccgct ccgtgcagcg ggcgatttcc ggataccctt cgtcatcaac  15540
acgtacaaac cagaagacca gctttttgtt tcccgcatcc acaaagaacg gaatattcag  15600
gtctgcgcag cattcaacgg catcgtcaaa actatcaaag cgcagaactt ctgcgtcttc  15660
```

```
ttcgtcaaaa aaatcatctt cgtgaagctt                                   15690


<210> SEQ ID NO 2
<211> LENGTH: 13627
<212> TYPE: DNA
<213> ORGANISM: Shigella sonnei
<220> FEATURE:
<221> NAME/KEY: misc_feature
<223> OTHER INFORMATION: 13.7 kb HindIII fragment from AF294823 (SEQ ID
      NO:7 positions 1310-14936) encoding Shigella sonnei O antigen gene
      cluster

<400> SEQUENCE: 2

aagcttgatc aaatagctca tattcagcga gatttaacaa ctgcggaaca agccggaatc     60

attgattatc gctctagcaa aggcggcttc gataatgcgc aaagtagcta taagttcttg    120

ctcggcgaaa aactgttatc agcagagcta aaagcaacta aagatgcgcc aattatttac    180

ccatttagat attacgaagt gaaacgtcaa attgatgagt tagaaggaat gttacgcgat    240

aacattcagg cgcaagcata tcgatatcaa atgaagccat ctgagccagt tataaaagac    300

aaacccaaca aagcattaat tttgattctt ggtgcattac caggggcaat gtttgctata    360

gttggtacat tagtttatgc gacattaaaa gataaaacca agttagatta aactgggtta    420

cgtattgttg tgtcaatgcg aaatagatgt tctatgtgca ctttatgatg gataagaaaa    480

tgaaattcga tactttgaat gcgaaaattg ggattatagg ccttggttat gttggattgc    540

ctcttgctgt tgagtttgga aagaaagtaa cgacgattgg atttgatatt aataagtctc    600

gtattgatga attacgaaat ggtcacgata gtacattaga gtgctcaaat ttagagttgt    660

tagaagcaac taaattgacg tacgcctgtt cattagatgc actaaaagag tgtaatgtat    720

ttattgtaac tgttccaact ccaattgata aacataaaca gccagatcta acacctctaa    780

ttaaagcatc tgaaacattg ggtaagataa taaagaaagg cgatgttatt atttatgagt    840

caacagttta ccctggagcg acagaagaag attgtatacc agttgtagag aaagtatcag    900

gtcttaagtt taatattgat ttttttgccg gttattcacc tgagcgtatt aatcctgggg    960

ataaagagca tcgtgtaact aatatcctta aggtgaccag tggatctaca ccggatgttg   1020

ctgagtatgt agatcagcta tataaattaa taattactgt cggtacgcat aaagcatcat   1080

cgataaaagt agcagaggct gcaaaagtaa ttgaaaacac gcagcgagat gtcaatattg   1140

cattgattaa tgagttatct attatattta ataagttagg gattgatacc ttagaggttc   1200

ttgaggctgc aggtacgaag tggaattttt taccttttag gcccggttta gtaggtggcc   1260

actgtatagg tgtagatcct tattatctta cacataaagc gcaaagtgtc ggctatcatc   1320

cggagatgat tttagccgga cgtcgtttaa atgatagtat ggggcagtat gtcgtttccc   1380

agttagtcaa aaaaatgttg aaacaacgga ttcaagttga aggggcgaat gtgttagtga   1440

tggggcttac atttaaagag aattgcccag atctacgaaa cactaaagtg attgatatta   1500

tttcagagtt aaaagaatac aatatcaata tagatattat agatccatgg tgttctaccg   1560

atgaggcaca acatgaatat ggattaactt tatgtgaaga tcctaaagtt aatcattatg   1620

atgcaataat tatcgctgtt gcacacaatg agtttcgcga gatgggagag agcgctattc   1680

gtgcattagg taaagacgag cacgttttgt tcgatttaaa atatgtgctt gataaaaaaa   1740

gtatcgatat gcgcttgtaa gagtgattaa aaaaatcaaa tcctctttga tatgatacac   1800

ctcagcattt tatgctaggt ttagcacttg attaatatac atggatattt atatgtctcg   1860

ctatgaagag attacacagc agttaatttt ttcaccgaaa acttggttaa ttactggtgt   1920
```

```
cgctggcttt ataggatcaa atcttttaga aaagttactt aaattaaacc aggttgttat   1980
tgggttagat aacttttcca cgggacatca atataatctt gatgaagtta aaacattagt   2040
ttccactgaa cagtggagtc gattttgctt tatagaaggt gatattcgag atctcactac   2100
ctgtgagcaa gttatgaaag gtgttgatca tgtcttacat caggctgcgc taggttctgt   2160
acctcgttca attgttgatc ctataacaac caatgcaact aatattactg gatttttgaa   2220
tatcttacat gcggctaaaa atgcacaagt acaaagtttt acttatgctg catcaagctc   2280
aacttatgga gatcatcccg cactaccaaa agtagaggaa aacattggta atccactttc   2340
tccttatgca gttactaaat atgttaacga gatttatgct caggtatatg ctcgaacata   2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgatttttgt tatatagata atgttataca   2580
aatgaatata ttatctgcat tagcgaagga cagtgctaaa gataatatat ataatgttgc   2640
agttggtgat agaacaacgt taaatgaatt atctggttac atttatgatg agcttaattt   2700
aattcaccat atcgataaat tgagcattaa gtatagagag tttagatctg gagatgttag   2760
gcattctcag gctgatgtta ctaaggctat agatttacta aagtatagac caaatataaa   2820
aatcagagag ggattacgac tttcaatgcc gtggtatgtg agatttttaa aaggctaaat   2880
tatattaaca tgaataaata atctatttca cctctgttat taatgcaggg gtgaaaatcc   2940
atgtatttat tctaaatggt cagtgtatgt ttagaaaaat gattgatgca ggtggtacat   3000
ttttacttaa agcaatattt caaataggag tttttgttta tttcacacat gtgtcagata   3060
ttactacatt tggtattatt agttatgtgt ttactgttta ttggtttgtg cttaacttct   3120
ctgattatgg atttagaaca aaattagtga aagatatttc tgataatagt tattctgcat   3180
cagaattatt atcaagaagt gatggagtta aaacatatgt ttttttcttc atttttataa   3240
tcttcatgtt ttattcttat gtttctgatt caatttcatt aactctgctt gtttatattt   3300
catctgcata ttttgtttgt atttcaagtg gtagatttag cttgctacag gctgttggtc   3360
ggtttagatg tgaattatat ataaatatct actcaacaat tatatatatt gggtgtaatt   3420
tatttttatc tctgtttatc gaacctctat attatagtgc gatatcaata ttcatatact   3480
caatttcgct tttggttttc tcatcacata aatgcaatgt gccatgtttt catataaaaa   3540
gaccaagtat tttagtttat aaagattttt tggatgcaac tccgttcgct attctggtgt   3600
tactaaatgt tgttttatct agtattgacc tttttatatt aaaagaatat ttctcttata   3660
atagtgttgc tatatatcag gtggtaacta gggttaatac cggtctaata atagtgttta   3720
atgttattta tactgtttta ttgccttcat tttcttatta tctgaaaaat tctgaatggg   3780
gtaatataag gaaattacaa cgatatatat cactgttagt cttattacta tgtttatgct   3840
attatttttt tggcatctat ttcgtaggga tattgtttgg tgatgagtat aaggtaatat   3900
cttctgcaac atttttgata atgtttatgg ctcttattaa atataatttt tggctaataa   3960
atgaacttta tcttgtgtgt agtggaaatc aaagcgagcg agttaaatcg tattgtattg   4020
gtgtggtcat ttcaatggcg gttttctttt attttatacc tcggtatgga tggagtgggg   4080
cggtttttgg aagtgccatt gcaacattag taattggaat attttatatt atttctgtga   4140
aaaaagattg tgggaaaatt cttcatgata agtattcact aatgatgatc tttgtcccaa   4200
ttttctttta ttttattatt aatggtcagc agcggttgtt atattaatat gttgtggttt   4260
```

```
tatatcgttc cattaatatg tttagactcg attggaagcc taataaaggt taagtatgtt   4320
aatataccta tatcctgtac ttttgttatt taatatcctt ccggtttttt tttatggaca   4380
aatgaactct gatttagagc gtttttttgg agttcctatt ggctatattc cagatctaat   4440
attttatttc tttgttgttt taacatctat aataacgttg aggtttcacg tttctctgtg   4500
gacaaagaaa ttattatttt taggcatcat attcctgatt tatatcagca ttcagatgtt   4560
gttgttatca gcggatatat caggtgtcgt aattttatta tcgttttttt ctaattttat   4620
agctttggtt cttttggtgt cattttgcat tggtaaagat gagctttatt taactcattc   4680
ggttagaaat ataaatgttg taatgtgttt tggtattatc tgtggagttg taaaattatt   4740
tattggttat tctgaagata gtaattttat agtttattta aatagaaatg ccaccgcaat   4800
tatagtagtg tgcttttatt gtgtatattc atacttttat cgtggtcgaa agtcttggta   4860
tgtctcatct gtattgtact ctctgttctt tctttttctg gatagccgag caggaataat   4920
atcatttgct atatcgttgt tttttgtttt tcttcagtta acaaagaagg aaaagttatt   4980
aatatcattg ttttttgttc ctcttctaac tttaggtatt tcttttactg atataggcac   5040
tcgtcttgaa cgaatgctgt cttcgtcaca ggttatattc tctggtggta acactcttac   5100
aaaaagtcag aatgattatc gtcgagttga gttagtattt attggggttg atgttttaaa   5160
agaaaattat ttaattggca ctggattagg tgttgcaaat tatgtaaagg ctatagataa   5220
aaagttttta ggaagtacca actttgggtt ggcgcataat ttttatttat cttattcggc   5280
tcagttaggg attattggtt ttattttgct tatttctgta ttttatataa tgctgtctcc   5340
aatttttaaa tgcggagggt atattggtaa aggatgcgtt tttgctttgg ctttctatgt   5400
ctttttttaat gagtatatat tgacgccagc gatatatatt tatatttcta tttttttatc   5460
ggtggttttt atacgtaatt ctaaatagct gcgcggaata gtagatcact ttgagggaac   5520
ttagcccgga ttgtgcgatc tgatcaatcg ccaaatcaaa acaaatcacc aaccggactg   5580
agcaatgccg atcatagcac caatttcccg tgacgaacga cgcctgatgc agaaagccat   5640
ccataaaaca cacgataaaa attatgcccg cagactgact gccatgctga tgctgcaccg   5700
gggcgaccgt gtcagcgacg ttgccagaac gctctgctgc gcccgttcct ctgttggacg   5760
ctggattaac tggttcacgc agtcgggtgt tgagggactg aaatcattac ctgccgggcg   5820
tgcccgtcgc tggccgtttg agcatatctg cacactgtta cgtgagctgg taaaacattc   5880
tcccggcgac tttggctacc agcgttcacg ctggagtaca gaactgctgg caataaaaat   5940
caatgagata accggttgcc agttaaatgc cggaaccgtt cgccgctggt tgccgtctgc   6000
ggggattgtg tggcgaaggg ctgcgccaac tctgcgtatc cgtgacccgc ataaagatga   6060
aaagatggca gcaatccata aagcactgga cgaatgcagc gcagagcatc cggtctttta   6120
tgaagatgaa gtggatatcc atcttaatcc caaaatcggt gcggactggc aactgcgcgg   6180
acagcaaaaa cgggtggtca cgccgggaca gaatgaaaaa tattatctgg ccggagcgct   6240
gcacagcggg acaggtaaag tcagctgtgt gggcggcaac agcaaaagtt cggcgctgtt   6300
catcagcctg ctgaagcggc ttaaagcgac ataccgtcgg gcgaaaacca tcacgctgat   6360
cgtggacaac tacattatcc acaaaagccg ggaaacacag agctggctga aggagaaccc   6420
gaagttcagg gtcatttatc agccggttta ctcgccatgg atgaatcatg ttgaacggct   6480
atggcaggca cttcacgaca caataacgcg taatcatcag tgcagctcaa tgtggcaact   6540
gttgaaaaaa gttcgccatt ttatggaaac cgtcagccca ttccccggag gcaaacatgg   6600
gctggcaaaa gtgtagcggt attaagcgca gctatttagg atgagaatat gttgttagaa   6660
```

```
tatgttgaaa gaaaaatttc cttagccttg agtaagtatc ctaaggtaag ggatgttatt   6720
aagttctttt atttatatat cgcatcatta ttcggaatta ttttgaataa aaataagacg   6780
gttattcaat caaaaatata cgagatttca attgatgatt ctgaagaatc attttttggc   6840
tattatgacc atagtccaat gagctctaat gggcggtacg tattgttcca ctctagtgcg   6900
tttagcacta aacgacatcc aaagaaagtt aagtatatat ctatttgcgt aaaagacctt   6960
cttaataaca aagtttataa gctatatgat acgcgagcat ttaattggca gcagggaagc   7020
cgattaatgt ggattgatga tgacaatata atttttaatg actatgaaaa taatggatac   7080
attagtgttg tctattcttt gtctttgatg aaggttataa aaaaaataaa ctatccgatt   7140
tatgatgtga ataattacaa ggctgtgacg ttagatttct catggctggc taaatatgat   7200
agcgattatg gttattataa taaaaaatca ttttctacag atatttcaat cattaatttg   7260
aatacggggg gaatagaatt atttttatcc ttagacgaaa tgctaaagag aactaatttt   7320
aaatgtaata ttgatgttga acatgtggtc aatcatttta tgtttgctcc cgatggacgt   7380
tccgttatgt tcatacatcg atactataca cctaaaggaa agcgtgaaag gttaatacat   7440
tggaatttaa taaatgataa tgttcgagtc ctaataaatg aatcgattat tagtcattgt   7500
tgttggaatg ggaatgatga aattataggt ttttttggtg cagaaataga ttcgctaaat   7560
tattatagat tgtcaattga atcctgtaat acagagaaat tgttttttga tgcaagaaaa   7620
tattctgatg gacatcctac tatagttcat aatagatata ttatatctga tacttaccca   7680
gataaaaata gaattaaaaa gttgtttgtt tatgaccttg tcaaaaatga ttatcgcgag   7740
cttggattat tttatgagtc aatgagtttt ttttcttatt ctcgatgtga cttacatcca   7800
aggatctcgg ttgataatag atttttgttt gttgattcag ttcactcagg gaaaagaaaa   7860
ctatatttta tgaggagtgg tatttgtgag tgatgttcta gtatctttaa ttatagtttg   7920
ctttaatgca gagaagtata ttgaaaaatc tcttttggca tttattaatc aagatgttgg   7980
attagataaa tttgaattga ttattgtaga tggggattca tctgataata caatatctat   8040
tgttcaggat gtttttttcta aacatagcaa cattaagcat aaaattatca ataataaaaa   8100
aagaactctt gctacgggtt ggaatattgg ggtgctagaa gctaatggta agtttgtgtg   8160
tagagttgat gcacatagtg atattccaaa taactatata tctaaattat tagatgatta   8220
ttttaatatt atgcagtttg atgatagcgt tgttggtgtt ggaggtgtat taactaattc   8280
ttataaaact aagtttggtt caattgtagc ggatttttat gcatcgaaat ttggtgttgg   8340
taattctcca tttaggtgcg tagacaaaaa taatcgacta aaaaaaacag atacagctgt   8400
ctttgcttta tataataaag atgtgttttt tgatgttgga ctttttaatg aagtattaga   8460
tagaaatcaa gatattgatt ttcataagag agttttaagc aataatttgt cattatatac   8520
agataatagt ttatttgttg agtattatgt tagagataat tttaaagatt tcataaagaa   8580
aggttttctt gatggttttt gggttgttat gtctggagca tattatttta gacatatagt   8640
gccacttttt tttgttttgt atttaattgt atctttttct cttttctttg ctactggtga   8700
ttatatatat ttatcttttt tattttttta ttttcttatt tctattttgt tttcaattcg   8760
agatgggcga agttttatag gtagagtatt tcttcctttt atatttttgt cttatcatat   8820
ttcttatgga tgtggatcgt tattatcttt tttgaaaagg tattttaaat gaaaaatttt   8880
attccttttg cgttacctga aattggcgaa gaagaaattg cagaggtaat tgactcttta   8940
cgttcaggtt ggattacgac aggtcctaag gctaagcaat ttgaacaaga attttctaat   9000
```

-continued

```
tacctaggag cgaacgttca atcattagct gttaactctg ctacgtcggg cttacatttg   9060
gctcttgaag ctgttggcgt aaagccggga gaccaagtta ttgtcccatc atatacattc   9120
actgctactg ccgaaattgt caggtacctt ggtgctgatc ctgtaattgt tgatgtagat   9180
cgtaaaacat ttaatatatc agttgatgcc attgagaagg ctattactaa tgaaacaaag   9240
gcgattattc cagtacactt cgctggatta gcttgtgaca tggattcaat cttatcaatt   9300
gctaaaaaat atgacctaaa ggttgtcgag gatgccgctc atgcatttcc tacaacatat   9360
aaaggaagta agataggaac gcttgattca gatgctacgg tttttagctt ctacgccaat   9420
aaaactatga caaccggtga aggcggaatg gttgtttcaa aaaataaaga tataattgag   9480
cgttgtaagg taatgcgttt acatggaatc agtcgtgacg cttttgaccg gtaccagtct   9540
aaaactcctt cttggtttta tgaggttgta gctccagggt ttaaatacaa tatgcctgat   9600
atctgtgcgg caatcggtat tcatcaactt agaaagatcg atgattttca gaaaaaacgt   9660
caacgaatgg caaaaattta cgatgatgcg ttaaaagaat tgccacttga attgcctgaa   9720
tggcctacta atgctagtga tattcatgct tggcatctat atcctatccg cttaaaaact   9780
gattcggcta ttaatcgcga tgattttatt aagaagttat cagatcttgg aattggttgt   9840
tctgtccatt ttataccgtt gcataagcaa ccggtttggc gtgatacata taatttgaac   9900
gccagtgact ttccagtttc tgaggagtgt tatttaaatg aaatatctat tcctctttat   9960
actaaaatga cggatcaaga tcagttgttc gttatcaaat cgattagaca attatttatg  10020
taatggtatt ttatattaaa tgaaacgtat ttttgatgtt atcgtggcag gcttaggcct  10080
gctttttcta tttcctgttt ttatcattgt gtcaatgtta attgttgctg attctaaagg  10140
gggggttttt tttaggcagt atagagttgg gagatttggg aaagatttta ggatacataa  10200
atttagaacg atgtttatcg attcagaaaa aaaaggacgg ataacagttg gtcaagatgc  10260
tcgggtaacc agagttggat ggtatttacg gaagtacaaa atcgatgagc ttcctcaatt  10320
gatagatgtt ctttctggaa caatgagttt ggttggccca agaccggaag tgagggagtt  10380
tattgatgag tatcctgatg atataaggga aaaagtttta tcggttaggc cagggataac  10440
tgacttagca tctatagaaa tggtagatga aaatgagatt ttgtctagtt atgatgaccc  10500
acgtagggct tatatagata taattcttcc aatcaagcaa agatattatt tagattatgt  10560
tgctaacaat tcagtaaagt atgattgtgt gataatttgg aaaactatta ttaagatttt  10620
gtcgcgataa taaggtagtg taggatgatt gatagaatat tggagctgcc aagaattgtt  10680
aagagaggta tcatcatctg cattgatgta gttatggtga tattctcatt ttggttgtct  10740
tattggttga ggcttgatga gcaaacggct tttcttagtg caccgatgtg gtttgctgca  10800
gctattctta ccatatttac cgtgtttata tttatcagga ttgggcttta tcgggcagtc  10860
ttacggtatg ttagtgcaaa gataatgttg ctaataccag ttggtattct ggcctcaacg  10920
ttatctcttg tcgttatatc atattcgcta tccataatgt tgccgcgcac tgttgtcgga  10980
atttattttt tggttttact tttactgaca tcaggctcta gattgctttt tagaatgata  11040
cttaactatg gagttaaggg tagtgcgcct gttttgattt atggcgctgg tgaatctggc  11100
cgacaattat tgccagcatt aatgcaggca aaagaatatt ttcctgtggc atttgtggat  11160
gataatcctc gcttgcataa ggctgtcatt catggtgtaa cagtttatcc ctcggataaa  11220
ctgagttacc ttgtagatcg ctatggtata aagaaaattc ttttggcgat gccgagcgtc  11280
agtaagtcac aaaggcagaa agtgattact cgtttagagc atctaccgtg tgaagttctc  11340
tctattccgg gtatggtcga tttagtcgaa ggtcgagcac aaatcagtaa tctaaaaaaa  11400
```

```
gtatcgattg atgacttact aggtcgtgat ccggttgctc ctgatgccaa attgatggcc  11460
gaaaacatta ctggcaaagc cgttatggtc actggggcgg gaggctcgat cggctctgag  11520
ctttgtcgtc aaattgttcg atataagccg gccaaattgg ttctatttga actgtctgaa  11580
tatgccctct acgctattga gaaagagctc tcggcgctgt gcgacaaaga agttttgaat  11640
gttccagtga tccctctgtt gggctcggtg cagcgtcaga atcgcttaca gatggtgatg  11700
aagtcctttg gtattcaaac ggtttatcat gcggccgctt ataaacatgt gcctctggtt  11760
gagcataatg tggtggaagg ggtacgtaat aacgtgtttg gtaccttgta ctgcgctgag  11820
tcagcgatcg aaagtggcgt tgaaactttt gtgttgattt ccaccgataa agcggtgcgc  11880
ccgaccaaca ctatggggac aactaagcgt ctggccgaat tggtattgca ggctttgtct  11940
gcacggcaaa gccaaactcg cttttgtatg gtgcgatttg gtaatgtact cggttcttcg  12000
ggctctgtcg tgccgttgtt tgaaaaacag attgcccaag gtgggccagt taccttgact  12060
catcgtgaca ttattcgcta tttcatgaca attccggaag catcacagtt ggtgattcaa  12120
gcgggggcga tggggcatgg cggcgatgtc tttgtcttag acatgggcga tccggtcaag  12180
atttatgact tagccaaacg catgatccgg ttaagtggct tgagtgtacg ggatgataaa  12240
aatccagatg gcgatattgc cattgaagtt acgggattac gtccagggga gaaactgtat  12300
gaagaattac tgattggtga ttcagttcaa ggtacctctc atccacgaat tatgacggcc  12360
aacgaagtga tgctaccgtg gcaggatcta tcgctcttac ttaaagagct ggatcaagct  12420
tgtcatgact ttgatcatga gcgaattcgc agtttgttgt tacaagcacc agcggcattc  12480
aatccaactg atgatatttg cgatctagtt tggcagcaga aaaaatcgct gttatcacaa  12540
gcgagcaatg tcattcgcct gtgattgctt aggtttaacc ttccacacca attcttcacc  12600
tctcttacaa atccccgcta ggcggtacat cgtgaccgcc tttagcctga tgcctgctct  12660
ttaacaaaca ggacatcagt gtatgtttaa accttttagc gccgaatttt tcggcacttt  12720
ctggctggtt ctgggtggct gtggtagcgc cttgatctct gctgctttcc cacagttagg  12780
tataggcttt ttgggcgtgg cgttggcgtt tggtctgaca gtagtcacca tggcttatgc  12840
ggtcgggcac atctctggtg cgcattttaa ccccgcggtg accttgggtc tgtgggccgg  12900
tggacgcttc ccagcagcgc gcgtgttacc ttacattatc gctcaggtta tcggcggtat  12960
tgccgctgcg gcagtgctgt atggtatcgc cagcggtaag gctgggtttg atgcgacaac  13020
cagcggtttt gcggctaatg gttatggcct ccattcacct ggcggctatg cgttaagcgc  13080
ctgtatgctg agcgagtttg tcctcagtgc gttttttgtc cggagcgaca gaaaaacgcg  13140
ctcctgcggg ctttgcgcca ctggcgattg gtctggtaat caccccgtaa attaaccagc  13200
gtcaaaagta gaattttctc gtaccataaa cgcaggagat tctttatgca aacatcaaaa  13260
tttaccgaca agcaaatcat ggcgatcctc aaatgaaccc ccccgggaat cctggagact  13320
aaacttcctg agaaagaggt aaacaggatg actaaaaata ctcgtttttc ccccgaagtc  13380
cgtcaacggg cagtccgtat ggttctggaa agtcagggcg aatatgactc acaatgggcg  13440
acaatttgtt ccattgctcc aaagattggc tgtacgccgg agactctgcg tgtccgggtt  13500
cgccagtatg agcgggatac cgggggcggt gatggagggc tcaccaccgc tgaacgtcag  13560
cgtctgaaag agctggagcg tgaaaatcgt gaactgcgcc gcagtaacga tatccttcgc  13620
caagctt                                                            13627
```

<210> SEQ ID NO 3

<211> LENGTH: 13307
<212> TYPE: DNA
<213> ORGANISM: Shigella sonnei
<220> FEATURE:
<221> NAME/KEY: misc_feature
<223> OTHER INFORMATION: 13.3 kb HindIII-SmaI fragment from AF294823 (SEQ ID NO:7 positions 1310-14616) encoding Shigella sonnei O antigen gene cluster

<400> SEQUENCE: 3

```
aagcttgatc aaatagctca tattcagcga gatttaacaa ctgcggaaca agccggaatc     60
attgattatc gctctagcaa aggcggcttc gataatgcgc aaagtagcta taagttcttg    120
ctcggcgaaa aactgttatc agcagagcta aaagcaacta aagatgcgcc aattatttac    180
ccatttagat attacgaagt gaaacgtcaa attgatgagt tagaaggaat gttacgcgat    240
aacattcagg cgcaagcata tcgatatcaa atgaagccat ctgagccagt tataaaagac    300
aaacccaaca aagcattaat tttgattctt ggtgcattac caggggcaat gtttgctata    360
gttggtacat tagtttatgc gacattaaaa gataaaacca agttagatta aactgggtta    420
cgtattgttg tgtcaatgcg aaatagatgt tctatgtgca ctttatgatg gataagaaaa    480
tgaaattcga tactttgaat gcgaaaattg ggattatagg ccttggttat gttggattgc    540
ctcttgctgt tgagtttgga aagaaagtaa cgacgattgg atttgatatt aataagtctc    600
gtattgatga attacgaaat ggtcacgata gtacattaga gtgctcaaat ttagagttgt    660
tagaagcaac taaattgacg tacgcctgtt cattagatgc actaaaagag tgtaatgtat    720
ttattgtaac tgttccaact ccaattgata aacataaaca gccagatcta acacctctaa    780
ttaaagcatc tgaaacattg ggtaagataa taaagaaagg cgatgttatt atttatgagt    840
caacagttta ccctggagcg acagaagaag attgtatacc agttgtagag aaagtatcag    900
gtcttaagtt taatattgat ttttttgccg gttattcacc tgagcgtatt aatcctgggg    960
ataaagagca tcgtgtaact aatatcctta aggtgaccag tggatctaca ccggatgttg   1020
ctgagtatgt agatcagcta tataaattaa taattactgt cggtacgcat aaagcatcat   1080
cgataaaagt agcagaggct gcaaaagtaa ttgaaaacac gcagcgagat gtcaatattg   1140
cattgattaa tgagttatct attatattta ataagttagg gattgatacc ttagaggttc   1200
ttgaggctgc aggtacgaag tggaattttt taccttttag gcccggttta gtaggtggcc   1260
actgtatagg tgtagatcct tattatctta cacataaagc gcaaagtgtc ggctatcatc   1320
cggagatgat tttagccgga cgtcgtttaa atgatagtat ggggcagtat gtcgtttccc   1380
agttagtcaa aaaaatgttg aaacaacgga ttcaagttga aggggcgaat gtgttagtga   1440
tggggcttac atttaaagag aattgcccag atctacgaaa cactaaagtg attgatatta   1500
tttcagagtt aaaagaatac aatatcaata tagatattat agatccatgg tgttctaccg   1560
atgaggcaca acatgaatat ggattaactt tatgtgaaga tcctaaagtt aatcattatg   1620
atgcaataat tatcgctgtt gcacacaatg agtttcgcga gatgggagag agcgctattc   1680
gtgcattagg taaagacgag cacgttttgt tcgatttaaa atatgtgctt gataaaaaaa   1740
gtatcgatat gcgcttgtaa gagtgattaa aaaaatcaaa tcctctttga tatgatacac   1800
ctcagcattt tatgctaggt ttagcacttg attaatatac atggatattt atatgtctcg   1860
ctatgaagag attacacagc agttaatttt ttcaccgaaa acttggttaa ttactggtgt   1920
cgctggcttt ataggatcaa atcttttaga aaagttactt aaattaaacc aggttgttat   1980
tgggttagat aacttttcca cgggacatca atataatctt gatgaagtta aaacattagt   2040
```

```
ttccactgaa cagtggagtc gattttgctt tatagaaggt gatattcgag atctcactac   2100
ctgtgagcaa gttatgaaag gtgttgatca tgtcttacat caggctgcgc taggttctgt   2160
acctcgttca attgttgatc ctataacaac caatgcaact aatattactg gatttttgaa   2220
tatcttacat gcggctaaaa atgcacaagt acaaagtttt acttatgctg catcaagctc   2280
aacttatgga gatcatcccg cactaccaaa agtagaggaa aacattggta atccactttc   2340
tccttatgca gttactaaat atgttaacga gatttatgct caggtatatg ctcgaacata   2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgatttttgt tatatagata atgttataca   2580
aatgaatata ttatctgcat tagcgaagga cagtgctaaa gataatatat ataatgttgc   2640
agttggtgat agaacaacgt taaatgaatt atctggttac atttatgatg agcttaattt   2700
aattcaccat atcgataaat tgagcattaa gtatagagag tttagatctg gagatgttag   2760
gcattctcag gctgatgtta ctaaggctat agatttacta aagtatagac caaatataaa   2820
aatcagagag ggattacgac tttcaatgcc gtggtatgtg agatttttaa aaggctaaat   2880
tatattaaca tgaataaata atctatttca cctctgttat taatgcaggg gtgaaaatcc   2940
atgtatttat tctaaatggt cagtgtatgt ttagaaaaat gattgatgca ggtggtacat   3000
ttttacttaa agcaatattt caaataggag tttttgttta tttcacacat gtgtcagata   3060
ttactacatt tggtattatt agttatgtgt ttactgttta ttggtttgtg cttaacttct   3120
ctgattatgg atttagaaca aaattagtga aagatatttc tgataatagt tattctgcat   3180
cagaattatt atcaagaagt gatggagtta aaacatatgt ttttttcttc atttttataa   3240
tcttcatgtt ttattcttat gtttctgatt caatttcatt aactctgctt gtttatattt   3300
catctgcata ttttgtttgt atttcaagtg gtagatttag cttgctacag gctgttggtc   3360
ggtttagatg tgaattatat ataaatatct actcaacaat tatatatatt gggtgtaatt   3420
tatttttatc tctgtttatc gaacctctat attatagtgc gatatcaata ttcatatact   3480
caatttcgct tttggtttc tcatcacata aatgcaatgt gccatgtttt catataaaaa   3540
gaccaagtat tttagtttat aaagattttt tggatgcaac tccgttcgct attctggtgt   3600
tactaaatgt tgttttatct agtattgacc tttttatatt aaaagaatat ttctcttata   3660
atagtgttgc tatatatcag gtggtaacta gggttaatac cggtctaata atagtgttta   3720
atgttattta tactgtttta ttgccttcat tttcttatta tctgaaaaat tctgaatggg   3780
gtaatataag gaaattacaa cgatatatat cactgttagt cttattacta tgtttatgct   3840
attatttttt tggcatctat ttcgtaggga tattgtttgg tgatgagtat aaggtaatat   3900
cttctgcaac atttttgata atgtttatgg ctcttattaa atataatttt tggctaataa   3960
atgaacttta tcttgtgtgt agtggaaatc aaagcgagcg agttaaatcg tattgtattg   4020
gtgtggtcat ttcaatggcg gtttttcttt attttatacc tcggtatgga tggagtgggg   4080
cggtttttgg aagtgccatt gcaacattag taattggaat attttatatt atttctgtga   4140
aaaaagattg tgggaaaatt cttcatgata agtattcact aatgatgatc tttgtcccaa   4200
ttttctttta ttttattatt aatggtcagc agcggttgtt atattaatat gttgtggttt   4260
tatatcgttc cattaatatg tttagactcg attggaagcc taataaaggt taagtatgtt   4320
aatataccta tatcctgtac ttttgttatt taatatcctt ccggtttttt tttatggaca   4380
aatgaactct gatttagagc gtttttttgg agttcctatt ggctatattc cagatctaat   4440
```

```
attttatttc tttgttgttt taacatctat aataacgttg aggtttcacg tttctctgtg   4500
gacaaagaaa ttattatttt taggcatcat attcctgatt tatatcagca ttcagatgtt   4560
gttgttatca gcggatatat caggtgtcgt aattttatta tcgttttttt ctaattttat   4620
agctttggtt cttttggtgt cattttgcat tggtaaagat gagctttatt taactcattc   4680
ggttagaaat ataaatgttg taatgtgttt tggtattatc tgtggagttg taaaattatt   4740
tattggttat tctgaagata gtaattttat agtttattta aatagaaatg ccaccgcaat   4800
tatagtagtg tgcttttatt gtgtatattc atacttttat cgtggtcgaa agtcttggta   4860
tgtctcatct gtattgtact ctctgttctt tctttttctg gatagccgag caggaataat   4920
atcatttgct atatcgttgt tttttgtttt tcttcagtta acaaagaagg aaaagttatt   4980
aatatcattg ttttttgttc ctcttctaac tttaggtatt tcttttactg atataggcac   5040
tcgtcttgaa cgaatgctgt cttcgtcaca ggttatattc tctggtggta acactcttac   5100
aaaaagtcag aatgattatc gtcgagttga gttagtattt attggggttg atgttttaaa   5160
agaaaattat ttaattggca ctggattagg tgttgcaaat tatgtaaagg ctatagataa   5220
aaagttttta ggaagtacca actttgggtt ggcgcataat ttttatttat cttattcggc   5280
tcagttaggg attattggtt ttattttgct tatttctgta ttttatataa tgctgtctcc   5340
aatttttaaa tgcggagggt atattggtaa aggatgcgtt tttgctttgg ctttctatgt   5400
ctttttttaat gagtatatat tgacgccagc gatatatatt tatatttcta ttttttttatc   5460
ggtggttttt atacgtaatt ctaaatagct gcgcggaata gtagatcact ttgagggaac   5520
ttagcccgga ttgtgcgatc tgatcaatcg ccaaatcaaa acaaatcacc aaccggactg   5580
agcaatgccg atcatagcac caatttcccg tgacgaacga cgcctgatgc agaaagccat   5640
ccataaaaca cacgataaaa attatgcccg cagactgact gccatgctga tgctgcaccg   5700
gggcgaccgt gtcagcgacg ttgccagaac gctctgctgc gcccgttcct ctgttggacg   5760
ctggattaac tggttcacgc agtcgggtgt tgagggactg aaatcattac ctgccgggcg   5820
tgcccgtcgc tggccgtttg agcatatctg cacactgtta cgtgagctgg taaaacattc   5880
tcccggcgac tttggctacc agcgttcacg ctggagtaca gaactgctgg caataaaaat   5940
caatgagata accggttgcc agttaaatgc cggaaccgtt cgccgctggt tgccgtctgc   6000
ggggattgtg tggcgaaggg ctgcgccaac tctgcgtatc cgtgacccgc ataaagatga   6060
aaagatggca gcaatccata aagcactgga cgaatgcagc gcagagcatc cggtctttta   6120
tgaagatgaa gtggatatcc atcttaatcc caaaatcggt gcggactggc aactgcgcgg   6180
acagcaaaaa cgggtggtca cgccgggaca gaatgaaaaa tattatctgg ccggagcgct   6240
gcacagcggg acaggtaaag tcagctgtgt gggcggcaac agcaaaagtt cggcgctgtt   6300
catcagcctg ctgaagcggc ttaaagcgac ataccgtcgg gcgaaaacca tcacgctgat   6360
cgtggacaac tacattatcc acaaaagccg ggaaacacag agctggctga aggagaaccc   6420
gaagttcagg gtcatttatc agccggttta ctcgccatgg atgaatcatg ttgaacggct   6480
atggcaggca cttcacgaca caataacgcg taatcatcag tgcagctcaa tgtggcaact   6540
gttgaaaaaa gttcgccatt ttatggaaac cgtcagccca ttccccggag gcaaacatgg   6600
gctggcaaaa gtgtagcggt attaagcgca gctatttagg atgagaatat gttgttagaa   6660
tatgttgaaa gaaaaatttc cttagccttg agtaagtatc ctaaggtaag ggatgttatt   6720
aagttctttt atttatatat cgcatcatta ttcggaatta ttttgaataa aaataagacg   6780
```

```
gttattcaat caaaaatata cgagatttca attgatgatt ctgaagaatc attttttggc   6840
tattatgacc atagtccaat gagctctaat gggcggtacg tattgttcca ctctagtgcg   6900
tttagcacta aacgacatcc aaagaaagtt aagtatatat ctatttgcgt aaaagacctt   6960
cttaataaca aagtttataa gctatatgat acgcgagcat ttaattggca gcagggaagc   7020
cgattaatgt ggattgatga tgacaatata atttttaatg actatgaaaa taatggatac   7080
attagtgttg tctattcttt gtctttgatg aaggttataa aaaaaataaa ctatccgatt   7140
tatgatgtga ataattacaa ggctgtgacg ttagatttct catggctggc taaatatgat   7200
agcgattatg gttattataa taaaaaatca ttttctacag atatttcaat cattaatttg   7260
aatacggggg gaatagaatt atttttatcc ttagacgaaa tgctaaagag aactaatttt   7320
aaatgtaata ttgatgttga acatgtggtc aatcatttta tgtttgctcc cgatggacgt   7380
tccgttatgt tcatacatcg atactataca cctaaaggaa agcgtgaaag gttaatacat   7440
tggaatttaa taaatgataa tgttcgagtc ctaataaatg aatcgattat tagtcattgt   7500
tgttggaatg ggaatgatga aattataggt ttttttggtg cagaaataga ttcgctaaat   7560
tattatagat tgtcaattga atcctgtaat acagagaaat tgttttttga tgcaagaaaa   7620
tattctgatg gacatcctac tatagttcat aatagatata ttatatctga tacttaccca   7680
gataaaaata gaattaaaaa gttgtttgtt tatgaccttg tcaaaaatga ttatcgcgag   7740
cttggattat tttatgagtc aatgagtttt ttttcttatt ctcgatgtga cttacatcca   7800
aggatctcgg ttgataatag atttttgttt gttgattcag ttcactcagg gaaaagaaaa   7860
ctatatttta tgaggagtgg tatttgtgag tgatgttcta gtatctttaa ttatagtttg   7920
ctttaatgca gagaagtata ttgaaaaatc tcttttggca tttattaatc aagatgttgg   7980
attagataaa tttgaattga ttattgtaga tggggattca tctgataata caatatctat   8040
tgttcaggat gtttttttcta aacatagcaa cattaagcat aaaattatca ataataaaaa   8100
aagaactctt gctacgggtt ggaatattgg ggtgctagaa gctaatggta agtttgtgtg   8160
tagagttgat gcacatagtg atattccaaa taactatata tctaaattat tagatgatta   8220
ttttaatatt atgcagtttg atgatagcgt tgttggtgtt ggaggtgtat taactaattc   8280
ttataaaact aagtttggtt caattgtagc ggatttttat gcatcgaaat ttggtgttgg   8340
taattctcca tttaggtgcg tagacaaaaa taatcgacta aaaaaaacag atacagctgt   8400
ctttgcttta tataataaag atgtgttttt tgatgttgga ctttttaatg aagtattaga   8460
tagaaatcaa gatattgatt ttcataagag agttttaagc aataatttgt cattatatac   8520
agataatagt ttatttgttg agtattatgt tagagataat tttaaagatt tcataaagaa   8580
aggttttctt gatggtttttt gggttgttat gtctggagca tattatttta gacatatagt   8640
gccacttttt tttgttttgt atttaattgt atctttttct cttttctttg ctactggtga   8700
ttatatatat ttatcttttt tattttttta ttttcttatt tctattttgt tttcaattcg   8760
agatgggcga agttttatag gtagagtatt tcttcctttt atatttttgt cttatcatat   8820
ttcttatgga tgtggatcgt tattatcttt tttgaaaagg tattttaaat gaaaaatttt   8880
attccttttg cgttacctga aattggcgaa gaagaaattg cagaggtaat tgactcttta   8940
cgttcaggtt ggattacgac aggtcctaag gctaagcaat ttgaacaaga attttctaat   9000
tacctaggag cgaacgttca atcattagct gttaactctg ctacgtcggg cttacatttg   9060
gctcttgaag ctgttggcgt aaagccggga gaccaagtta ttgtcccatc atatacattc   9120
actgctactg ccgaaattgt caggtacctt ggtgctgatc ctgtaattgt tgatgtagat   9180
```

```
cgtaaaacat ttaatatatc agttgatgcc attgagaagg ctattactaa tgaaacaaag   9240
gcgattattc cagtacactt cgctggatta gcttgtgaca tggattcaat cttatcaatt   9300
gctaaaaaat atgacctaaa ggttgtcgag gatgccgctc atgcatttcc tacaacatat   9360
aaaggaagta agataggaac gcttgattca gatgctacgg tttttagctt ctacgccaat   9420
aaaactatga caaccggtga aggcggaatg gttgtttcaa aaaataaaga tataattgag   9480
cgttgtaagg taatgcgttt acatggaatc agtcgtgacg cttttgaccg gtaccagtct   9540
aaaactcctt cttggtttta tgaggttgta gctccagggt ttaaatacaa tatgcctgat   9600
atctgtgcgg caatcggtat tcatcaactt agaaagatcg atgattttca gaaaaaacgt   9660
caacgaatgg caaaaattta cgatgatgcg ttaaaagaat tgccacttga attgcctgaa   9720
tggcctacta atgctagtga tattcatgct tggcatctat atcctatccg cttaaaaact   9780
gattcggcta ttaatcgcga tgattttatt aagaagttat cagatcttgg aattggttgt   9840
tctgtccatt ttataccgtt gcataagcaa ccggtttggc gtgatacata taatttgaac   9900
gccagtgact ttccagtttc tgaggagtgt tatttaaatg aaatatctat tcctctttat   9960
actaaaatga cggatcaaga tcagttgttc gttatcaaat cgattagaca attatttatg  10020
taatggtatt ttatattaaa tgaaacgtat ttttgatgtt atcgtggcag gcttaggcct  10080
gctttttcta tttcctgttt ttatcattgt gtcaatgtta attgttgctg attctaaagg  10140
gggggttttt tttaggcagt atagagttgg gagatttggg aaagatttta ggatacataa  10200
atttagaacg atgtttatcg attcagaaaa aaaaggacgg ataacagttg gtcaagatgc  10260
tcgggtaacc agagttggat ggtatttacg gaagtacaaa atcgatgagc ttcctcaatt  10320
gatagatgtt ctttctggaa caatgagttt ggttggccca agaccggaag tgagggagtt  10380
tattgatgag tatcctgatg atataaggga aaaagtttta tcggttaggc cagggataac  10440
tgacttagca tctatagaaa tggtagatga aaatgagatt ttgtctagtt atgatgaccc  10500
acgtagggct tatatagata taattcttcc aatcaagcaa agatattatt tagattatgt  10560
tgctaacaat tcagtaaagt atgattgtgt gataatttgg aaaactatta ttaagatttt  10620
gtcgcgataa taaggtagtg taggatgatt gatagaatat tggagctgcc aagaattgtt  10680
aagagaggta tcatcatctg cattgatgta gttatggtga tattctcatt ttggttgtct  10740
tattggttga ggcttgatga gcaaacggct tttcttagtg caccgatgtg gtttgctgca  10800
gctattctta ccatatttac cgtgtttata tttatcagga ttgggcttta tcgggcagtc  10860
ttacggtatg ttagtgcaaa gataatgttg ctaataccag ttggtattct ggcctcaacg  10920
ttatctcttg tcgttatatc atattcgcta tccataatgt tgccgcgcac tgttgtcgga  10980
atttattttt tggttttact tttactgaca tcaggctcta gattgctttt tagaatgata  11040
cttaactatg gagttaaggg tagtgcgcct gttttgattt atggcgctgg tgaatctggc  11100
cgacaattat tgccagcatt aatgcaggca aaagaatatt ttcctgtggc atttgtggat  11160
gataatcctc gcttgcataa ggctgtcatt catggtgtaa cagtttatcc ctcggataaa  11220
ctgagttacc ttgtagatcg ctatggtata aagaaaattc ttttggcgat gccgagcgtc  11280
agtaagtcac aaaggcagaa agtgattact cgtttagagc atctaccgtg tgaagttctc  11340
tctattccgg gtatggtcga tttagtcgaa ggtcgagcac aaatcagtaa tctaaaaaaa  11400
gtatcgattg atgacttact aggtcgtgat ccggttgctc ctgatgccaa attgatggcc  11460
gaaaacatta ctggcaaagc cgttatggtc actggggcgg gaggctcgat cggctctgag  11520
```

```
ctttgtcgtc aaattgttcg atataagccg gccaaattgg ttctatttga actgtctgaa  11580

tatgccctct acgctattga gaaagagctc tcggcgctgt gcgacaaaga agttttgaat  11640

gttccagtga tccctctgtt gggctcggtg cagcgtcaga atcgcttaca gatggtgatg  11700

aagtcctttg gtattcaaac ggtttatcat gcggccgctt ataaacatgt gcctctggtt  11760

gagcataatg tggtggaagg ggtacgtaat aacgtgtttg gtaccttgta ctgcgctgag  11820

tcagcgatcg aaagtggcgt tgaaactttt gtgttgattt ccaccgataa agcggtgcgc  11880

ccgaccaaca ctatggggac aactaagcgt ctggccgaat tggtattgca ggctttgtct  11940

gcacggcaaa gccaaactcg cttttgtatg gtgcgatttg gtaatgtact cggttcttcg  12000

ggctctgtcg tgccgttgtt tgaaaaacag attgcccaag gtgggccagt taccttgact  12060

catcgtgaca ttattcgcta tttcatgaca attccggaag catcacagtt ggtgattcaa  12120

gcgggggcga tggggcatgg cggcgatgtc tttgtcttag acatgggcga tccggtcaag  12180

atttatgact tagccaaacg catgatccgg ttaagtggct tgagtgtacg ggatgataaa  12240

aatccagatg gcgatattgc cattgaagtt acgggattac gtccagggga gaaactgtat  12300

gaagaattac tgattggtga ttcagttcaa ggtacctctc atccacgaat tatgacggcc  12360

aacgaagtga tgctaccgtg gcaggatcta tcgctcttac ttaaagagct ggatcaagct  12420

tgtcatgact ttgatcatga gcgaattcgc agtttgttgt tacaagcacc agcggcattc  12480

aatccaactg atgatatttg cgatctagtt tggcagcaga aaaaatcgct gttatcacaa  12540

gcgagcaatg tcattcgcct gtgattgctt aggtttaacc ttccacacca attcttcacc  12600

tctcttacaa atccccgcta ggcggtacat cgtgaccgcc tttagcctga tgcctgctct  12660

ttaacaaaca ggacatcagt gtatgtttaa accttttagc gccgaatttt tcggcacttt  12720

ctggctggtt ctgggtggct gtggtagcgc cttgatctct gctgctttcc cacagttagg  12780

tataggcttt ttgggcgtgg cgttggcgtt tggtctgaca gtagtcacca tggcttatgc  12840

ggtcgggcac atctctggtg cgcattttaa ccccgcggtg accttgggtc tgtgggccgg  12900

tggacgcttc ccagcagcgc gcgtgttacc ttacattatc gctcaggtta tcggcggtat  12960

tgccgctgcg gcagtgctgt atggtatcgc cagcggtaag gctgggtttg atgcgacaac  13020

cagcggtttt gcggctaatg gttatggcct ccattcacct ggcggctatg cgttaagcgc  13080

ctgtatgctg agcgagtttg tcctcagtgc gttttttgtc cggagcgaca gaaaaacgcg  13140

ctcctgcggg ctttgcgcca ctggcgattg gtctggtaat caccccgtaa attaaccagc  13200

gtcaaaagta gaattttctc gtaccataaa cgcaggagat tctttatgca aacatcaaaa  13260

tttaccgaca agcaaatcat ggcgatcctc aaatgaaccc ccccggg                13307
```

<210> SEQ ID NO 4
<211> LENGTH: 12692
<212> TYPE: DNA
<213> ORGANISM: Shigella sonnei
<220> FEATURE:
<221> NAME/KEY: misc_feature
<223> OTHER INFORMATION: 12.7 kb HindIII-PmeI fragment from AF294823 (SEQ ID NO:7 positions 1310-14001) encoding Shigella sonnei O antigen gene cluster

<400> SEQUENCE: 4

```
aagcttgatc aaatagctca tattcagcga gatttaacaa ctgcggaaca agccggaatc     60

attgattatc gctctagcaa aggcggcttc gataatgcgc aaagtagcta taagttcttg    120

ctcggcgaaa aactgttatc agcagagcta aaagcaacta aagatgcgcc aattatttac    180
```

-continued

```
ccatttagat attacgaagt gaaacgtcaa attgatgagt tagaaggaat gttacgcgat    240
aacattcagg cgcaagcata tcgatatcaa atgaagccat ctgagccagt tataaaagac    300
aaacccaaca aagcattaat tttgattctt ggtgcattac caggggcaat gtttgctata    360
gttggtacat tagtttatgc gacattaaaa gataaaacca agttagatta aactgggtta    420
cgtattgttg tgtcaatgcg aaatagatgt tctatgtgca ctttatgatg gataagaaaa    480
tgaaattcga tactttgaat gcgaaaattg ggattatagg ccttggttat gttggattgc    540
ctcttgctgt tgagtttgga aagaaagtaa cgacgattgg atttgatatt aataagtctc    600
gtattgatga attacgaaat ggtcacgata gtacattaga gtgctcaaat ttagagttgt    660
tagaagcaac taaattgacg tacgcctgtt cattagatgc actaaaagag tgtaatgtat    720
ttattgtaac tgttccaact ccaattgata aacataaaca gccagatcta acacctctaa    780
ttaaagcatc tgaaacattg ggtaagataa taaagaaagg cgatgttatt atttatgagt    840
caacagttta ccctggagcg acagaagaag attgtatacc agttgtagag aaagtatcag    900
gtcttaagtt taatattgat ttttttgccg gttattcacc tgagcgtatt aatcctgggg    960
ataaagagca tcgtgtaact aatatcctta aggtgaccag tggatctaca ccggatgttg   1020
ctgagtatgt agatcagcta tataaattaa taattactgt cggtacgcat aaagcatcat   1080
cgataaaagt agcagaggct gcaaaagtaa ttgaaaacac gcagcgagat gtcaatattg   1140
cattgattaa tgagttatct attatattta ataagttagg gattgatacc ttagaggttc   1200
ttgaggctgc aggtacgaag tggaattttt taccttttag gcccggttta gtaggtggcc   1260
actgtatagg tgtagatcct tattatctta cacataaagc gcaaagtgtc ggctatcatc   1320
cggagatgat tttagccgga cgtcgtttaa atgatagtat ggggcagtat gtcgtttccc   1380
agttagtcaa aaaaatgttg aaacaacgga ttcaagttga aggggcgaat gtgttagtga   1440
tggggcttac atttaaagag aattgcccag atctacgaaa cactaaagtg attgatatta   1500
tttcagagtt aaaagaatac aatatcaata tagatattat agatccatgg tgttctaccg   1560
atgaggcaca acatgaatat ggattaactt tatgtgaaga tcctaaagtt aatcattatg   1620
atgcaataat tatcgctgtt gcacacaatg agtttcgcga gatgggagag agcgctattc   1680
gtgcattagg taaagacgag cacgttttgt tcgatttaaa atatgtgctt gataaaaaaa   1740
gtatcgatat gcgcttgtaa gagtgattaa aaaaatcaaa tcctctttga tatgatacac   1800
ctcagcattt tatgctaggt ttagcacttg attaatatac atggatattt atatgtctcg   1860
ctatgaagag attacacagc agttaatttt ttcaccgaaa acttggttaa ttactggtgt   1920
cgctggcttt ataggatcaa atcttttaga aaagttactt aaattaaacc aggttgttat   1980
tgggttagat aacttttcca cgggacatca atataatctt gatgaagtta aaacattagt   2040
ttccactgaa cagtggagtc gattttgctt tatagaaggt gatattcgag atctcactac   2100
ctgtgagcaa gttatgaaag gtgttgatca tgtcttacat caggctgcgc taggttctgt   2160
acctcgttca attgttgatc ctataacaac caatgcaact aatattactg gatttttgaa   2220
tatcttacat gcggctaaaa atgcacaagt acaaagtttt acttatgctg catcaagctc   2280
aacttatgga gatcatcccg cactaccaaa agtagaggaa aacattggta atccactttc   2340
tccttatgca gttactaaat atgttaacga gatttatgct caggtatatg ctcgaacata   2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgatttttgt tatatagata atgttataca   2580
```

```
aatgaatata ttatctgcat tagcgaagga cagtgctaaa gataatatat ataatgttgc   2640
agttggtgat agaacaacgt taaatgaatt atctggttac atttatgatg agcttaattt   2700
aattcaccat atcgataaat tgagcattaa gtatagagag tttagatctg gagatgttag   2760
gcattctcag gctgatgtta ctaaggctat agatttacta aagtatagac caaatataaa   2820
aatcagagag ggattacgac tttcaatgcc gtggtatgtg agatttttaa aaggctaaat   2880
tatattaaca tgaataaata atctatttca cctctgttat taatgcaggg gtgaaaatcc   2940
atgtatttat tctaaatggt cagtgtatgt ttagaaaaat gattgatgca ggtggtacat   3000
ttttacttaa agcaatattt caaataggag tttttgttta tttcacacat gtgtcagata   3060
ttactacatt tggtattatt agttatgtgt ttactgttta ttggtttgtg cttaacttct   3120
ctgattatgg atttagaaca aaattagtga aagatatttc tgataatagt tattctgcat   3180
cagaattatt atcaagaagt gatggagtta aaacatatgt tttttcttc atttttataa   3240
tcttcatgtt ttattcttat gtttctgatt caatttcatt aactctgctt gtttatattt   3300
catctgcata ttttgtttgt atttcaagtg gtagatttag cttgctacag gctgttggtc   3360
ggtttagatg tgaattatat ataaatatct actcaacaat tatatatatt gggtgtaatt   3420
tatttttatc tctgtttatc gaacctctat attatagtgc gatatcaata ttcatatact   3480
caatttcgct tttggttttc tcatcacata aatgcaatgt gccatgtttt catataaaaa   3540
gaccaagtat tttagtttat aaagattttt tggatgcaac tccgttcgct attctggtgt   3600
tactaaatgt tgttttatct agtattgacc tttttatatt aaaagaatat ttctcttata   3660
atagtgttgc tatatatcag gtggtaacta gggttaatac cggtctaata atagtgttta   3720
atgttattta tactgtttta ttgccttcat tttcttatta tctgaaaaat tctgaatggg   3780
gtaatataag gaaattacaa cgatatatat cactgttagt cttattacta tgtttatgct   3840
attatttttt tggcatctat ttcgtaggga tattgtttgg tgatgagtat aaggtaatat   3900
cttctgcaac atttttgata atgtttatgg ctcttattaa atataatttt tggctaataa   3960
atgaacttta tcttgtgtgt agtggaaatc aaagcgagcg agttaaatcg tattgtattg   4020
gtgtggtcat ttcaatggcg gttttctttt attttatacc tcggtatgga tggagtgggg   4080
cggtttttgg aagtgccatt gcaacattag taattggaat attttatatt atttctgtga   4140
aaaaagattg tgggaaaatt cttcatgata agtattcact aatgatgatc tttgtcccaa   4200
ttttctttta ttttattatt aatggtcagc agcggttgtt atattaatat gttgtggttt   4260
tatatcgttc cattaatatg tttagactcg attggaagcc taataaaggt taagtatgtt   4320
aatataccta tatcctgtac ttttgttatt taatatcctt ccggtttttt tttatggaca   4380
aatgaactct gatttagagc gttttttgg agttcctatt ggctatattc cagatctaat   4440
attttatttc tttgttgttt taacatctat aataacgttg aggtttcacg tttctctgtg   4500
gacaaagaaa ttattatttt taggcatcat attcctgatt tatatcagca ttcagatgtt   4560
gttgttatca gcggatatat caggtgtcgt aattttatta tcgttttttt ctaattttat   4620
agctttggtt cttttggtgt cattttgcat tggtaaagat gagctttatt taactcattc   4680
ggttagaaat ataaatgttg taatgtgttt tggtattatc tgtggagttg taaaattatt   4740
tattggttat tctgaagata gtaattttat agtttattta aatagaaatg ccaccgcaat   4800
tatagtagtg tgcttttatt gtgtatattc atacttttat cgtggtcgaa agtcttggta   4860
tgtctcatct gtattgtact ctctgttctt tctttttctg gatagccgag caggaataat   4920
```

-continued

```
atcatttgct atatcgttgt tttttgtttt tcttcagtta acaaagaagg aaaagttatt   4980
aatatcattg ttttttgttc ctcttctaac tttaggtatt tcttttactg atataggcac   5040
tcgtcttgaa cgaatgctgt cttcgtcaca ggttatattc tctggtggta acactcttac   5100
aaaaagtcag aatgattatc gtcgagttga gttagtattt attggggttg atgttttaaa   5160
agaaaattat ttaattggca ctggattagg tgttgcaaat tatgtaaagg ctatagataa   5220
aaagttttta ggaagtacca actttgggtt ggcgcataat ttttatttat cttattcggc   5280
tcagttaggg attattggtt ttattttgct tatttctgta ttttatataa tgctgtctcc   5340
aatttttaaa tgcggagggt atattggtaa aggatgcgtt tttgctttgg ctttctatgt   5400
ctttttttaat gagtatatat tgacgccagc gatatatatt tatatttcta ttttttttatc   5460
ggtggttttt atacgtaatt ctaaatagct gcgcggaata gtagatcact ttgagggaac   5520
ttagcccgga ttgtgcgatc tgatcaatcg ccaaatcaaa acaaatcacc aaccggactg   5580
agcaatgccg atcatagcac caatttcccg tgacgaacga cgcctgatgc agaaagccat   5640
ccataaaaca cacgataaaa attatgcccg cagactgact gccatgctga tgctgcaccg   5700
gggcgaccgt gtcagcgacg ttgccagaac gctctgctgc gcccgttcct ctgttggacg   5760
ctggattaac tggttcacgc agtcgggtgt tgagggactg aaatcattac ctgccgggcg   5820
tgcccgtcgc tggccgtttg agcatatctg cacactgtta cgtgagctgg taaaacattc   5880
tcccggcgac tttggctacc agcgttcacg ctggagtaca gaactgctgg caataaaaat   5940
caatgagata accggttgcc agttaaatgc cggaaccgtt cgccgctggt tgccgtctgc   6000
ggggattgtg tggcgaaggg ctgcgccaac tctgcgtatc cgtgacccgc ataaagatga   6060
aaagatggca gcaatccata aagcactgga cgaatgcagc gcagagcatc cggtctttta   6120
tgaagatgaa gtggatatcc atcttaatcc caaaatcggt gcggactggc aactgcgcgg   6180
acagcaaaaa cgggtggtca cgccgggaca gaatgaaaaa tattatctgg ccggagcgct   6240
gcacagcggg acaggtaaag tcagctgtgt gggcggcaac agcaaaagtt cggcgctgtt   6300
catcagcctg ctgaagcggc ttaaagcgac ataccgtcgg gcgaaaacca tcacgctgat   6360
cgtggacaac tacattatcc acaaaagccg ggaaacacag agctggctga aggagaaccc   6420
gaagttcagg gtcatttatc agccggttta ctcgccatgg atgaatcatg ttgaacggct   6480
atggcaggca cttcacgaca caataacgcg taatcatcag tgcagctcaa tgtggcaact   6540
gttgaaaaaa gttcgccatt ttatggaaac cgtcagccca ttccccggag gcaaacatgg   6600
gctggcaaaa gtgtagcggt attaagcgca gctatttagg atgagaatat gttgttagaa   6660
tatgttgaaa gaaaaatttc cttagccttg agtaagtatc ctaaggtaag ggatgttatt   6720
aagttctttt atttatatat cgcatcatta ttcggaatta ttttgaataa aaataagacg   6780
gttattcaat caaaaatata cgagatttca attgatgatt ctgaagaatc attttttggc   6840
tattatgacc atagtccaat gagctctaat gggcggtacg tattgttcca ctctagtgcg   6900
tttagcacta aacgacatcc aaagaaagtt aagtatatat ctatttgcgt aaaagacctt   6960
cttaataaca aagtttataa gctatatgat acgcgagcat ttaattggca gcagggaagc   7020
cgattaatgt ggattgatga tgacaatata atttttaatg actatgaaaa taatggatac   7080
attagtgttg tctattcttt gtctttgatg aaggttataa aaaaaataaa ctatccgatt   7140
tatgatgtga ataattacaa ggctgtgacg ttagatttct catggctggc taaatatgat   7200
agcgattatg gttattataa taaaaaatca ttttctacag atatttcaat cattaatttg   7260
aatacggggg gaatagaatt atttttatcc ttagacgaaa tgctaaagag aactaatttt   7320
```

```
aaatgtaata ttgatgttga acatgtggtc aatcatttta tgtttgctcc cgatggacgt   7380
tccgttatgt tcatacatcg atactataca cctaaaggaa agcgtgaaag gttaatacat   7440
tggaatttaa taaatgataa tgttcgagtc ctaataaatg aatcgattat tagtcattgt   7500
tgttggaatg ggaatgatga aattataggt ttttttggtg cagaaataga ttcgctaaat   7560
tattatagat tgtcaattga atcctgtaat acagagaaat tgttttttga tgcaagaaaa   7620
tattctgatg gacatcctac tatagttcat aatagatata ttatatctga tacttaccca   7680
gataaaaata gaattaaaaa gttgtttgtt tatgaccttg tcaaaaatga ttatcgcgag   7740
cttggattat tttatgagtc aatgagtttt ttttcttatt ctcgatgtga cttacatcca   7800
aggatctcgg ttgataatag atttttgttt gttgattcag ttcactcagg gaaaagaaaa   7860
ctatatttta tgaggagtgg tatttgtgag tgatgttcta gtatctttaa ttatagtttg   7920
ctttaatgca gagaagtata ttgaaaaatc tcttttggca tttattaatc aagatgttgg   7980
attagataaa tttgaattga ttattgtaga tggggattca tctgataata caatatctat   8040
tgttcaggat gtttttttcta aacatagcaa cattaagcat aaaattatca ataataaaaa   8100
aagaactctt gctacgggtt ggaatattgg ggtgctagaa gctaatggta agtttgtgtg   8160
tagagttgat gcacatagtg atattccaaa taactatata tctaaattat tagatgatta   8220
ttttaatatt atgcagtttg atgatagcgt tgttggtgtt ggaggtgtat taactaattc   8280
ttataaaact aagtttggtt caattgtagc ggatttttat gcatcgaaat ttggtgttgg   8340
taattctcca tttaggtgcg tagacaaaaa taatcgacta aaaaaaacag atacagctgt   8400
ctttgcttta tataataaag atgtgttttt tgatgttgga ctttttaatg aagtattaga   8460
tagaaatcaa gatattgatt ttcataagag agttttaagc aataatttgt cattatatac   8520
agataatagt ttatttgttg agtattatgt tagagataat tttaaagatt tcataaagaa   8580
aggttttctt gatggttttt gggttgttat gtctggagca tattatttta gacatatagt   8640
gccacttttt tttgttttgt atttaattgt atctttttct cttttctttg ctactggtga   8700
ttatatatat ttatcttttt tattttttta ttttcttatt tctattttgt tttcaattcg   8760
agatgggcga agttttatag gtagagtatt tcttcctttt atatttttgt cttatcatat   8820
ttcttatgga tgtggatcgt tattatcttt tttgaaaagg tattttaaat gaaaaatttt   8880
attccttttg cgttacctga aattggcgaa gaagaaattg cagaggtaat tgactcttta   8940
cgttcaggtt ggattacgac aggtcctaag gctaagcaat ttgaacaaga attttctaat   9000
tacctaggag cgaacgttca atcattagct gttaactctg ctacgtcggg cttacatttg   9060
gctcttgaag ctgttggcgt aaagccggga gaccaagtta ttgtcccatc atatacattc   9120
actgctactg ccgaaattgt caggtacctt ggtgctgatc ctgtaattgt tgatgtagat   9180
cgtaaaacat ttaatatatc agttgatgcc attgagaagg ctattactaa tgaaacaaag   9240
gcgattattc cagtacactt cgctggatta gcttgtgaca tggattcaat cttatcaatt   9300
gctaaaaaat atgacctaaa ggttgtcgag gatgccgctc atgcatttcc tacaacatat   9360
aaaggaagta agataggaac gcttgattca gatgctacgg tttttagctt ctacgccaat   9420
aaaactatga caaccggtga aggcggaatg gttgtttcaa aaaataaaga tataattgag   9480
cgttgtaagg taatgcgttt acatggaatc agtcgtgacg cttttgaccg gtaccagtct   9540
aaaactcctt cttggtttta tgaggttgta gctccagggt ttaaatacaa tatgcctgat   9600
atctgtgcgg caatcggtat tcatcaactt agaaagatcg atgattttca gaaaaaacgt   9660
```

```
caacgaatgg caaaaattta cgatgatgcg ttaaaagaat tgccacttga attgcctgaa   9720
tggcctacta atgctagtga tattcatgct tggcatctat atcctatccg cttaaaaact   9780
gattcggcta ttaatcgcga tgattttatt aagaagttat cagatcttgg aattggttgt   9840
tctgtccatt ttataccgtt gcataagcaa ccggtttggc gtgatacata taatttgaac   9900
gccagtgact ttccagtttc tgaggagtgt tatttaaatg aaatatctat tcctctttat   9960
actaaaatga cggatcaaga tcagttgttc gttatcaaat cgattagaca attatttatg  10020
taatggtatt ttatattaaa tgaaacgtat ttttgatgtt atcgtggcag gcttaggcct  10080
gctttttcta tttcctgttt ttatcattgt gtcaatgtta attgttgctg attctaaagg  10140
gggggttttt tttaggcagt atagagttgg gagatttggg aaagatttta ggatacataa  10200
atttagaacg atgtttatcg attcagaaaa aaaaggacgg ataacagttg gtcaagatgc  10260
tcgggtaacc agagttggat ggtatttacg gaagtacaaa atcgatgagc ttcctcaatt  10320
gatagatgtt ctttctggaa caatgagttt ggttggccca agaccggaag tgagggagtt  10380
tattgatgag tatcctgatg atataaggga aaaagtttta tcggttaggc cagggataac  10440
tgacttagca tctatagaaa tggtagatga aaatgagatt ttgtctagtt atgatgaccc  10500
acgtagggct tatatagata taattcttcc aatcaagcaa agatattatt tagattatgt  10560
tgctaacaat tcagtaaagt atgattgtgt gataatttgg aaaactatta ttaagatttt  10620
gtcgcgataa taaggtagtg taggatgatt gatagaatat tggagctgcc aagaattgtt  10680
aagagaggta tcatcatctg cattgatgta gttatggtga tattctcatt ttggttgtct  10740
tattggttga ggcttgatga gcaaacggct tttcttagtg caccgatgtg gtttgctgca  10800
gctattctta ccatatttac cgtgtttata tttatcagga ttgggcttta tcgggcagtc  10860
ttacggtatg ttagtgcaaa gataatgttg ctaataccag ttggtattct ggcctcaacg  10920
ttatctcttg tcgttatatc atattcgcta tccataatgt tgccgcgcac tgttgtcgga  10980
atttattttt tggttttact tttactgaca tcaggctcta gattgctttt tagaatgata  11040
cttaactatg gagttaaggg tagtgcgcct gttttgattt atggcgctgg tgaatctggc  11100
cgacaattat tgccagcatt aatgcaggca aaagaatatt ttcctgtggc atttgtggat  11160
gataatcctc gcttgcataa ggctgtcatt catggtgtaa cagtttatcc ctcggataaa  11220
ctgagttacc ttgtagatcg ctatggtata aagaaaattc ttttggcgat gccgagcgtc  11280
agtaagtcac aaaggcagaa agtgattact cgtttagagc atctaccgtg tgaagttctc  11340
tctattccgg gtatggtcga tttagtcgaa ggtcgagcac aaatcagtaa tctaaaaaaa  11400
gtatcgattg atgacttact aggtcgtgat ccggttgctc ctgatgccaa attgatggcc  11460
gaaaacatta ctggcaaagc cgttatggtc actggggcgg gaggctcgat cggctctgag  11520
ctttgtcgtc aaattgttcg atataagccg gccaaattgg ttctatttga actgtctgaa  11580
tatgccctct acgctattga gaaagagctc tcggcgctgt gcgacaaaga agttttgaat  11640
gttccagtga tccctctgtt gggctcggtg cagcgtcaga atcgcttaca gatggtgatg  11700
aagtcctttg gtattcaaac ggtttatcat gcggccgctt ataaacatgt gcctctggtt  11760
gagcataatg tggtggaagg ggtacgtaat aacgtgtttg gtaccttgta ctgcgctgag  11820
tcagcgatcg aaagtggcgt tgaaactttt gtgttgattt ccaccgataa agcggtgcgc  11880
ccgaccaaca ctatggggac aactaagcgt ctggccgaat tggtattgca ggctttgtct  11940
gcacggcaaa gccaaactcg cttttgtatg gtgcgatttg gtaatgtact cggttcttcg  12000
ggctctgtcg tgccgttgtt tgaaaaacag attgcccaag gtgggccagt taccttgact  12060
```

```
catcgtgaca ttattcgcta tttcatgaca attccggaag catcacagtt ggtgattcaa  12120

gcgggggcga tggggcatgg cggcgatgtc tttgtcttag acatgggcga tccggtcaag  12180

atttatgact tagccaaacg catgatccgg ttaagtggct tgagtgtacg ggatgataaa  12240

aatccagatg gcgatattgc cattgaagtt acgggattac gtccagggga gaaactgtat  12300

gaagaattac tgattggtga ttcagttcaa ggtacctctc atccacgaat tatgacggcc  12360

aacgaagtga tgctaccgtg gcaggatcta tcgctcttac ttaaagagct ggatcaagct  12420

tgtcatgact ttgatcatga gcgaattcgc agtttgttgt tacaagcacc agcggcattc  12480

aatccaactg atgatatttg cgatctagtt tggcagcaga aaaaatcgct gttatcacaa  12540

gcgagcaatg tcattcgcct gtgattgctt aggtttaacc ttccacacca attcttcacc  12600

tctcttacaa atccccgcta ggcggtacat cgtgaccgcc tttagcctga tgcctgctct  12660

ttaacaaaca ggacatcagt gtatgtttaa ac                                12692
```

<210> SEQ ID NO 5
<211> LENGTH: 12421
<212> TYPE: DNA
<213> ORGANISM: Shigella sonnei
<220> FEATURE:
<221> NAME/KEY: misc_feature
<223> OTHER INFORMATION: 12.4 HindIII fragment from AF294823 (SEQ ID NO:7 positions 1310-13730) encoding a portion of the Shigella sonnei O antigen gene cluster

<400> SEQUENCE: 5

```
aagcttgatc aaatagctca tattcagcga gatttaacaa ctgcggaaca agccggaatc     60

attgattatc gctctagcaa aggcggcttc gataatgcgc aaagtagcta taagttcttg    120

ctcggcgaaa aactgttatc agcagagcta aaagcaacta aagatgcgcc aattatttac    180

ccatttagat attacgaagt gaaacgtcaa attgatgagt tagaaggaat gttacgcgat    240

aacattcagg cgcaagcata tcgatatcaa atgaagccat ctgagccagt tataaaagac    300

aaacccaaca aagcattaat tttgattctt ggtgcattac caggggcaat gtttgctata    360

gttggtacat tagtttatgc gacattaaaa gataaaacca agttagatta aactgggtta    420

cgtattgttg tgtcaatgcg aaatagatgt tctatgtgca ctttatgatg gataagaaaa    480

tgaaattcga tactttgaat gcgaaaattg ggattatagg ccttggttat gttggattgc    540

ctcttgctgt tgagtttgga aagaaagtaa cgacgattgg atttgatatt aataagtctc    600

gtattgatga attacgaaat ggtcacgata gtacattaga gtgctcaaat ttagagttgt    660

tagaagcaac taaattgacg tacgcctgtt cattagatgc actaaaagag tgtaatgtat    720

ttattgtaac tgttccaact ccaattgata aacataaaca gccagatcta acacctctaa    780

ttaaagcatc tgaaacattg ggtaagataa taaagaaagg cgatgttatt atttatgagt    840

caacagttta ccctggagcg acagaagaag attgtatacc agttgtagag aaagtatcag    900

gtcttaagtt taatattgat ttttttgccg gttattcacc tgagcgtatt aatcctgggg    960

ataaagagca tcgtgtaact aatatcctta aggtgaccag tggatctaca ccggatgttg   1020

ctgagtatgt agatcagcta tataaattaa taattactgt cggtacgcat aaagcatcat   1080

cgataaaagt agcagaggct gcaaaagtaa ttgaaaacac gcagcgagat gtcaatattg   1140

cattgattaa tgagttatct attatattta ataagttagg gattgatacc ttagaggttc   1200

ttgaggctgc aggtacgaag tggaattttt taccttttag gcccggttta gtaggtggcc   1260

actgtatagg tgtagatcct tattatctta cacataaagc gcaaagtgtc ggctatcatc   1320
```

```
cggagatgat tttagccgga cgtcgtttaa atgatagtat ggggcagtat gtcgtttccc   1380
agttagtcaa aaaaatgttg aaacaacgga ttcaagttga aggggcgaat gtgttagtga   1440
tggggcttac atttaaagag aattgcccag atctacgaaa cactaaagtg attgatatta   1500
tttcagagtt aaaagaatac aatatcaata tagatattat agatccatgg tgttctaccg   1560
atgaggcaca acatgaatat ggattaactt tatgtgaaga tcctaaagtt aatcattatg   1620
atgcaataat tatcgctgtt gcacacaatg agtttcgcga gatgggagag agcgctattc   1680
gtgcattagg taaagacgag cacgttttgt tcgatttaaa atatgtgctt gataaaaaaa   1740
gtatcgatat gcgcttgtaa gagtgattaa aaaaatcaaa tcctctttga tatgatacac   1800
ctcagcattt tatgctaggt ttagcacttg attaatatac atggatattt atatgtctcg   1860
ctatgaagag attacacagc agttaatttt ttcaccgaaa acttggttaa ttactggtgt   1920
cgctggcttt ataggatcaa atcttttaga aaagttactt aaattaaacc aggttgttat   1980
tgggttagat aacttttcca cgggacatca atataatctt gatgaagtta aaacattagt   2040
ttccactgaa cagtggagtc gattttgctt tatagaaggt gatattcgag atctcactac   2100
ctgtgagcaa gttatgaaag gtgttgatca tgtcttacat caggctgcgc taggttctgt   2160
acctcgttca attgttgatc ctataacaac caatgcaact aatattactg gatttttgaa   2220
tatcttacat gcggctaaaa atgcacaagt acaaagtttt acttatgctg catcaagctc   2280
aacttatgga gatcatcccg cactaccaaa agtagaggaa aacattggta atccactttc   2340
tccttatgca gttactaaat atgttaacga gatttatgct caggtatatg ctcgaacata   2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgatttttgt tatatagata atgttataca   2580
aatgaatata ttatctgcat tagcgaagga cagtgctaaa gataatatat ataatgttgc   2640
agttggtgat agaacaacgt taaatgaatt atctggttac atttatgatg agcttaattt   2700
aattcaccat atcgataaat tgagcattaa gtatagagag tttagatctg gagatgttag   2760
gcattctcag gctgatgtta ctaaggctat agatttacta aagtatagac caaatataaa   2820
aatcagagag ggattacgac tttcaatgcc gtggtatgtg agatttttaa aaggctaaat   2880
tatattaaca tgaataaata atctatttca cctctgttat taatgcaggg gtgaaaatcc   2940
atgtatttat tctaaatggt cagtgtatgt ttagaaaaat gattgatgca ggtggtacat   3000
ttttacttaa agcaatattt caaataggag tttttgttta tttcacacat gtgtcagata   3060
ttactacatt tggtattatt agttatgtgt ttactgttta ttggtttgtg cttaacttct   3120
ctgattatgg atttagaaca aaattagtga aagatatttc tgataatagt tattctgcat   3180
cagaattatt atcaagaagt gatggagtta aaacatatgt ttttttcttc atttttataa   3240
tcttcatgtt ttattcttat gtttctgatt caatttcatt aactctgctt gtttatattt   3300
catctgcata ttttgtttgt atttcaagtg gtagatttag cttgctacag gctgttggtc   3360
ggtttagatg tgaattatat ataaatatct actcaacaat tatatatatt gggtgtaatt   3420
tatttttatc tctgtttatc gaacctctat attatagtgc gatatcaata ttcatatact   3480
caatttcgct tttggttttc tcatcacata aatgcaatgt gccatgtttt catataaaaa   3540
gaccaagtat tttagtttat aaagattttt tggatgcaac tccgttcgct attctggtgt   3600
tactaaatgt tgttttatct agtattgacc tttttatatt aaaagaatat ttctcttata   3660
```

```
atagtgttgc tatatatcag gtggtaacta gggttaatac cggtctaata atagtgttta   3720
atgttattta tactgtttta ttgccttcat tttcttatta tctgaaaaat tctgaatggg   3780
gtaatataag gaaattacaa cgatatatat cactgttagt cttattacta tgtttatgct   3840
attatttttt tggcatctat ttcgtaggga tattgtttgg tgatgagtat aaggtaatat   3900
cttctgcaac atttttgata atgtttatgg ctcttattaa atataatttt tggctaataa   3960
atgaacttta tcttgtgtgt agtggaaatc aaagcgagcg agttaaatcg tattgtattg   4020
gtgtggtcat ttcaatggcg gttttctttt attttatacc tcggtatgga tggagtgggg   4080
cggtttttgg aagtgccatt gcaacattag taattggaat attttatatt atttctgtga   4140
aaaaagattg tgggaaaatt cttcatgata agtattcact aatgatgatc tttgtcccaa   4200
ttttctttta ttttattatt aatggtcagc agcggttgtt atattaatat gttgtggttt   4260
tatatcgttc cattaatatg tttagactcg attggaagcc taataaaggt taagtatgtt   4320
aatataccta tatcctgtac ttttgttatt taatatcctt ccggtttttt tttatggaca   4380
aatgaactct gatttagagc gtttttttgg agttcctatt ggctatattc cagatctaat   4440
attttatttc tttgttgttt taacatctat aataacgttg aggtttcacg tttctctgtg   4500
gacaaagaaa ttattatttt taggcatcat attcctgatt tatatcagca ttcagatgtt   4560
gttgttatca gcggatatat caggtgtcgt aattttatta tcgttttttt ctaattttat   4620
agctttggtt cttttggtgt cattttgcat tggtaaagat gagctttatt taactcattc   4680
ggttagaaat ataaatgttg taatgtgttt tggtattatc tgtggagttg taaaattatt   4740
tattggttat tctgaagata gtaattttat agtttattta aatagaaatg ccaccgcaat   4800
tatagtagtg tgcttttatt gtgtatattc atacttttat cgtggtcgaa agtcttggta   4860
tgtctcatct gtattgtact ctctgttctt tctttttctg gatagccgag caggaataat   4920
atcatttgct atatcgttgt tttttgtttt tcttcagtta acaaagaagg aaaagttatt   4980
aatatcattg tttttgttc ctcttctaac tttaggtatt tcttttactg atataggcac   5040
tcgtcttgaa cgaatgctgt cttcgtcaca ggttatattc tctggtggta acactcttac   5100
aaaaagtcag aatgattatc gtcgagttga gttagtattt attggggttg atgttttaaa   5160
agaaaattat ttaattggca ctggattagg tgttgcaaat tatgtaaagg ctatagataa   5220
aaagttttta ggaagtacca actttgggtt ggcgcataat ttttatttat cttattcggc   5280
tcagttaggg attattggtt ttattttgct tatttctgta ttttatataa tgctgtctcc   5340
aatttttaaa tgcggagggt atattggtaa aggatgcgtt tttgctttgg ctttctatgt   5400
ctttttaat gagtatatat tgacgccagc gatatatatt tatatttcta ttttttatc   5460
ggtggttttt atacgtaatt ctaaatagct gcgcggaata gtagatcact ttgagggaac   5520
ttagcccgga ttgtgcgatc tgatcaatcg ccaaatcaaa acaaatcacc aaccggactg   5580
agcaatgccg atcatagcac caatttcccg tgacgaacga cgcctgatgc agaaagccat   5640
ccataaaaca cacgataaaa attatgcccg cagactgact gccatgctga tgctgcaccg   5700
gggcgaccgt gtcagcgacg ttgccagaac gctctgctgc gcccgttcct ctgttggacg   5760
ctggattaac tggttcacgc agtcgggtgt tgagggactg aaatcattac ctgccgggcg   5820
tgcccgtcgc tggccgtttg agcatatctg cacactgtta cgtgagctgg taaaacattc   5880
tcccggcgac tttggctacc agcgttcacg ctggagtaca gaactgctgg caataaaaat   5940
caatgagata accggttgcc agttaaatgc cggaaccgtt cgccgctggt tgccgtctgc   6000
ggggattgtg tggcgaaggg ctgcgccaac tctgcgtatc cgtgacccgc ataaagatga   6060
```

```
aaagatggca gcaatccata aagcactgga cgaatgcagc gcagagcatc cggtctttta   6120
tgaagatgaa gtggatatcc atcttaatcc caaaatcggt gcggactggc aactgcgcgg   6180
acagcaaaaa cgggtggtca cgccgggaca gaatgaaaaa tattatctgg ccggagcgct   6240
gcacagcggg acaggtaaag tcagctgtgt gggcggcaac agcaaaagtt cggcgctgtt   6300
catcagcctg ctgaagcggc ttaaagcgac ataccgtcgg gcgaaaacca tcacgctgat   6360
cgtggacaac tacattatcc acaaaagccg ggaaacacag agctggctga aggagaaccc   6420
gaagttcagg gtcatttatc agccggttta ctcgccatgg atgaatcatg ttgaacggct   6480
atggcaggca cttcacgaca caataacgcg taatcatcag tgcagctcaa tgtggcaact   6540
gttgaaaaaa gttcgccatt ttatggaaac cgtcagccca ttccccggag gcaaacatgg   6600
gctggcaaaa gtgtagcggt attaagcgca gctatttagg atgagaatat gttgttagaa   6660
tatgttgaaa gaaaaatttc cttagccttg agtaagtatc ctaaggtaag ggatgttatt   6720
aagttctttt atttatatat cgcatcatta ttcggaatta ttttgaataa aaataagacg   6780
gttattcaat caaaaatata cgagatttca attgatgatt ctgaagaatc attttttggc   6840
tattatgacc atagtccaat gagctctaat gggcggtacg tattgttcca ctctagtgcg   6900
tttagcacta aacgacatcc aaagaaagtt aagtatatat ctatttgcgt aaaagacctt   6960
cttaataaca aagtttataa gctatatgat acgcgagcat ttaattggca gcagggaagc   7020
cgattaatgt ggattgatga tgacaatata atttttaatg actatgaaaa taatggatac   7080
attagtgttg tctattcttt gtctttgatg aaggttataa aaaaaataaa ctatccgatt   7140
tatgatgtga ataattacaa ggctgtgacg ttagatttct catggctggc taaatatgat   7200
agcgattatg gttattataa taaaaaatca ttttctacag atatttcaat cattaatttg   7260
aatacggggg gaatagaatt atttttatcc ttagacgaaa tgctaaagag aactaatttt   7320
aaatgtaata ttgatgttga acatgtggtc aatcatttta tgtttgctcc cgatggacgt   7380
tccgttatgt tcatacatcg atactataca cctaaaggaa agcgtgaaag gttaatacat   7440
tggaatttaa taaatgataa tgttcgagtc ctaataaatg aatcgattat tagtcattgt   7500
tgttggaatg ggaatgatga aattataggt ttttttggtg cagaaataga ttcgctaaat   7560
tattatagat tgtcaattga atcctgtaat acagagaaat tgttttttga tgcaagaaaa   7620
tattctgatg gacatcctac tatagttcat aatagatata ttatatctga tacttaccca   7680
gataaaaata gaattaaaaa gttgtttgtt tatgaccttg tcaaaaatga ttatcgcgag   7740
cttggattat tttatgagtc aatgagtttt ttttcttatt ctcgatgtga cttacatcca   7800
aggatctcgg ttgataatag atttttgttt gttgattcag ttcactcagg gaaaagaaaa   7860
ctatatttta tgaggagtgg tatttgtgag tgatgttcta gtatctttaa ttatagtttg   7920
ctttaatgca gagaagtata ttgaaaaatc tcttttggca tttattaatc aagatgttgg   7980
attagataaa tttgaattga ttattgtaga tggggattca tctgataata caatatctat   8040
tgttcaggat gttttttcta aacatagcaa cattaagcat aaaattatca ataataaaaa   8100
aagaactctt gctacgggtt ggaatattgg ggtgctagaa gctaatggta agtttgtgtg   8160
tagagttgat gcacatagtg atattccaaa taactatata tctaaattat tagatgatta   8220
ttttaatatt atgcagtttg atgatagcgt tgttggtgtt ggaggtgtat taactaattc   8280
ttataaaact aagtttggtt caattgtagc ggatttttat gcatcgaaat ttggtgttgg   8340
taattctcca tttaggtgcg tagacaaaaa taatcgacta aaaaaaacag atacagctgt   8400
```

```
ctttgcttta tataataaag atgtgttttt tgatgttgga ctttttaatg aagtattaga   8460
tagaaatcaa gatattgatt ttcataagag agttttaagc aataatttgt cattatatac   8520
agataatagt ttatttgttg agtattatgt tagagataat tttaaagatt tcataaagaa   8580
aggttttctt gatggttttt gggttgttat gtctggagca tattatttta gacatatagt   8640
gccacttttt tttgttttgt atttaattgt atctttttct cttttctttg ctactggtga   8700
ttatatatat ttatcttttt tattttttta ttttcttatt tctattttgt tttcaattcg   8760
agatgggcga agttttatag gtagagtatt tcttcctttt atatttttgt cttatcatat   8820
ttcttatgga tgtggatcgt tattatcttt tttgaaaagg tattttaaat gaaaaatttt   8880
attccttttg cgttacctga aattggcgaa gaagaaattg cagaggtaat tgactcttta   8940
cgttcaggtt ggattacgac aggtcctaag gctaagcaat ttgaacaaga attttctaat   9000
tacctaggag cgaacgttca atcattagct gttaactctg ctacgtcggg cttacatttg   9060
gctcttgaag ctgttggcgt aaagccggga gaccaagtta ttgtcccatc atatacattc   9120
actgctactg ccgaaattgt caggtacctt ggtgctgatc ctgtaattgt tgatgtagat   9180
cgtaaaacat ttaatatatc agttgatgcc attgagaagg ctattactaa tgaaacaaag   9240
gcgattattc cagtacactt cgctggatta gcttgtgaca tggattcaat cttatcaatt   9300
gctaaaaaat atgacctaaa ggttgtcgag gatgccgctc atgcatttcc tacaacatat   9360
aaaggaagta agataggaac gcttgattca gatgctacgg tttttagctt ctacgccaat   9420
aaaactatga caaccggtga aggcggaatg gttgtttcaa aaaataaaga tataattgag   9480
cgttgtaagg taatgcgttt acatggaatc agtcgtgacg cttttgaccg gtaccagtct   9540
aaaactcctt cttggtttta tgaggttgta gctccagggt ttaaatacaa tatgcctgat   9600
atctgtgcgg caatcggtat tcatcaactt agaaagatcg atgattttca gaaaaaacgt   9660
caacgaatgg caaaaattta cgatgatgcg ttaaaagaat tgccacttga attgcctgaa   9720
tggcctacta atgctagtga tattcatgct tggcatctat atcctatccg cttaaaaact   9780
gattcggcta ttaatcgcga tgattttatt aagaagttat cagatcttgg aattggttgt   9840
tctgtccatt ttataccgtt gcataagcaa ccggtttggc gtgatacata taatttgaac   9900
gccagtgact ttccagtttc tgaggagtgt tatttaaatg aaatatctat tcctctttat   9960
actaaaatga cggatcaaga tcagttgttc gttatcaaat cgattagaca attatttatg  10020
taatggtatt ttatattaaa tgaaacgtat ttttgatgtt atcgtggcag gcttaggcct  10080
gctttttcta tttcctgttt ttatcattgt gtcaatgtta attgttgctg attctaaagg  10140
gggggttttt tttaggcagt atagagttgg gagatttggg aaagatttta ggatacataa  10200
atttagaacg atgtttatcg attcagaaaa aaaaggacgg ataacagttg gtcaagatgc  10260
tcgggtaacc agagttggat ggtatttacg gaagtacaaa atcgatgagc ttcctcaatt  10320
gatagatgtt ctttctggaa caatgagttt ggttggccca agaccggaag tgagggagtt  10380
tattgatgag tatcctgatg atataaggga aaaagtttta tcggttaggc cagggataac  10440
tgacttagca tctatagaaa tggtagatga aaatgagatt ttgtctagtt atgatgaccc  10500
acgtagggct tatatagata taattcttcc aatcaagcaa agatattatt tagattatgt  10560
tgctaacaat tcagtaaagt atgattgtgt gataatttgg aaaactatta ttaagatttt  10620
gtcgcgataa taaggtagtg taggatgatt gatagaatat tggagctgcc aagaattgtt  10680
aagagaggta tcatcatctg cattgatgta gttatggtga tattctcatt ttggttgtct  10740
tattggttga ggcttgatga gcaaacggct tttcttagtg caccgatgtg gtttgctgca  10800
```

```
gctattctta ccatatttac cgtgtttata tttatcagga ttgggcttta tcgggcagtc  10860
ttacggtatg ttagtgcaaa gataatgttg ctaataccag ttggtattct ggcctcaacg  10920
ttatctcttg tcgttatatc atattcgcta tccataatgt tgccgcgcac tgttgtcgga  10980
atttattttt tggttttact tttactgaca tcaggctcta gattgctttt tagaatgata  11040
cttaactatg gagttaaggg tagtgcgcct gttttgattt atggcgctgg tgaatctggc  11100
cgacaattat tgccagcatt aatgcaggca aaagaatatt ttcctgtggc atttgtggat  11160
gataatcctc gcttgcataa ggctgtcatt catggtgtaa cagtttatcc ctcggataaa  11220
ctgagttacc ttgtagatcg ctatggtata aagaaaattc ttttggcgat gccgagcgtc  11280
agtaagtcac aaaggcagaa agtgattact cgtttagagc atctaccgtg tgaagttctc  11340
tctattccgg gtatggtcga tttagtcgaa ggtcgagcac aaatcagtaa tctaaaaaaa  11400
gtatcgattg atgacttact aggtcgtgat ccggttgctc ctgatgccaa attgatggcc  11460
gaaaacatta ctggcaaagc cgttatggtc actggggcgg gaggctcgat cggctctgag  11520
ctttgtcgtc aaattgttcg atataagccg gccaaattgg ttctatttga actgtctgaa  11580
tatgccctct acgctattga gaaagagctc tcggcgctgt gcgacaaaga agttttgaat  11640
gttccagtga tccctctgtt gggctcggtg cagcgtcaga atcgcttaca gatggtgatg  11700
aagtcctttg gtattcaaac ggtttatcat gcggccgctt ataaacatgt gcctctggtt  11760
gagcataatg tggtggaagg ggtacgtaat aacgtgtttg gtaccttgta ctgcgctgag  11820
tcagcgatcg aaagtggcgt tgaaactttt gtgttgattt ccaccgataa agcggtgcgc  11880
ccgaccaaca ctatggggac aactaagcgt ctggccgaat tggtattgca ggctttgtct  11940
gcacggcaaa gccaaactcg cttttgtatg gtgcgatttg gtaatgtact cggttcttcg  12000
ggctctgtcg tgccgttgtt tgaaaaacag attgcccaag gtgggccagt taccttgact  12060
catcgtgaca ttattcgcta tttcatgaca attccggaag catcacagtt ggtgattcaa  12120
gcgggggcga tggggcatgg cggcgatgtc tttgtcttag acatgggcga tccggtcaag  12180
atttatgact tagccaaacg catgatccgg ttaagtggct tgagtgtacg ggatgataaa  12240
aatccagatg gcgatattgc cattgaagtt acgggattac gtccagggga gaaactgtat  12300
gaagaattac tgattggtga ttcagttcaa ggtacctctc atccacgaat tatgacggcc  12360
aacgaagtga tgctaccgtg gcaggatcta tcgctcttac ttaaagagct ggatcaagct  12420
t                                                                  12421
```

<210> SEQ ID NO 6
<211> LENGTH: 11022
<212> TYPE: DNA
<213> ORGANISM: Shigella sonnei
<220> FEATURE:
<221> NAME/KEY: misc_feature
<223> OTHER INFORMATION: O antigen

<400> SEQUENCE: 6

```
aagcttgatc aaatagctca tattcagcga gatttaacaa ctgcggaaca agccggaatc     60
attgattatc gctctagcaa aggcggcttc gataatgcgc aaagtagcta taagttcttg    120
ctcggcgaaa aactgttatc agcagagcta aaagcaacta aagatgcgcc aattatttac    180
ccatttagat attacgaagt gaaacgtcaa attgatgagt tagaaggaat gttacgcgat    240
aacattcagg cgcaagcata tcgatatcaa atgaagccat ctgagccagt tataaaagac    300
aaacccaaca aagcattaat tttgattctt ggtgcattac caggggcaat gtttgctata    360
```

```
gttggtacat tagtttatgc gacattaaaa gataaaacca agttagatta aactgggtta    420
cgtattgttg tgtcaatgcg aaatagatgt tctatgtgca ctttatgatg gataagaaaa    480
tgaaattcga tactttgaat gcgaaaattg ggattatagg ccttggttat gttggattgc    540
ctcttgctgt tgagtttgga aagaaagtaa cgacgattgg atttgatatt aataagtctc    600
gtattgatga attacgaaat ggtcacgata gtacattaga gtgctcaaat ttagagttgt    660
tagaagcaac taaattgacg tacgcctgtt cattagatgc actaaaagag tgtaatgtat    720
ttattgtaac tgttccaact ccaattgata aacataaaca gccagatcta acacctctaa    780
ttaaagcatc tgaaacattg ggtaagataa taaagaaagg cgatgttatt atttatgagt    840
caacagttta ccctggagcg acagaagaag attgtatacc agttgtagag aaagtatcag    900
gtcttaagtt taatattgat ttttttgccg gttattcacc tgagcgtatt aatcctgggg    960
ataaagagca tcgtgtaact aatatcctta aggtgaccag tggatctaca ccggatgttg   1020
ctgagtatgt agatcagcta tataaattaa taattactgt cggtacgcat aaagcatcat   1080
cgataaaagt agcagaggct gcaaaagtaa ttgaaaacac gcagcgagat gtcaatattg   1140
cattgattaa tgagttatct attatattta ataagttagg gattgatacc ttagaggttc   1200
ttgaggctgc aggtacgaag tggaattttt taccttttag gcccggttta gtaggtggcc   1260
actgtatagg tgtagatcct tattatctta cacataaagc gcaaagtgtc ggctatcatc   1320
cggagatgat tttagccgga cgtcgtttaa atgatagtat ggggcagtat gtcgtttccc   1380
agttagtcaa aaaaatgttg aaacaacgga ttcaagttga aggggcgaat gtgttagtga   1440
tggggcttac atttaaagag aattgcccag atctacgaaa cactaaagtg attgatatta   1500
tttcagagtt aaaagaatac aatatcaata tagatattat agatccatgg tgttctaccg   1560
atgaggcaca acatgaatat ggattaactt tatgtgaaga tcctaaagtt aatcattatg   1620
atgcaataat tatcgctgtt gcacacaatg agtttcgcga gatgggagag agcgctattc   1680
gtgcattagg taaagacgag cacgttttgt tcgatttaaa atatgtgctt gataaaaaaa   1740
gtatcgatat gcgcttgtaa gagtgattaa aaaaatcaaa tcctctttga tatgatacac   1800
ctcagcattt tatgctaggt ttagcacttg attaatatac atggatattt atatgtctcg   1860
ctatgaagag attacacagc agttaatttt ttcaccgaaa acttggttaa ttactggtgt   1920
cgctggcttt ataggatcaa atcttttaga aaagttactt aaattaaacc aggttgttat   1980
tgggttagat aacttttcca cgggacatca atataatctt gatgaagtta aaacattagt   2040
ttccactgaa cagtggagtc gattttgctt tatagaaggt gatattcgag atctcactac   2100
ctgtgagcaa gttatgaaag gtgttgatca tgtcttacat caggctgcgc taggttctgt   2160
acctcgttca attgttgatc ctataacaac caatgcaact aatattactg gatttttgaa   2220
tatcttacat gcggctaaaa atgcacaagt acaaagtttt acttatgctg catcaagctc   2280
aacttatgga gatcatcccg cactaccaaa agtagaggaa aacattggta atccactttc   2340
tccttatgca gttactaaat atgttaacga gatttatgct caggtatatg ctcgaacata   2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgatttttgt tatatagata atgttataca   2580
aatgaatata ttatctgcat tagcgaagga cagtgctaaa gataatatat ataatgttgc   2640
agttggtgat agaacaacgt taaatgaatt atctggttac atttatgatg agcttaattt   2700
```

```
aattcaccat atcgataaat tgagcattaa gtatagagag tttagatctg gagatgttag   2760
gcattctcag gctgatgtta ctaaggctat agatttacta aagtatagac caaatataaa   2820
aatcagagag ggattacgac tttcaatgcc gtggtatgtg agatttttaa aaggctaaat   2880
tatattaaca tgaataaata atctatttca cctctgttat taatgcaggg gtgaaaatcc   2940
atgtatttat tctaaatggt cagtgtatgt ttagaaaaat gattgatgca ggtggtacat   3000
ttttacttaa agcaatattt caaataggag tttttgttta tttcacacat gtgtcagata   3060
ttactacatt tggtattatt agttatgtgt ttactgttta ttggtttgtg cttaacttct   3120
ctgattatgg atttagaaca aaattagtga aagatatttc tgataatagt tattctgcat   3180
cagaattatt atcaagaagt gatggagtta aaacatatgt ttttttcttc atttttataa   3240
tcttcatgtt ttattcttat gtttctgatt caatttcatt aactctgctt gtttatattt   3300
catctgcata ttttgtttgt atttcaagtg gtagatttag cttgctacag gctgttggtc   3360
ggtttagatg tgaattatat ataaatatct actcaacaat tatatatatt gggtgtaatt   3420
tatttttatc tctgtttatc gaacctctat attatagtgc gatatcaata ttcatatact   3480
caatttcgct tttggttttc tcatcacata aatgcaatgt gccatgtttt catataaaaa   3540
gaccaagtat tttagtttat aaagattttt tggatgcaac tccgttcgct attctggtgt   3600
tactaaatgt tgttttatct agtattgacc tttttatatt aaaagaatat ttctcttata   3660
atagtgttgc tatatatcag gtggtaacta gggttaatac cggtctaata atagtgttta   3720
atgttattta tactgtttta ttgccttcat tttcttatta tctgaaaaat tctgaatggg   3780
gtaatataag gaaattacaa cgatatatat cactgttagt cttattacta tgtttatgct   3840
attatttttt tggcatctat ttcgtaggga tattgtttgg tgatgagtat aaggtaatat   3900
cttctgcaac atttttgata atgtttatgg ctcttattaa atataatttt tggctaataa   3960
atgaacttta tcttgtgtgt agtggaaatc aaagcgagcg agttaaatcg tattgtattg   4020
gtgtggtcat ttcaatggcg gttttctttt attttatacc tcggtatgga tggagtgggg   4080
cggtttttgg aagtgccatt gcaacattag taattggaat attttatatt atttctgtga   4140
aaaaagattg tgggaaaatt cttcatgata agtattcact aatgatgatc tttgtcccaa   4200
ttttctttta ttttattatt aatggtcagc agcggttgtt atattaatat gttgtggttt   4260
tatatcgttc cattaatatg tttagactcg attggaagcc taataaaggt taagtatgtt   4320
aatataccta tatcctgtac ttttgttatt taatatcctt ccggtttttt tttatggaca   4380
aatgaactct gatttagagc gttttttttgg agttcctatt ggctatattc cagatctaat   4440
attttatttc tttgttgttt taacatctat aataacgttg aggtttcacg tttctctgtg   4500
gacaaagaaa ttattatttt taggcatcat attcctgatt tatatcagca ttcagatgtt   4560
gttgttatca gcggatatat caggtgtcgt aattttatta tcgttttttt ctaattttat   4620
agctttggtt cttttggtgt cattttgcat tggtaaagat gagctttatt taactcattc   4680
ggttagaaat ataaatgttg taatgtgttt tggtattatc tgtggagttg taaaattatt   4740
tattggttat tctgaagata gtaattttat agtttattta aatagaaatg ccaccgcaat   4800
tatagtagtg tgcttttatt gtgtatattc atacttttat cgtggtcgaa agtcttggta   4860
tgtctcatct gtattgtact ctctgttctt tcttttctg gatagccgag caggaataat   4920
atcatttgct atatcgttgt tttttgtttt tcttcagtta acaaagaagg aaaagttatt   4980
aatatcattg ttttttgttc ctcttctaac tttaggtatt tcttttactg atataggcac   5040
tcgtcttgaa cgaatgctgt cttcgtcaca ggttatattc tctggtggta acactcttac   5100
```

```
aaaaagtcag aatgattatc gtcgagttga gttagtattt attggggttg atgttttaaa   5160
agaaaattat ttaattggca ctggattagg tgttgcaaat tatgtaaagg ctatagataa   5220
aaagttttta ggaagtacca actttgggtt ggcgcataat tttatttat cttattcggc    5280
tcagttaggg attattggtt ttattttgct tatttctgta ttttatataa tgctgtctcc   5340
aatttttaaa tgcggagggt atattggtaa aggatgcgtt tttgctttgg ctttctatgt   5400
ctttttaat gagtatatat tgacgccagc gatatatatt tatatttcta tttttttatc    5460
ggtggttttt atacgtaatt ctaaatagct gcgcggaata gtagatcact ttgagggaac   5520
ttagcccgga ttgtgcgatc tgatcaatcg ccaaatcaaa acaaatcacc aaccggactg   5580
agcaatgccg atcatagcac caatttcccg tgacgaacga cgcctgatgc agaaagccat   5640
ccataaaaca cacgataaaa attatgcccg cagactgact gccatgctga tgctgcaccg   5700
gggcgaccgt gtcagcgacg ttgccagaac gctctgctgc gcccgttcct ctgttggacg   5760
ctggattaac tggttcacgc agtcgggtgt tgagggactg aaatcattac ctgccgggcg   5820
tgcccgtcgc tggccgtttg agcatatctg cacactgtta cgtgagctgg taaaacattc   5880
tcccggcgac tttggctacc agcgttcacg ctggagtaca gaactgctgg caataaaaat   5940
caatgagata accggttgcc agttaaatgc cggaaccgtt cgccgctggt tgccgtctgc   6000
ggggattgtg tggcgaaggg ctgcgccaac tctgcgtatc cgtgacccgc ataaagatga   6060
aaagatggca gcaatccata aagcactgga cgaatgcagc gcagagcatc cggtctttta   6120
tgaagatgaa gtggatatcc atcttaatcc caaaatcggt gcggactggc aactgcgcgg   6180
acagcaaaaa cgggtggtca cgccgggaca gaatgaaaaa tattatctgg ccggagcgct   6240
gcacagcggg acaggtaaag tcagctgtgt gggcggcaac agcaaaagtt cggcgctgtt   6300
catcagcctg ctgaagcggc ttaaagcgac ataccgtcgg gcgaaaacca tcacgctgat   6360
cgtggacaac tacattatcc acaaaagccg ggaaacacag agctggctga aggagaaccc   6420
gaagttcagg gtcatttatc agccggttta ctcgccatgg atgaatcatg ttgaacggct   6480
atggcaggca cttcacgaca caataacgcg taatcatcag tgcagctcaa tgtggcaact   6540
gttgaaaaaa gttcgccatt ttatggaaac cgtcagccca ttccccggag gcaaacatgg   6600
gctggcaaaa gtgtagcggt attaagcgca gctatttagg atgagaatat gttgttagaa   6660
tatgttgaaa gaaaaatttc cttagccttg agtaagtatc ctaaggtaag ggatgttatt   6720
aagttctttt atttatatat cgcatcatta ttcggaatta ttttgaataa aaataagacg   6780
gttattcaat caaaaatata cgagatttca attgatgatt ctgaagaatc attttttggc   6840
tattatgacc atagtccaat gagctctaat gggcggtacg tattgttcca ctctagtgcg   6900
tttagcacta aacgacatcc aaagaaagtt aagtatatat ctatttgcgt aaaagacctt   6960
cttaataaca aagtttataa gctatatgat acgcgagcat ttaattggca gcagggaagc   7020
cgattaatgt ggattgatga tgacaatata atttttaatg actatgaaaa taatggatac   7080
attagtgttg tctattcttt gtctttgatg aaggttataa aaaaaataaa ctatccgatt   7140
tatgatgtga ataattacaa ggctgtgacg ttagatttct catggctggc taaatatgat   7200
agcgattatg gttattataa taaaaaatca ttttctacag atatttcaat cattaatttg   7260
aatacggggg gaatagaatt atttttatcc ttagacgaaa tgctaaagag aactaatttt   7320
aaatgtaata ttgatgttga acatgtggtc aatcatttta tgtttgctcc cgatggacgt   7380
tccgttatgt tcatacatcg atactataca cctaaaggaa agcgtgaaag gttaatacat   7440
```

```
tggaatttaa taaatgataa tgttcgagtc ctaataaatg aatcgattat tagtcattgt   7500
tgttggaatg ggaatgatga aattataggt ttttttggtg cagaaataga ttcgctaaat   7560
tattatagat tgtcaattga atcctgtaat acagagaaat tgttttttga tgcaagaaaa   7620
tattctgatg gacatcctac tatagttcat aatagatata ttatatctga tacttaccca   7680
gataaaaata gaattaaaaa gttgtttgtt tatgaccttg tcaaaaatga ttatcgcgag   7740
cttggattat tttatgagtc aatgagtttt ttttcttatt ctcgatgtga cttacatcca   7800
aggatctcgg ttgataatag atttttgttt gttgattcag ttcactcagg gaaaagaaaa   7860
ctatatttta tgaggagtgg tatttgtgag tgatgttcta gtatctttaa ttatagtttg   7920
ctttaatgca gagaagtata ttgaaaaatc tcttttggca tttattaatc aagatgttgg   7980
attagataaa tttgaattga ttattgtaga tggggattca tctgataata caatatctat   8040
tgttcaggat gtttttttcta aacatagcaa cattaagcat aaaattatca ataataaaaa   8100
aagaactctt gctacgggtt ggaatattgg ggtgctagaa gctaatggta agtttgtgtg   8160
tagagttgat gcacatagtg atattccaaa taactatata tctaaattat tagatgatta   8220
ttttaatatt atgcagtttg atgatagcgt tgttggtgtt ggaggtgtat taactaattc   8280
ttataaaact aagtttggtt caattgtagc ggatttttat gcatcgaaat ttggtgttgg   8340
taattctcca tttaggtgcg tagacaaaaa taatcgacta aaaaaaacag atacagctgt   8400
ctttgcttta tataataaag atgtgttttt tgatgttgga ctttttaatg aagtattaga   8460
tagaaatcaa gatattgatt ttcataagag agttttaagc aataatttgt cattatatac   8520
agataatagt ttatttgttg agtattatgt tagagataat tttaaagatt tcataaagaa   8580
aggttttctt gatggttttt gggttgttat gtctggagca tattattttta gacatatagt   8640
gccacttttt tttgttttgt atttaattgt atctttttct cttttctttg ctactggtga   8700
ttatatatat ttatcttttt tatttttttta ttttcttatt tctattttgt tttcaattcg   8760
agatgggcga agttttatag gtagagtatt tcttcctttt atatttttgt cttatcatat   8820
ttcttatgga tgtggatcgt tattatcttt tttgaaaagg tattttaaat gaaaaatttt   8880
attccttttg cgttacctga aattggcgaa gaagaaattg cagaggtaat tgactcttta   8940
cgttcaggtt ggattacgac aggtcctaag gctaagcaat ttgaacaaga attttctaat   9000
tacctaggag cgaacgttca atcattagct gttaactctg ctacgtcggg cttacatttg   9060
gctcttgaag ctgttggcgt aaagccggga gaccaagtta ttgtcccatc atatacattc   9120
actgctactg ccgaaattgt caggtacctt ggtgctgatc ctgtaattgt tgatgtagat   9180
cgtaaaacat ttaatatatc agttgatgcc attgagaagg ctattactaa tgaaacaaag   9240
gcgattattc cagtacactt cgctggatta gcttgtgaca tggattcaat cttatcaatt   9300
gctaaaaaat atgacctaaa ggttgtcgag gatgccgctc atgcatttcc tacaacatat   9360
aaaggaagta agataggaac gcttgattca gatgctacgg tttttagctt ctacgccaat   9420
aaaactatga caaccggtga aggcggaatg gttgtttcaa aaaataaaga tataattgag   9480
cgttgtaagg taatgcgttt acatggaatc agtcgtgacg cttttgaccg gtaccagtct   9540
aaaactcctt cttggtttta tgaggttgta gctccagggt ttaaatacaa tatgcctgat   9600
atctgtgcgg caatcggtat tcatcaactt agaaaagatcg atgattttca gaaaaaacgt   9660
caacgaatgg caaaaattta cgatgatgcg ttaaaagaat tgccacttga attgcctgaa   9720
tggcctacta atgctagtga tattcatgct tggcatctat atcctatccg cttaaaaact   9780
gattcggcta ttaatcgcga tgattttatt aagaagttat cagatcttgg aattggttgt   9840
```

```
tctgtccatt ttataccgtt gcataagcaa ccggtttggc gtgatacata taatttgaac   9900

gccagtgact ttccagtttc tgaggagtgt tatttaaatg aaatatctat tcctctttat   9960

actaaaatga cggatcaaga tcagttgttc gttatcaaat cgattagaca attatttatg  10020

taatggtatt ttatattaaa tgaaacgtat ttttgatgtt atcgtggcag gcttaggcct  10080

gctttttcta tttcctgttt ttatcattgt gtcaatgtta attgttgctg attctaaagg  10140

gggggttttt tttaggcagt atagagttgg gagatttggg aaagatttta ggatacataa  10200

atttagaacg atgtttatcg attcagaaaa aaaaggacgg ataacagttg gtcaagatgc  10260

tcgggtaacc agagttggat ggtatttacg gaagtacaaa atcgatgagc ttcctcaatt  10320

gatagatgtt ctttctggaa caatgagttt ggttggccca agaccggaag tgagggagtt  10380

tattgatgag tatcctgatg atataaggga aaaagtttta tcggttaggc cagggataac  10440

tgacttagca tctatagaaa tggtagatga aaatgagatt ttgtctagtt atgatgaccc  10500

acgtagggct tatatagata taattcttcc aatcaagcaa agatattatt tagattatgt  10560

tgctaacaat tcagtaaagt atgattgtgt gataatttgg aaaactatta ttaagatttt  10620

gtcgcgataa taaggtagtg taggatgatt gatagaatat tggagctgcc aagaattgtt  10680

aagagaggta tcatcatctg cattgatgta gttatggtga tattctcatt ttggttgtct  10740

tattggttga ggcttgatga gcaaacggct tttcttagtg caccgatgtg gtttgctgca  10800

gctattctta ccatatttac cgtgtttata tttatcagga ttgggcttta tcgggcagtc  10860

ttacggtatg ttagtgcaaa gataatgttg ctaataccag ttggtattct ggcctcaacg  10920

ttatctcttg tcgttatatc atattcgcta tccataatgt tgccgcgcac tgttgtcgga  10980

atttattttt tggttttact tttactgaca tcaggctcta ga                     11022
```

<210> SEQ ID NO 7
<211> LENGTH: 17986
<212> TYPE: DNA
<213> ORGANISM: Shigella sonnei
<220> FEATURE:
<221> NAME/KEY: misc_feature
<223> OTHER INFORMATION: GenBank Accession No. AF294823, Shigella sonnei O protein, Shigella sonnei O antigen gene cluster, complete sequence

<400> SEQUENCE: 7

```
ggtaatggct ccaacttatt gatagtgttt tatgttcaga taatgcccga tgactttgtc     60

atgcagctcc accgattttg agaacgacag cgacttccgt cccagccgtg ccaggtgctg    120

cctcagattc aggttatgcc gctcaattcg ctgcgtatat cgcttgctga ttacgtgcag    180

ctttcccttc aggcgggatt catacagcgg ccagccatcc gtcatccata tcaccacgtc    240

aaagggtgac agcaggctca taagacgccc cagcgtcgcc atagtgcgtt caccgaatac    300

gtgcgcaaca accgtcttcc ggagactgtc atacgcgtaa aacagccagc gctggcgcga    360

tttagccccg acatagcccc actgttcgtc catttccgcg cagacgatga cgtcactgcc    420

cggctgtatg cgcgaggtta ccgactgcgg cctgagtttt ttaagtgacg taaaatcgtg    480

ttgaggccaa cgcccataat gcgtgcagtt gcccggcatc caacgccatt catggccata    540

tcaatgattt tctggtgcgt accgggttgg gaagcggtgt aagtgaactg cagttgccat    600

gttttacggc agtgagagca gagatagcgc tgatgtccgg cagtgctttt gccgttacgc    660

accaccccgt cagtagctga acaggaggga cagctgatag aaacagaagc cactggagca    720

cctcaaaaac accatcatac actaaatcag taagttggca gcatcaccga ctacggggtt    780
```

```
agcagcagtg tatgccttta ccgcaaaaga gcagtggacg gctaaaacct atattcaagc    840
accacgtatt gctgaattag gcagctatct taaatttcac caagcgtatg cccgaatatt    900
aaatcaaccg ttagatacga atgcgttggc taatggattg ttttccgatt tgattttgat    960
tgctgaatcg ccagacacca aagttaaatt tctagagagt actgagtatt ataaaaagga   1020
aacaaataat ttatctactg accaagataa gaaaatttgg ttagctgagc aagcgaataa   1080
aggtcttgtg attacgccac caaaggaaaa gggaaataca agttactaca taatacaagc   1140
atcggcagac tcagcgcaag aggcatataa actactgcag ggatatctaa agaatgttaa   1200
taatcaagct gtaacattaa gtcttgatga gtttggtcaa aatgttaata ctcttttggt   1260
taatctaaat aaagaaatta ttgacataga tttccagaga aaatcagaaa agcttgatca   1320
aatagctcat attcagcgag atttaacaac tgcggaacaa gccggaatca ttgattatcg   1380
ctctagcaaa ggcggcttcg ataatgcgca aagtagctat aagttcttgc tcggcgaaaa   1440
actgttatca gcagagctaa aagcaactaa agatgcgcca attatttacc catttagata   1500
ttacgaagtg aaacgtcaaa ttgatgagtt agaaggaatg ttacgcgata acattcaggc   1560
gcaagcatat cgatatcaaa tgaagccatc tgagccagtt ataaaagaca aacccaacaa   1620
agcattaatt ttgattcttg gtgcattacc aggggcaatg tttgctatag ttggtacatt   1680
agtttatgcg acattaaaag ataaaaccaa gttagattaa actgggttac gtattgttgt   1740
gtcaatgcga aatagatgtt ctatgtgcac tttatgatgg ataagaaaat gaaattcgat   1800
actttgaatg cgaaaattgg gattataggc cttggttatg ttggattgcc tcttgctgtt   1860
gagtttggaa agaaagtaac gacgattgga tttgatatta ataagtctcg tattgatgaa   1920
ttacgaaatg gtcacgatag tacattagag tgctcaaatt tagagttgtt agaagcaact   1980
aaattgacgt acgcctgttc attagatgca ctaaaagagt gtaatgtatt tattgtaact   2040
gttccaactc caattgataa acataaacag ccagatctaa cacctctaat taaagcatct   2100
gaaacattgg gtaagataat aaagaaaggc gatgttatta tttatgagtc aacagtttac   2160
cctggagcga cagaagaaga ttgtatacca gttgtagaga aagtatcagg tcttaagttt   2220
aatattgatt tttttgccgg ttattcacct gagcgtatta atcctgggga taaagagcat   2280
cgtgtaacta atatccttaa ggtgaccagt ggatctacac cggatgttgc tgagtatgta   2340
gatcagctat ataaattaat aattactgtc ggtacgcata aagcatcatc gataaaagta   2400
gcagaggctg caaaagtaat tgaaaacacg cagcgagatg tcaatattgc attgattaat   2460
gagttatcta ttatatttaa taagttaggg attgatacct tagaggttct tgaggctgca   2520
ggtacgaagt ggaatttttt accttttagg cccggtttag taggtggcca ctgtataggt   2580
gtagatcctt attatcttac acataaagcg caaagtgtcg gctatcatcc ggagatgatt   2640
ttagccggac gtcgtttaaa tgatagtatg ggcagtatg tcgtttccca gttagtcaaa   2700
aaaatgttga aacaacggat tcaagttgaa ggggcgaatg tgttagtgat ggggcttaca   2760
tttaaagaga attgcccaga tctacgaaac actaaagtga ttgatattat ttcagagtta   2820
aaagaataca atatcaatat agatattata gatccatggt gttctaccga tgaggcacaa   2880
catgaatatg gattaacttt atgtgaagat cctaaagtta atcattatga tgcaataatt   2940
atcgctgttg cacacaatga gtttcgcgag atgggagaga gcgctattcg tgcattaggt   3000
aaagacgagc acgttttgtt cgatttaaaa tatgtgcttg ataaaaaaag tatcgatatg   3060
cgcttgtaag agtgattaaa aaaatcaaat cctctttgat atgatacacc tcagcatttt   3120
```

-continued

```
atgctaggtt tagcacttga ttaatataca tggatattta tatgtctcgc tatgaagaga   3180
ttacacagca gttaattttt tcaccgaaaa cttggttaat tactggtgtc gctggcttta   3240
taggatcaaa tcttttagaa aagttactta aattaaacca ggttgttatt gggttagata   3300
acttttccac gggacatcaa tataatcttg atgaagttaa aacattagtt tccactgaac   3360
agtggagtcg attttgcttt atagaaggtg atattcgaga tctcactacc tgtgagcaag   3420
ttatgaaagg tgttgatcat gtcttacatc aggctgcgct aggttctgta cctcgttcaa   3480
ttgttgatcc tataacaacc aatgcaacta atattactgg atttttgaat atcttacatg   3540
cggctaaaaa tgcacaagta caaagtttta cttatgctgc atcaagctca acttatggag   3600
atcatcccgc actaccaaaa gtagaggaaa acattggtaa tccactttct ccttatgcag   3660
ttactaaata tgttaacgag atttatgctc aggtatatgc tcgaacatat ggttttaaaa   3720
ctattggatt acgttatttt aatgtatttg gtcgtcgtca agatcctaat ggagcttatg   3780
ctgcagtaat tccaaaatgg acagcagcaa tgcttaaagg tgatgacgta tatattaatg   3840
gcgatggtga aacgagtcgt gatttttgtt atatagataa tgttatacaa atgaatatat   3900
tatctgcatt agcgaaggac agtgctaaag ataatatata taatgttgca gttggtgata   3960
gaacaacgtt aaatgaatta tctggttaca tttatgatga gcttaattta attcaccata   4020
tcgataaatt gagcattaag tatagagagt ttagatctgg agatgttagg cattctcagg   4080
ctgatgttac taaggctata gatttactaa agtatagacc aaatataaaa atcagagagg   4140
gattacgact ttcaatgccg tggtatgtga gatttttaaa aggctaaatt atattaacat   4200
gaataaataa tctatttcac ctctgttatt aatgcagggg tgaaaatcca tgtatttatt   4260
ctaaatggtc agtgtatgtt tagaaaaatg attgatgcag gtggtacatt tttacttaaa   4320
gcaatatttc aaataggagt tttgtttat ttcacacatg tgtcagatat tactacattt   4380
ggtattatta gttatgtgtt tactgtttat tggtttgtgc ttaacttctc tgattatgga   4440
tttagaacaa aattagtgaa agatatttct gataatagtt attctgcatc agaattatta   4500
tcaagaagtg atggagttaa aacatatgtt tttttcttca tttttataat cttcatgttt   4560
tattcttatg tttctgattc aatttcatta actctgcttg tttatatttc atctgcatat   4620
tttgtttgta tttcaagtgg tagatttagc ttgctacagg ctgttggtcg gtttagatgt   4680
gaattatata taaatatcta ctcaacaatt atatatattg ggtgtaattt atttttatct   4740
ctgtttatcg aacctctata ttatagtgcg atatcaatat tcatatactc aatttcgctt   4800
ttggttttct catcacataa atgcaatgtg ccatgttttc atataaaaag accaagtatt   4860
ttagtttata aagatttttt ggatgcaact ccgttcgcta ttctggtgtt actaaatgtt   4920
gttttatcta gtattgacct ttttatatta aaagaatatt tctcttataa tagtgttgct   4980
atatatcagg tggtaactag ggttaatacc ggtctaataa tagtgtttaa tgttatttat   5040
actgttttat tgccttcatt ttcttattat ctgaaaaatt ctgaatgggg taatataagg   5100
aaattacaac gatatatatc actgttagtc ttattactat gtttatgcta ttattttttt   5160
ggcatctatt tcgtagggat attgtttggt gatgagtata aggtaatatc ttctgcaaca   5220
tttttgataa tgtttatggc tcttattaaa tataattttt ggctaataaa tgaactttat   5280
cttgtgtgta gtggaaatca aagcgagcga gttaaatcgt attgtattgg tgtggtcatt   5340
tcaatggcgg ttttctttta ttttatacct cggtatggat ggagtggggc ggtttttgga   5400
agtgccattg caacattagt aattggaata ttttatatta tttctgtgaa aaaagattgt   5460
gggaaaattc ttcatgataa gtattcacta atgatgatct ttgtcccaat tttcttttat   5520
```

```
tttattatta atggtcagca gcggttgtta tattaatatg ttgtggtttt atatcgttcc   5580
attaatatgt ttagactcga ttggaagcct aataaaggtt aagtatgtta atatacctat   5640
atcctgtact tttgttattt aatatccttc cggttttttt ttatggacaa atgaactctg   5700
atttagagcg tttttttgga gttcctattg gctatattcc agatctaata ttttatttct   5760
ttgttgtttt aacatctata ataacgttga ggtttcacgt ttctctgtgg acaaagaaat   5820
tattattttt aggcatcata ttcctgattt atatcagcat tcagatgttg ttgttatcag   5880
cggatatatc aggtgtcgta attttattat cgtttttttc taattttata gctttggttc   5940
ttttggtgtc attttgcatt ggtaaagatg agctttattt aactcattcg gttagaaata   6000
taaatgttgt aatgtgtttt ggtattatct gtggagttgt aaaattattt attggttatt   6060
ctgaagatag taattttata gtttatttaa atagaaatgc caccgcaatt atagtagtgt   6120
gcttttattg tgtatattca tacttttatc gtggtcgaaa gtcttggtat gtctcatctg   6180
tattgtactc tctgttcttt ctttttctgg atagccgagc aggaataata tcatttgcta   6240
tatcgttgtt ttttgttttt cttcagttaa caaagaagga aaagttatta atatcattgt   6300
tttttgttcc tcttctaact ttaggtattt cttttactga tataggcact cgtcttgaac   6360
gaatgctgtc ttcgtcacag gttatattct ctggtggtaa cactcttaca aaaagtcaga   6420
atgattatcg tcgagttgag ttagtattta ttggggttga tgttttaaaa gaaaattatt   6480
taattggcac tggattaggt gttgcaaatt atgtaaaggc tatagataaa aagtttttag   6540
gaagtaccaa ctttgggttg gcgcataatt tttatttatc ttattcggct cagttaggga   6600
ttattggttt tattttgctt atttctgtat tttatataat gctgtctcca atttttaaat   6660
gcggagggta tattggtaaa ggatgcgttt ttgctttggc tttctatgtc ttttttaatg   6720
agtatatatt gacgccagcg atatatattt atatttctat tttttatcg gtggttttta   6780
tacgtaattc taaatagctg cgcggaatag tagatcactt tgagggaact tagcccggat   6840
tgtgcgatct gatcaatcgc caaatcaaaa caaatcacca accggactga gcaatgccga   6900
tcatagcacc aatttcccgt gacgaacgac gcctgatgca gaaagccatc cataaaacac   6960
acgataaaaa ttatgcccgc agactgactg ccatgctgat gctgcaccgg ggcgaccgtg   7020
tcagcgacgt tgccagaacg ctctgctgcg cccgttcctc tgttggacgc tggattaact   7080
ggttcacgca gtcgggtgtt gagggactga aatcattacc tgccgggcgt gcccgtcgct   7140
ggccgtttga gcatatctgc acactgttac gtgagctggt aaaacattct cccggcgact   7200
ttggctacca gcgttcacgc tggagtacag aactgctggc aataaaaatc aatgagataa   7260
ccggttgcca gttaaatgcc ggaaccgttc gccgctggtt gccgtctgcg gggattgtgt   7320
ggcgaagggc tgcgccaact ctgcgtatcc gtgacccgca taaagatgaa aagatggcag   7380
caatccataa agcactggac gaatgcagcg cagagcatcc ggtcttttat gaagatgaag   7440
tggatatcca tcttaatccc aaaatcggtg cggactggca actgcgcgga cagcaaaaac   7500
gggtggtcac gccgggacag aatgaaaaat attatctggc cggagcgctg cacagcggga   7560
caggtaaagt cagctgtgtg ggcggcaaca gcaaaagttc ggcgctgttc atcagcctgc   7620
tgaagcggct taaagcgaca taccgtcggg cgaaaaccat cacgctgatc gtggacaact   7680
acattatcca caaaagccgg gaaacacaga gctggctgaa ggagaacccg aagttcaggg   7740
tcatttatca gccggtttac tcgccatgga tgaatcatgt tgaacggcta tggcaggcac   7800
ttcacgacac aataacgcgt aatcatcagt gcagctcaat gtggcaactg ttgaaaaaag   7860
```

```
ttcgccattt tatggaaacc gtcagcccat tccccggagg caaacatggg ctggcaaaag   7920
tgtagcggta ttaagcgcag ctatttagga tgagaatatg ttgttagaat atgttgaaag   7980
aaaaatttcc ttagccttga gtaagtatcc taaggtaagg gatgttatta agttctttta   8040
tttatatatc gcatcattat tcggaattat tttgaataaa aataagacgg ttattcaatc   8100
aaaaatatac gagatttcaa ttgatgattc tgaagaatca tttttggct attatgacca    8160
tagtccaatg agctctaatg ggcggtacgt attgttccac tctagtgcgt ttagcactaa   8220
acgacatcca aagaaagtta agtatatatc tatttgcgta aaagaccttc ttaataacaa   8280
agtttataag ctatatgata cgcgagcatt taattggcag cagggaagcc gattaatgtg   8340
gattgatgat gacaatataa tttttaatga ctatgaaaat aatggataca ttagtgttgt   8400
ctattctttg tctttgatga aggttataaa aaaaataaac tatccgattt atgatgtgaa   8460
taattacaag gctgtgacgt tagatttctc atggctggct aaatatgata gcgattatgg   8520
ttattataat aaaaaatcat tttctacaga tatttcaatc attaatttga atacgggggg   8580
aatagaatta tttttatcct tagacgaaat gctaaagaga actaatttta aatgtaatat   8640
tgatgttgaa catgtggtca atcattttat gtttgctccc gatggacgtt ccgttatgtt   8700
catacatcga tactatacac ctaaaggaaa gcgtgaaagg ttaatacatt ggaatttaat   8760
aaatgataat gttcgagtcc taataaatga atcgattatt agtcattgtt gttggaatgg   8820
gaatgatgaa attataggtt tttttggtgc agaaatagat tcgctaaatt attatagatt   8880
gtcaattgaa tcctgtaata cagagaaatt gtttttttgat gcaagaaaat attctgatgg  8940
acatcctact atagttcata atagatatat tatatctgat acttacccag ataaaaatag   9000
aattaaaaag ttgtttgttt atgaccttgt caaaaatgat tatcgcgagc ttggattatt   9060
ttatgagtca atgagttttt tttcttattc tcgatgtgac ttacatccaa ggatctcggt   9120
tgataataga tttttgtttg ttgattcagt tcactcaggg aaaagaaaac tatattttat   9180
gaggagtggt atttgtgagt gatgttctag tatctttaat tatagtttgc tttaatgcag   9240
agaagtatat tgaaaaatct cttttggcat ttattaatca agatgttgga ttagataaat   9300
ttgaattgat tattgtagat ggggattcat ctgataatac aatatctatt gttcaggatg   9360
ttttttctaa acatagcaac attaagcata aaattatcaa taataaaaaa agaactcttg   9420
ctacgggttg gaatattggg gtgctagaag ctaatggtaa gtttgtgtgt agagttgatg   9480
cacatagtga tattccaaat aactatatat ctaaattatt agatgattat tttaatatta   9540
tgcagtttga tgatagcgtt gttggtgttg gaggtgtatt aactaattct tataaaacta   9600
agtttggttc aattgtagcg gatttttatg catcgaaatt tggtgttggt aattctccat   9660
ttaggtgcgt agacaaaaat aatcgactaa aaaaaacaga tacagctgtc tttgctttat   9720
ataataaaga tgtgtttttt gatgttggac tttttaatga agtattagat agaaatcaag   9780
atattgattt tcataagaga gttttaagca ataatttgtc attatataca gataatagtt   9840
tatttgttga gtattatgtt agagataatt ttaaagattt cataaagaaa ggttttcttg   9900
atggtttttg ggttgttatg tctggagcat attattttag acatatagtg ccactttttt   9960
ttgttttgta tttaattgta tctttttctc ttttctttgc tactggtgat tatatatatt  10020
tatctttttt atttttttat tttcttattt ctattttgtt ttcaattcga gatgggcgaa  10080
gttttatagg tagagtattt cttcctttta tatttttgtc ttatcatatt tcttatggat  10140
gtggatcgtt attatctttt ttgaaaaggt attttaaatg aaaaatttta ttccttttgc  10200
gttacctgaa attggcgaag aagaaattgc agaggtaatt gactctttac gttcaggttg  10260
```

```
gattacgaca ggtcctaagg ctaagcaatt tgaacaagaa ttttctaatt acctaggagc  10320
gaacgttcaa tcattagctg ttaactctgc tacgtcgggc ttacatttgg ctcttgaagc  10380
tgttggcgta aagccgggag accaagttat tgtcccatca tatacattca ctgctactgc  10440
cgaaattgtc aggtaccttg gtgctgatcc tgtaattgtt gatgtagatc gtaaaacatt  10500
taatatatca gttgatgcca ttgagaaggc tattactaat gaaacaaagg cgattattcc  10560
agtacacttc gctggattag cttgtgacat ggattcaatc ttatcaattg ctaaaaaata  10620
tgacctaaag gttgtcgagg atgccgctca tgcatttcct acaacatata aaggaagtaa  10680
gataggaacg cttgattcag atgctacggt ttttagcttc tacgccaata aaactatgac  10740
aaccggtgaa ggcggaatgg ttgtttcaaa aaataaagat ataattgagc gttgtaaggt  10800
aatgcgttta catggaatca gtcgtgacgc ttttgaccgg taccagtcta aaactccttc  10860
ttggttttat gaggttgtag ctccagggtt taaatacaat atgcctgata tctgtgcggc  10920
aatcggtatt catcaactta gaaagatcga tgattttcag aaaaaacgtc aacgaatggc  10980
aaaaatttac gatgatgcgt taaaagaatt gccacttgaa ttgcctgaat ggcctactaa  11040
tgctagtgat attcatgctt ggcatctata tcctatccgc ttaaaaactg attcggctat  11100
taatcgcgat gattttatta agaagttatc agatcttgga attggttgtt ctgtccattt  11160
tataccgttg cataagcaac cggtttggcg tgatacatat aatttgaacg ccagtgactt  11220
tccagtttct gaggagtgtt atttaaatga aatatctatt cctctttata ctaaaatgac  11280
ggatcaagat cagttgttcg ttatcaaatc gattagacaa ttatttatgt aatggtattt  11340
tatattaaat gaaacgtatt tttgatgtta tcgtggcagg cttaggcctg ctttttctat  11400
ttcctgtttt tatcattgtg tcaatgttaa ttgttgctga ttctaaaggg ggggtttttt  11460
ttaggcagta tagagttggg agatttggga aagattttag gatacataaa tttagaacga  11520
tgtttatcga ttcagaaaaa aaaggacgga taacagttgg tcaagatgct cgggtaacca  11580
gagttggatg gtatttacgg aagtacaaaa tcgatgagct tcctcaattg atagatgttc  11640
tttctggaac aatgagtttg gttggcccaa gaccggaagt gagggagttt attgatgagt  11700
atcctgatga tataagggaa aaagttttat cggttaggcc agggataact gacttagcat  11760
ctatagaaat ggtagatgaa aatgagattt tgtctagtta tgatgaccca cgtagggctt  11820
atatagatat aattcttcca atcaagcaaa gatattattt agattatgtt gctaacaatt  11880
cagtaaagta tgattgtgtg ataatttgga aaactattat taagattttg tcgcgataat  11940
aaggtagtgt aggatgattg atagaatatt ggagctgcca agaattgtta agagaggtat  12000
catcatctgc attgatgtag ttatggtgat attctcattt tggttgtctt attggttgag  12060
gcttgatgag caaacggctt ttcttagtgc accgatgtgg tttgctgcag ctattcttac  12120
catatttacc gtgtttatat ttatcaggat tgggctttat cgggcagtct tacggtatgt  12180
tagtgcaaag ataatgttgc taataccagt tggtattctg gcctcaacgt tatctcttgt  12240
cgttatatca tattcgctat ccataatgtt gccgcgcact gttgtcggaa tttatttttt  12300
ggttttactt ttactgacat caggctctag attgcttttt agaatgatac ttaactatgg  12360
agttaagggt agtgcgcctg ttttgattta tggcgctggt gaatctggcc gacaattatt  12420
gccagcatta atgcaggcaa aagaatattt tcctgtggca tttgtggatg ataatcctcg  12480
cttgcataag gctgtcattc atggtgtaac agtttatccc tcggataaac tgagttacct  12540
tgtagatcgc tatggtataa agaaaattct tttggcgatg ccgagcgtca gtaagtcaca  12600
```

```
aaggcagaaa gtgattactc gtttagagca tctaccgtgt gaagttctct ctattccggg  12660
tatggtcgat ttagtcgaag gtcgagcaca aatcagtaat ctaaaaaaag tatcgattga  12720
tgacttacta ggtcgtgatc cggttgctcc tgatgccaaa ttgatggccg aaaacattac  12780
tggcaaagcc gttatggtca ctggggcggg aggctcgatc ggctctgagc tttgtcgtca  12840
aattgttcga tataagccgg ccaaattggt tctatttgaa ctgtctgaat atgccctcta  12900
cgctattgag aaagagctct cggcgctgtg cgacaaagaa gttttgaatg ttccagtgat  12960
ccctctgttg ggctcggtgc agcgtcagaa tcgcttacag atggtgatga agtcctttgg  13020
tattcaaacg gtttatcatg cggccgctta taaacatgtg cctctggttg agcataatgt  13080
ggtggaaggg gtacgtaata acgtgtttgg taccttgtac tgcgctgagt cagcgatcga  13140
aagtggcgtt gaaacttttg tgttgatttc caccgataaa gcggtgcgcc cgaccaacac  13200
tatggggaca actaagcgtc tggccgaatt ggtattgcag gctttgtctg cacggcaaag  13260
ccaaactcgc ttttgtatgg tgcgatttgg taatgtactc ggttcttcgg gctctgtcgt  13320
gccgttgttt gaaaaacaga ttgcccaagg tgggccagtt accttgactc atcgtgacat  13380
tattcgctat ttcatgacaa ttccggaagc atcacagttg gtgattcaag cgggggcgat  13440
ggggcatggc ggcgatgtct ttgtcttaga catgggcgat ccggtcaaga tttatgactt  13500
agccaaacgc atgatccggt taagtggctt gagtgtacgg gatgataaaa atccagatgg  13560
cgatattgcc attgaagtta cggattacg tccaggggag aaactgtatg aagaattact  13620
gattggtgat tcagttcaag gtacctctca tccacgaatt atgacggcca acgaagtgat  13680
gctaccgtgg caggatctat cgctcttact taaagagctg gatcaagctt gtcatgactt  13740
tgatcatgag cgaattcgca gtttgttgtt acaagcacca gcggcattca atccaactga  13800
tgatatttgc gatctagttt ggcagcagaa aaaatcgctg ttatcacaag cgagcaatgt  13860
cattcgcctg tgattgctta ggtttaacct tccacaccaa ttcttcacct ctcttacaaa  13920
tccccgctag gcggtacatc gtgaccgcct ttagcctgat gcctgctctt taacaaacag  13980
gacatcagtg tatgtttaaa ccttttagcg ccgaattttt cggcactttc tggctggttc  14040
tgggtggctg tggtagcgcc ttgatctctg ctgctttccc acagttaggt ataggctttt  14100
tgggcgtggc gttggcgttt ggtctgacag tagtcaccat ggcttatgcg gtcgggcaca  14160
tctctggtgc gcattttaac cccgcggtga ccttgggtct gtgggccggt ggacgcttcc  14220
cagcagcgcg cgtgttacct tacattatcg ctcaggttat cggcggtatt gccgctgcgg  14280
cagtgctgta tggtatcgcc agcggtaagg ctgggtttga tgcgacaacc agcggttttg  14340
cggctaatgg ttatggcctc cattcacctg gcggctatgc gttaagcgcc tgtatgctga  14400
gcgagtttgt cctcagtgcg ttttttgtcc ggagcgacag aaaaacgcgc tcctgcgggc  14460
tttgcgccac tggcgattgg tctggtaatc accccgtaaa ttaaccagcg tcaaaagtag  14520
aattttctcg taccataaac gcaggagatt ctttatgcaa acatcaaaat ttaccgacaa  14580
gcaaatcatg gcgatcctca aatgaacccc cccgggaatc ctggagacta aacttcctga  14640
gaaagaggta aacaggatga ctaaaaatac tcgtttttcc cccgaagtcc gtcaacgggc  14700
agtccgtatg gttctggaaa gtcagggcga atatgactca caatgggcga caatttgttc  14760
cattgctcca aagattggct gtacgccgga gactctgcgt gtccgggttc gccagtatga  14820
gcgggatacc gggggcggtg atggagggct caccaccgct gaacgtcagc gtctgaaaga  14880
gctggagcgt gaaaatcgtg aactgcgccg cagtaacgat atccttcgcc aagcttccgc  14940
ttattttgcg aaggcggagt tcgaccgcct ctggaaaaaa tgatgccact gctggataag  15000
```

```
ctgcgtgagc agtacggggt cggaccgcta tgcagcgaac tgcatattgc cccgtcaacg  15060
tattagggat ttgaagccca accgtacgaa aacgtacgct aagttcattt cttgaacaac  15120
ctggctgact ctatgtattt gtacagcgtt ggcctcgata tccccatcaa cacacaaatc  15180
tgcgcaactg tatgtttttt ctcgttatag agttgaacag caagggcctg tttatcctta  15240
ctcagtgttt tcggcctgcc gcccttacgt cctctggctc gtgctgcttg aagcccgacc  15300
tgagttctct ctcttgtcag gttgcgttca tcgataggaa ttaaaacccc aaaaagatta  15360
aaaaaacacc acaaaacgga tgtttcttca acaccacttt tgctccatat gaacggaacc  15420
gacgattaaa ctggatggct ctgattgatt cagggtatga atggcggttt tttgctccgt  15480
ttccctcaaa atggacgcaa cttcccctct gcggctctca gccgcaccac cgcatccggg  15540
ccaagcagct catgcatcag gacctgctct gccagacggt agccccgctt cagccccgta  15600
aaacgcatct gactcccgca cagcacgcac ttcagcgggt caaccttcag taacctctga  15660
tacatccctc tccaggtgat ttgcatcgcc gtttttctca ctgtctccgt tatgatgtac  15720
accacttctt ccagtaaccg ccgtttcgcc ggactcaaaa aaccgtagta cctcaccata  15780
cggaacccct tatccgccac atgccaggag aacctttcca tgaactcatc tccactcatc  15840
aacaggtatt cttcccgttt tgttcggtga ctgttgtaac gcagaccgat ttcatcctga  15900
ccggcataat gctccagacg actcatcggc actggtggct ttttcaggta agagccaaag  15960
tacaccgcca catgggtggc attatccatc acccgggata cgttgacatt ccagccacgg  16020
cggtaatgcg tgtccaggaa gcgattccat tcccgtttac tgcttccttc tgctgccagc  16080
gcatccggca tcaccaggtc agggtatttc cgtgacagca accgtgttat ccggtagcgc  16140
cacatgctca tcaccttacg ggcgtaaaaa tgaagatttt tccaggtgtg gcccgacgtc  16200
acaccaccgg cagttgtcga taaatggata tgcggatgcc actgctggtc acgcccccat  16260
gtgtggatca ccgtgaatat ccccgactcc acatctgcct gatggcagat ttccagtatc  16320
acatccgctg caatgcggct catctctgtc agtaaccacc ggttgtggaa caccagggac  16380
cagtactggc agggaagtgt gaacacaata tgctgccacg ggcagtcggg gaccaggctc  16440
agcagatact gtatccactg tgcgccagcc ttcaccccgc agtgcgggca ggagcggctt  16500
ttacaccgga agcagacctt ttttgtatgg caacagtccg gtgatgaaca gcaccactgt  16560
gtataccccca tcagtgtggt cccgcacgcc atgattttgg tcaccgactc aatcaccacc  16620
ggacgtactg ccccttccgg ctgcttctcc agccagttaa gccagcggtt tccctgctga  16680
aagatatcgg caaaacgggg aagcatcaga agggcggggc gactccgtcc ggccagtgaa  16740
ccgtgccaca ctccgggcag tacataccgc cggcgctgat accggaaaga atggtcgcaa  16800
attcccgctc cgtgcagcgg gcgatttccg gatacccttc gtcatcaaca cgtacaaacc  16860
agaagaccag ctttttgttt cccgcatcca caaagaacgg aatattcagg tctgcgcagc  16920
attcaacggc atcgtcaaaa ctatcaaagc gcagaacttc tgcgtcttct tcgtcaaaaa  16980
aatcatcttc gtgaagcttc acgacatagc ggggaagttt gcttctttga gaggcgggtt  17040
tacgtttacg ggtttagct gaacgggcca tataaccacc acctgaaaga caatgacatt  17100
gcctgttttt ataacggtaa ttgcagacca tgacaagccg cagccgtcag gctgcctact  17160
cgggggttca tcgcagcagc tacagatact ggaaaaaccg tcctgaaaaa ccagacggca  17220
gacgggctgt attacgcagt caggtacttg agctacatgg catcagccac ggttcggccg  17280
gagcaagaag catcgccaca atggcaaccc ggagaggcta ccagatggga cgctggcttg  17340
```

```
ctggcaggct catgaaagag ctggggctgg tcagctgtca gcagccgact caccggtata  17400

aacgtggtgg tcatgaacat gttgctatcc ctaactacct tgaaaggcag ttcgccgtga  17460

ccgagccaaa tcaggtgtgg tgcggtgatg tgacctatat ctggacgggt aagcgctggg  17520

cgtacctcgc cgttgttctc gacctgttcg caagaaaacc agtgggctgg gccatgtcgt  17580

tctcgccgga cagcaggctc accatgaaag cgctggaaat ggcatgggaa acccgtggta  17640

agcccggcgg ggtgatgttc cacagcgatc agggcagtca ttatacgagc aggcagttcc  17700

ggcagttatt gtggcgatac cagatcagac agagtatgag ccggcgcgga aactgctggg  17760

ataacagccc aatggaacgc ttcttcagga gtctgaagaa cgaatggatg ccgatggtgg  17820

gttacgtaag cttcagagag gcagctcacg ccataacgga ctatatcgtt ggatattaca  17880

gcgcactaag accgcacgaa tataacggtg ggttaccccc aaacgaatcg gaaaatcgat  17940

actggaaaaa ctctaactcg gtggccagtt tttgttgacc acttca                 17986
```

<210> SEQ ID NO 8
<211> LENGTH: 2964
<212> TYPE: DNA
<213> ORGANISM: Shigella sonnei
<220> FEATURE:
<221> NAME/KEY: misc_feature
<223> OTHER INFORMATION: GenBank Accession No. AF455358, Shigella sonnei strain 53G Wzz (wzz) complete CDS

<400> SEQUENCE: 8

```
tgatgccatt ttatttcagg aaggaggtcc gttaaactca ggctacctca cggaatattc     60

agggtctgcg cagcattcaa cggcatcgtc aaaactatca aagcgcagaa cttctgcgtc    120

ttcttcgtca aaaaaatcat cttcgtgaag cttcacgaca tagcggggaa gtttgcttct    180

ttgagaggcg ggtttacgtt tacggggttt agctgaacgg gccatataac cacctgaaag    240

acaatgacat tgcctgtttt tataacggta attgcagacc atgacaagcc gcagccgtca    300

ggctgcctac tcgatcagcc tgctgaagcg gcttaaagcg acataccgtc gggcgaaaac    360

catcacgctg atcgtggaca actacattat ccacaaaagc cgggaaacac agagctggct    420

gaaggagaac ccgaagttca gggtcattta tcagccggtt tactcgccat gggtgaacca    480

tgttgaacgg ctatggcagg cacttcacga cacaataacg cgtaatcatc agtgcagctc    540

aatgtggcaa ctgttgaaaa aagttcgcca ttttatggaa accgtcagcc cattccccgg    600

aggcaaacat gggctggcaa aagtgtagcg gtattaagcg cagctagttt agcctcacag    660

aatttacaaa catacttgtt atcattttga aggcagattt ggtcttatac aggcattgct    720

ttataatctg cactccaaat tctgcgggct atccgccggt ttgcagcagg gaagtgtggg    780

actgtatatg tctcttcaca cggagtgttc tcgattatgt cctctaatcc cagatatcac    840

ttgttgtatc gcagttggct atatcctgtt tctgcgcagc gctttgggag ctgaaactca    900

agggcggtag cgtacttttt tgtcaggctt attcttcatt tttattttta acccattgat    960

aaataatgga ttggtttcat gtcaaaagca tctgaaccac aacagacccc ttatctgatc   1020

ccgcaagggg tctatccaac ttatatgcca aaagcagagg atgaaatcga tcttttcgag   1080

cttttaggca ccttgtggaa gaaaaaatgg gttattttat gtgtcacgtt gctgactacg   1140

gggttagcag cagtgtatgc ctttaccgca aaagagcagt ggacggctaa aacctatatt   1200

caagcaccac gtattgctga attaggcagc tatcttaaat ttcaccaagc gtatgcccga   1260

atattaaatc aaccgttaga tacgaatgcg ttggctaatg gattgttttc cgatttgatt   1320

ttgattgctg aatcgccaga caccaaagtt aaatttctag agagtactga gtattataaa   1380
```

```
aaggaaacaa ataatttatc tactgaacaa gataagaaaa tttggttagc tgagcaagcg   1440

aataaaggtc ttgtgattac gccaccaaag gaaaagggaa atacaagtta ctacataata   1500

caagcatcgg cagactcagc gcaagaggca tataaactac tgcagggata tctaaagaat   1560

gttaataatc aagctgtaac attaagtctt gatgagtttg gtcaaaatgt taatactctt   1620

ttggttaatc taaataaaga aatcattgac atagatttcc agagaaaatc agaaaagctt   1680

gatcaaatag ctcatattca gcgagattta acaactgcgg aacaagccgg aatcattgat   1740

tatcgctcta gcaaaggcgg cttcgataat gcgcaaagta gctataagtt cttgctcggc   1800

gaaaaactgt tatcagcaga gctaaaagca actaaagatg cgccaattat ttacccattt   1860

agatattacg aagtgaaacg tcaaattgat gagttagaag gaatgttacg cgataacatt   1920

caggcgcaag catatcgata tcaaatgaag ccatctgagc cagttataaa agacaaaccc   1980

aacaaagcat taattttgat tcttggtgca ttaccagggg caatgtttgc tatagttggt   2040

acattagttt atgcgacatt aaaagataaa accaagttag attaaactgg gttacgtatt   2100

gttgtgtcaa tgcgaaatag atgttctatg tgcactttat gatggataag aaaatgaaat   2160

tcgatacttt gaatgcgaaa attgggatta taggccttgg ttatgttgga ttgcctcttg   2220

ctgttgagtt tggaaagaaa gtaacgacga ttggatttga tattaataag tctcgtattg   2280

atgaattacg aaatggtcac gatagtacat tagagtgctc aaatttagag ttgttagaag   2340

caactaaatt gacgtacgcc tgttcattag atgcactaaa agagtgtaat gtatttattg   2400

taactgttcc agctccaatt gataaacata aacagccaga tctaacacct ctaattaaag   2460

catctgaaac attgggtaag ataataaaga aaggcgatgt tattatttat gagtcaacag   2520

tttaccctgg agcgacagaa gaagattgta taccagttgt agagaaagta tcaggtctta   2580

agtttaatat tgattttttt gccggttatt cacctgagcg tattaatcct ggggataaag   2640

agcatcgtgt aactaatatc cttaaggtgg ccagtggatc tacaccggat gttgctgagt   2700

atgtagatca gctatataaa ttaataatta ctgtcggtac gcataaagca tcatcgataa   2760

aagtagagag gctgcaaagt aatgtaaaca cgcagcgaga tgtcaatatt gcattgatta   2820

atgagttatc tattatattt aataagttag ggattgatac cttagaggtt cttgaggctg   2880

caggtacgaa gtggaatctt ttacctttta ggcccggttt agtaggtggc cactgtatag   2940

gtgtagatcc ttattatctt acac                                          2964
```

<210> SEQ ID NO 9
<211> LENGTH: 2069
<212> TYPE: DNA
<213> ORGANISM: Shigella sonnei
<220> FEATURE:
<221> NAME/KEY: misc_feature
<223> OTHER INFORMATION: 2.1 kb HindIII fragment from AF294823 (SEQ ID NO:7 positions 14931-16999), obtained from Shigella sonnei O antigen gene cluster

<400> SEQUENCE: 9

```
aagcttccgc ttattttgcg aaggcggagt tcgaccgcct ctggaaaaaa tgatgccact     60

gctggataag ctgcgtgagc agtacggggt cggaccgcta tgcagcgaac tgcatattgc    120

cccgtcaacg tattagggat ttgaagccca accgtacgaa aacgtacgct aagttcattt    180

cttgaacaac ctggctgact ctatgtattt gtacagcgtt ggcctcgata tccccatcaa    240

cacacaaatc tgcgcaactg tatgtttttt ctcgttatag agttgaacag caagggcctg    300

tttatcctta ctcagtgttt tcggcctgcc gcccttacgt cctctggctc gtgctgcttg    360
```

```
aagcccgacc tgagttctct ctcttgtcag gttgcgttca tcgataggaa ttaaaacccc    420

aaaaagatta aaaaaacacc acaaaacgga tgtttcttca acaccacttt tgctccatat    480

gaacggaacc gacgattaaa ctggatggct ctgattgatt cagggtatga atggcggttt    540

tttgctccgt ttccctcaaa atggacgcaa cttcccctct gcggctctca gccgcaccac    600

cgcatccggg ccaagcagct catgcatcag gacctgctct gccagacggt agccccgctt    660

cagccccgta aaacgcatct gactcccgca cagcacgcac ttcagcgggt caaccttcag    720

taacctctga tacatccctc tccaggtgat ttgcatcgcc gtttttctca ctgtctccgt    780

tatgatgtac accacttctt ccagtaaccg ccgtttcgcc ggactcaaaa aaccgtagta    840

cctcaccata cggaacccct tatccgccac atgccaggag aacctttcca tgaactcatc    900

tccactcatc aacaggtatt cttcccgttt tgttcggtga ctgttgtaac gcagaccgat    960

ttcatcctga ccggcataat gctccagacg actcatcggc actggtggct ttttcaggta   1020

agagccaaag tacaccgcca catgggtggc attatccatc acccgggata cgttgacatt   1080

ccagccacgg cggtaatgcg tgtccaggaa gcgattccat tcccgtttac tgcttccttc   1140

tgctgccagc gcatccggca tcaccaggtc agggtatttc cgtgacagca accgtgttat   1200

ccggtagcgc cacatgctca tcaccttacg ggcgtaaaaa tgaagatttt tccaggtgtg   1260

gcccgacgtc acaccaccgg cagttgtcga taaatggata tgcggatgcc actgctggtc   1320

acgcccccat gtgtggatca ccgtgaatat ccccgactcc acatctgcct gatggcagat   1380

ttccagtatc acatccgctg caatgcggct catctctgtc agtaaccacc ggttgtggaa   1440

caccagggac cagtactggc agggaagtgt gaacacaata tgctgccacg ggcagtcggg   1500

gaccaggctc agcagatact gtatccactg tgcgccagcc ttcaccccgc agtgcgggca   1560

ggagcggctt ttacaccgga agcagacctt ttttgtatgg caacagtccg gtgatgaaca   1620

gcaccactgt gtatacccca tcagtgtggt cccgcacgcc atgattttgg tcaccgactc   1680

aatcaccacc ggacgtactg cccccttccgg ctgcttctcc agccagttaa gccagcggtt   1740

tccctgctga aagatatcgg caaaacgggg aagcatcaga agggcggggc gactccgtcc   1800

ggccagtgaa ccgtgccaca ctccgggcag tacataccgc cggcgctgat accggaaaga   1860

atggtcgcaa attcccgctc cgtgcagcgg gcgatttccg gatacccttc gtcatcaaca   1920

cgtacaaacc agaagaccag ctttttgttt ccccgcatcca caaagaacgg aatattcagg   1980

tctgcgcagc attcaacggc atcgtcaaaa ctatcaaagc gcagaacttc tgcgtcttct   2040

tcgtcaaaaa aatcatcttc gtgaagctt                                     2069
```

<210> SEQ ID NO 10
<211> LENGTH: 1212
<212> TYPE: DNA
<213> ORGANISM: Shigella sonnei
<220> FEATURE:
<221> NAME/KEY: misc_feature
<223> OTHER INFORMATION: 1.2 kb HindIII fragment from AF294823 (SEQ ID NO:7 positions 13725-14936) obtained from Shigella sonnei O antigen gene cluster

<400> SEQUENCE: 10

```
aagcttgtca tgactttgat catgagcgaa ttcgcagttt gttgttacaa gcaccagcgg     60

cattcaatcc aactgatgat atttgcgatc tagtttggca gcagaaaaaa tcgctgttat    120

cacaagcgag caatgtcatt cgcctgtgat tgcttaggtt taaccttcca caccaattct    180

tcacctctct tacaaatccc cgctaggcgg tacatcgtga ccgcctttag cctgatgcct    240
```

```
gctctttaac aaacaggaca tcagtgtatg tttaaacctt ttagcgccga atttttcggc    300

actttctggc tggttctggg tggctgtggt agcgccttga tctctgctgc tttcccacag    360

ttaggtatag gctttttggg cgtggcgttg gcgtttggtc tgacagtagt caccatggct    420

tatgcggtcg ggcacatctc tggtgcgcat tttaaccccg cggtgacctt gggtctgtgg    480

gccggtggac gcttcccagc agcgcgcgtg ttaccttaca ttatcgctca ggttatcggc    540

ggtattgccg ctgcggcagt gctgtatggt atcgccagcg gtaaggctgg gtttgatgcg    600

acaaccagcg gttttgcggc taatggttat ggcctccatt cacctggcgg ctatgcgtta    660

agcgcctgta tgctgagcga gtttgtcctc agtgcgtttt ttgtccggag cgacagaaaa    720

acgcgctcct gcgggctttg cgccactggc gattggtctg gtaatcaccc cgtaaattaa    780

ccagcgtcaa aagtagaatt ttctcgtacc ataaacgcag gagattcttt atgcaaacat    840

caaaatttac cgacaagcaa atcatggcga tcctcaaatg aaccccccg ggaatcctgg    900

agactaaact tcctgagaaa gaggtaaaca ggatgactaa aaatactcgt tttccccccg    960

aagtccgtca acgggcagtc cgtatggttc tggaaagtca gggcgaatat gactcacaat   1020

gggcgacaat ttgttccatt gctccaaaga ttggctgtac gccggagact ctgcgtgtcc   1080

gggttcgcca gtatgagcgg gataccgggg gcggtgatgg agggctcacc accgctgaac   1140

gtcagcgtct gaaagagctg gagcgtgaaa atcgtgaact gcgccgcagt aacgatatcc   1200

ttcgccaagc tt                                                       1212
```

<210> SEQ ID NO 11
<211> LENGTH: 1405
<212> TYPE: DNA
<213> ORGANISM: Shigella sonnei
<220> FEATURE:
<221> NAME/KEY: misc_feature
<223> OTHER INFORMATION: 1.4 kb XbaI-HindIII fragment from AF294823 (SEQ ID NO:7 positions 12326-13730) obtained from Shigella sonnei O antigen gene cluster

<400> SEQUENCE: 11

```
tctagattgc tttttagaat gatacttaac tatggagtta agggtagtgc gcctgttttg     60

atttatggcg ctggtgaatc tggccgacaa ttattgccag cattaatgca ggcaaaagaa    120

tattttcctg tggcatttgt ggatgataat cctcgcttgc ataaggctgt cattcatggt    180

gtaacagttt atccctcgga taaactgagt taccttgtag atcgctatgg tataaagaaa    240

attcttttgg cgatgccgag cgtcagtaag tcacaaaggc agaaagtgat tactcgttta    300

gagcatctac cgtgtgaagt tctctctatt ccgggtatgg tcgatttagt cgaaggtcga    360

gcacaaatca gtaatctaaa aaaagtatcg attgatgact tactaggtcg tgatccggtt    420

gctcctgatg ccaaattgat ggccgaaaac attactggca aagccgttat ggtcactggg    480

gcgggaggct cgatcggctc tgagctttgt cgtcaaattg ttcgatataa gccggccaaa    540

ttggttctat ttgaactgtc tgaatatgcc ctctacgcta ttgagaaaga gctctcggcg    600

ctgtgcgaca aagaagtttt gaatgttcca gtgatccctc tgttgggctc ggtgcagcgt    660

cagaatcgct tacagatggt gatgaagtcc tttggtattc aaacggttta tcatgcggcc    720

gcttataaac atgtgcctct ggttgagcat aatgtggtgg aaggggtacg taataacgtg    780

tttggtacct tgtactgcgc tgagtcagcg atcgaaagtg gcgttgaaac ttttgtgttg    840

atttccaccg ataaagcggt gcgcccgacc aacactatgg ggacaactaa gcgtctggcc    900

gaattggtat tgcaggcttt gtctgcacgg caaagccaaa ctcgcttttg tatggtgcga    960
```

```
tttggtaatg tactcggttc ttcgggctct gtcgtgccgt tgtttgaaaa acagattgcc   1020

caaggtgggc cagttacctt gactcatcgt gacattattc gctatttcat gacaattccg   1080

gaagcatcac agttggtgat tcaagcgggg gcgatggggc atggcggcga tgtctttgtc   1140

ttagacatgg gcgatccggt caagatttat gacttagcca aacgcatgat ccggttaagt   1200

ggcttgagtg tacgggatga taaaaatcca gatggcgata ttgccattga agttacggga   1260

ttacgtccag gggagaaact gtatgaagaa ttactgattg gtgattcagt tcaaggtacc   1320

tctcatccac gaattatgac ggccaacgaa gtgatgctac cgtggcagga tctatcgctc   1380

ttacttaaag agctggatca agctt                                          1405


<210> SEQ ID NO 12
<211> LENGTH: 27
<212> TYPE: DNA
<213> ORGANISM: Shigella sonnei
<220> FEATURE:
<221> NAME/KEY: misc_feature
<223> OTHER INFORMATION: promoter consensus sequence of AF294823 (SEQ ID
      NO:7 positions 1645-1671), promoter and operator sequence
      immediately upstream (5') of wbgT gene

<400> SEQUENCE: 12

attaccaggg gcaatgtttg ctatagt                                          27


<210> SEQ ID NO 13
<211> LENGTH: 20
<212> TYPE: DNA
<213> ORGANISM: Shigella sonnei
<220> FEATURE:
<221> NAME/KEY: misc_feature
<223> OTHER INFORMATION: transcription terminator sequence of AF294823
      (SEQ ID NO:7 positions 13930-13949), immediately downstream (3')
      of wbgZ gene

<400> SEQUENCE: 13

ggcggtacat cgtgaccgcc                                                  20


<210> SEQ ID NO 14
<211> LENGTH: 38
<212> TYPE: DNA
<213> ORGANISM: Shigella sonnei
<220> FEATURE:
<221> NAME/KEY: misc_feature
<223> OTHER INFORMATION: JUMPstart sequence of AF294823 (SEQ ID NO:7
      positions 877-914)

<400> SEQUENCE: 14

cagcgctttg ggagctgaaa ctcaagggcg gtagcgta                              38


<210> SEQ ID NO 15
<211> LENGTH: 1032
<212> TYPE: DNA
<213> ORGANISM: Shigella sonnei
<220> FEATURE:
<221> NAME/KEY: misc_feature
<223> OTHER INFORMATION: transposable element IS630 sequence of AF294823
      (SEQ ID NO:7 positions 6894-7925)

<400> SEQUENCE: 15

atgccgatca tagcaccaat ttcccgtgac gaacgacgcc tgatgcagaa agccatccat     60

aaaacacacg ataaaaatta tgcccgcaga ctgactgcca tgctgatgct gcaccggggc    120

gaccgtgtca gcgacgttgc cagaacgctc tgctgcgccc gttcctctgt tggacgctgg    180
```

```
attaactggt tcacgcagtc gggtgttgag ggactgaaat cattacctgc cgggcgtgcc    240

cgtcgctggc cgtttgagca tatctgcaca ctgttacgtg agctggtaaa acattctccc    300

ggcgactttg gctaccagcg ttcacgctgg agtacagaac tgctggcaat aaaaatcaat    360

gagataaccg gttgccagtt aaatgccgga accgttcgcc gctggttgcc gtctgcgggg    420

attgtgtggc gaagggctgc gccaactctg cgtatccgtg acccgcataa agatgaaaag    480

atggcagcaa tccataaagc actggacgaa tgcagcgcag agcatccggt cttttatgaa    540

gatgaagtgg atatccatct taatcccaaa atcggtgcgg actggcaact gcgcggacag    600

caaaaacggg tggtcacgcc gggacagaat gaaaaatatt atctggccgg agcgctgcac    660

agcgggacag gtaaagtcag ctgtgtgggc ggcaacagca aaagttcggc gctgttcatc    720

agcctgctga agcggcttaa agcgacatac cgtcgggcga aaaccatcac gctgatcgtg    780

gacaactaca ttatccacaa aagccgggaa acacagagct ggctgaagga gaacccgaag    840

ttcagggtca tttatcagcc ggtttactcg ccatggatga atcatgttga acggctatgg    900

caggcacttc acgacacaat aacgcgtaat catcagtgca gctcaatgtg gcaactgttg    960

aaaaaagttc gccattttat ggaaaccgtc agcccattcc ccggaggcaa acatgggctg   1020

gcaaaagtgt ag                                                       1032
```

<210> SEQ ID NO 16
<211> LENGTH: 13660
<212> TYPE: DNA
<213> ORGANISM: Shigella sonnei
<220> FEATURE:
<221> NAME/KEY: misc_feature
<223> OTHER INFORMATION: GenBank Accession No. AF285971, Shigella sonnei related sequences, Shigella sonnei plasmid Pinv O antigen gene cluster, complete sequence

<400> SEQUENCE: 16

```
atttttaacc cattgataaa taatggattg gtttcatgtc aaaagcatct gaaccacaac     60

agacccctta tctgatcccg caaggggtct atccaactta tatgccaaaa gcagaggatg    120

aaatcgatct tttcgagctt ttaggcacct tgtggaagaa aaaatgggtt attttatgtg    180

tcacgttgct gactacgggg ttagcagcag tgtatgcctt taccgcaaaa gagcagtgga    240

cggctaaaac ctatattcaa gcaccacgta ttgctgaatt aggcagctat cttaaatttc    300

accaagcgta tgcccgaata ttaaatcaac cgttagatac gaatgcgttg gctaatggat    360

tgttttccga tttgattttg attgctgaat cgccagacac caaagttaaa tttctagaga    420

gtactgagta ttataaaaag gaaacaaata atttatctac tgaacaagat aagaaaattt    480

ggttagctga gcaagcgaat aaaggtcttg tgattacgcc accaaaggaa aagggaaata    540

caagttacta cataatacaa gcatcggcag actcagcgca agaggcatat aaactactgc    600

agggatatct aaagaatgtt aataatcaag ctgtaacatt aagtcttgat gagtttggtc    660

aaaatgttaa tactcttttg gttaatctaa ataaagaaat tattgacata gatttccaga    720

gaaaatcaga aaagcttgat caaatagctc atattcagcg agatttaaca actgcggaac    780

aagccggaat cattgattat cgctctagca aaggcggctt cgataatgcg caaagtagct    840

ataagttctt gctcggcgaa aaactgttat cagcagagct aaaagcaact aaagatgcgc    900

caattattta cccatttaga tattacgaag tgaaacgtca aattgatgag ttagaaggaa    960

tgttacgcga taacattcag gcgcaagcat atcgatatca aatgaagcca tctgagccag   1020

ttataaaaga caaacccaac aaagcattaa ttttgattct tggtgcatta ccaggggcaa   1080
```

```
tgtttgctat agttggtaca ttagtttatg cgacattaaa agataaaacc aagttagatt   1140
aaactgggtt acgtattgtt gtgtcaatgc gaaatagatg ttctatgtgc actttatgat   1200
ggataagaaa atgaaattcg atactttgaa tgcgaaaatt gggattatag gccttggtta   1260
tgttggattg cctcttgctg ttgagtttgg aaagaaagta acgacgattg gatttgatat   1320
taataagtct cgtattgatg aattacgaaa tggtcacgat agtacattag agtgctcaaa   1380
tttagagttg ttagaagcaa ctaaattgac gtacgcctgt tcattagatg cactaaaaga   1440
gtgtaatgta tttattgtaa ctgttccaac tccaattgat aaacataaac agccagatct   1500
aacacctcta attaaagcat ctgaaacatt gggtaagata ataaagaaag gcgatgttat   1560
tatttatgag tcaacagttt accctggagc gacagaagaa gattgtatac cagttgtaga   1620
gaaagtatca ggtcttaagt ttaatattga tttttttgcc ggttattcac ctgagcgtat   1680
taatcctggg gataaagagc atcgtgtaac taatatcctt aaggtgacca gtggatctac   1740
accggatgtt gctgagtatg tagatcagct atataaatta ataattactg tcggtacgca   1800
taaagcatca tcgataaaag tagcagaggc tgcaaaagta attgaaaaca cgcagcgaga   1860
tgtcaatatt gcattgatta atgagttatc tattatattt aataagttag ggattgatac   1920
cttagaggtt cttgaggctg caggtacgaa gtggaatttt ttacctttta ggcccggttt   1980
agtaggtggc cactgtatag gtgtagatcc ttattatctt acacataaag cgcaaagtgt   2040
cggctatcat ccggagatga ttttagccgg acgtcgttta aatgatagta tggggcagta   2100
tgtcgtttcc cagttagtca aaaaaatgtt gaaacaacgg attcaagttg aaggggcgaa   2160
tgtgttagtg atggggctta catttaaaga gaattgccca gatctacgaa acactaaagt   2220
gattgatatt atttcagagt taaaagaata caatatcaat atagatatta tagatccatg   2280
gtgttctacc gatgaggcac aacatgaata tggattaact ttatgtgaag atcctaaagt   2340
taatcattat gatgcaataa ttatcgctgt tgcacacaat gagtttcgcg agatgggaga   2400
gagcgctatt cgtgcattag gtaaagacga gcacgttttg ttcgatttaa aatatgtgct   2460
tgataaaaaa agtatcgata tgcgcttgta agagtgatta aaaaaatcaa atcctctttg   2520
atatgataca cctcagcatt ttatgctagg tttagcactt gattaatata catggatatt   2580
tatatgtctc gctatgaaga gattacacag cagttaattt tttcaccgaa aacttggtta   2640
attactggtg tcgctggctt tataggatca aatcttttag aaaagttact taaattaaac   2700
caggttgtta ttgggttaga taacttttcc acgggacatc aatataatct tgatgaagtt   2760
aaaacattag tttccactga acagtggagt cgattttgct ttatagaagg tgatattcga   2820
gatctcacta cctgtgagca agttatgaaa ggtgttgatc atgtcttaca tcaggctgcg   2880
ctaggttctg tacctcgttc aattgttgat cctataacaa ccaatgcaac taatattact   2940
ggatttttga atatcttaca tgcggctaaa aatgcacaag tacaaagttt tacttatgct   3000
gcatcaagct caacttatgg agatcatccc gcactaccaa aagtagagga aaacattggt   3060
aatccacttt ctccttatgc agttactaaa tatgttaacg agatttatgc tcaggtatat   3120
gctcgaacat atggttttaa aactattgga ttacgttatt ttaatgtatt tggtcgtcgt   3180
caagatccta atggagctta tgctgcagta attccaaaat ggacagcagc aatgcttaaa   3240
ggtgatgacg tatatattaa tggcgatggt gaaacgagtc gtgatttttg ttatatagat   3300
aatgttatac aaatgaatat attatctgca ttagcgaagg acagtgctaa agataatata   3360
tataatgttg cagttggtga tagaacaacg ttaaatgaat tatctggtta catttatgat   3420
gagcttaatt taattcacca tatcgataaa ttgagcatta agtatagaga gtttagatct   3480
```

```
ggagatgtta ggcattctca ggctgatgtt actaaggcta tagatttact aaagtataga   3540
ccaaatataa aaatcagaga gggattacga ctttcaatgc cgtggtatgt gagattttta   3600
aaaggctaaa ttatattaac atgaataaat aatctatttc acctctgtta ttaatgcagg   3660
ggtgaaaatc catgtattta ttctaaatgg tcagtgtatg tttagaaaaa tgattgatgc   3720
aggtggtaca tttttactta aagcaatatt tcaaatagga gtttttgttt atttcacaca   3780
tgtgtcagat attactacat ttggtattat tagttatgtg tttactgttt attggtttgt   3840
gcttaacttc tctgattatg gatttagaac aaaattagtg aaagatattt ctgataatag   3900
ttattctgca tcagaattat tatcaagaag tgatggagtt aaaacatatg ctttttttctt   3960
catttttata atcttcatgt tttattctta tgtttctgat tcaatttcat taactctgct   4020
tgtttatatt tcatctgcat attttgtttg tatttcaagt ggtagattta gcttgctaca   4080
ggctgttggt cggtttagat gtgaattata tataaatatc tactcaacaa ttatatatat   4140
tgggtgtaat ttatttttat ctctgtttat cgaacctcta tattatagtg cgatatcaat   4200
attcatatac tcaatttcgc ttttggtttt ctcatcacat aaatgcaatg tgccatgttt   4260
tcatataaaa agaccaagta ttttagttta taaagatttt ttggatgcaa ctccgttcgc   4320
tattctggtg ttactaaatg ttgttttatc tagtattgac ctttttatat taaaagaata   4380
tttctcttat aatagtgttg ctatatatca ggtggtaact agggttaata ccggtctaat   4440
aatagtgttt aatgttattt atactgtttt attgccttca ttttcttatt atctgaaaaa   4500
ttctgaatgg ggtaatataa ggaaattaca acgatatata tcactgttag tcttattact   4560
atgtttatgc tattattttt ttggcatcta tttcgtaggg atattgtttg gtgatgagta   4620
taaggtaata tcttctgcaa catttttgat aatgtttatg gctcttatta aatataattt   4680
ttggctaata aatgaacttt atcttgtgtg tagtggaaat caaagcgagc gagttaaatc   4740
gtattgtatt ggtgtggtca tttcaatggc ggttttcttt tattttatac ctcggtatgg   4800
atggagtggg gcggtttttg gaagtgccat tgcaacatta gtaattggaa tattttatat   4860
tatttctgtg aaaaaagatt gtgggaaaat tcttcatgat aagtattcac taatgatgat   4920
ctttgtccca atttctttt attttattat taatggtcag cagcggttgt tatattaata   4980
tgttgtggtt ttatatcgtt ccattaatat gtttagactc gattgaaagc ctaataaagg   5040
ttaagtatgt taatatacct atatcctgta cttttgttat ttaatatcct tccggttttt   5100
ttttatggac aaatgaactc tgatttagag cgttttttttg gagttcctat tggctatatt   5160
ccagatctaa tattttattt ctttgttgtt ttaacatcta taataacgtt gaggtttcac   5220
gtttctctgt ggacaaagaa attattattt ttaggcatca tattcctgat ttatatcagc   5280
attcagatgt tgttgttatc agcggatata tcaggtgtcg taattttatt atcgtttttt   5340
tctaatttta tagctttggt tcttttggtg tcattttgca ttggtaaaga tgagctttat   5400
ttaactcatt cggttagaaa tataaatgtt gtaatgtgtt ttggtattat ctgtggagtt   5460
gtaaaattat ttattggtta ttctgaagat agtaatttta tagtttattt aaatagaaat   5520
gccaccgcaa ttatagtagt gtgcttttat tgtgtatatt catactttta tcgtggtcga   5580
aagtcttggt atgtctcatc tgtattgtac tctctgttct ttctttttct ggatagccga   5640
gcaggaataa tatcatttgc tatatcgttg ttttttgttt ttcttcagtt aacaaagaag   5700
gaaaagttat taatatcatt gttttttgtt cctcttctaa ctttaggtat ttcttttact   5760
gatataggca ctcgtcttga acgaatgctg tcttcgtcac aggttatatt ctctggtggt   5820
```

-continued

```
aacactctta caaaaagtca gaatgattat cgtcgagttg agttagtatt tattggggtt   5880
gatgttttaa aagaaaatta tttaattggc actggattag gtgttgcaaa ttatgtaaag   5940
gctatagata aaaagttttt aggaagtacc aactttgggt tggcgcataa tttttattta   6000
tcttattcgg ctcagttagg gattattggt tttattttgc ttatttctgt attttatata   6060
atgctgtctc caatttttaa atgcggaggg tatattggta aaggatgcgt tttgctttg    6120
gctttctatg tctttttaa tgagtatata ttgacgccag cgatatatat ttatatttct   6180
atttttttat cggtggtttt tatacgtaat tctaaatagc tgcgcggaat agtagatcac   6240
tttgagggaa cttagcccgg attgtgcgat ctgatcaatc gccaaatcaa aacaaatcac   6300
caaccggact gagcaatgcc gatcatagca ccaatttccc gtgacgaacg acgcctgatg   6360
cagaaagcca tccataaaac acacgataaa aattatgccc gcagactgac tgccatgctg   6420
atgctgcacc ggggcgaccg tgtcagcgac gttgccagaa cgctctgctg cgcccgttcc   6480
tctgttggac gctggattaa ctggttcacg cagtcgggtg ttgagggact gaaatcatta   6540
cctgccgggc gtgcccgtcg ctggccgttt gagcatatct gcacactgtt acgtgagctg   6600
gtaaaacatt ctcccggcga ctttggctac ggttcacgct ggagtacaga actgctggca   6660
ataaaaatca atgagataac cggttgccag ttaaatgccg gaaccgttcg ccgctggttg   6720
ccgtctgcgg ggattgtgtg gcgaagggct gcgccaactc tgcgtatccg tgacccgcat   6780
aaagatgaaa agatggcagc aatccataaa gcactggacg aatgcagcgc agagcatccg   6840
gtcttttatg aagatgaagt ggatatccat cttaatccca aaatcggtgc ggactggcaa   6900
ctgcgcggac agcaaaaacg ggtggtcacg ccgggacaga atgaaaaata ttatctggcc   6960
ggagcgctgc acagcgggac aggtaaagtc agctgtgtgg gcggcaacag caaaagttcg   7020
gcgctgttca tcagcctgct gaagcggctt aaagcgacat accgtcgggc gaaaaccatc   7080
acgctgatcg tggacaacta cattatccac aaaagccggg aaacacagag ctggctgaag   7140
gagaacccga cgttcagggg tcatttatca gcggtttact cgccatggat gaatcatgtt   7200
gaacggctat ggcaggcact tcacgacaca ataacgcgta atcatcagtg cagctcaatg   7260
tggcaactgt tgaaaaaagt tcgccatttt atggaaaccg tcagcccatt ccccggaggc   7320
aaacatgggc tggcaaaagt gtagcggtat taagcgcagc tatttaggat gagaatatgt   7380
tgttagaata tgttgaaaga aaaatttcct tagccttgag taagtatcct aaggtaaggg   7440
atgttattaa gttcttttat ttatatatcg catcattatt cgcaattatt ttgaataaaa   7500
ataagacggt tattcaatca aaaatatacg agatttcaat tgatgattct gaagaatcat   7560
tttttggcta ttatgaccat agtccaatga gctctaatgg gcggtacgta ttgttccact   7620
ctagtgcgtt tagcactaaa cgacatccaa agaaagttaa gtatatatct atttgcgtaa   7680
aagaccttct taataacaaa gtttataagc tatatgatac gcgagcattt aattggcagc   7740
agggaagccg attaatgtgg attgatgatg acaatataat ttttaatgac tatgaaaata   7800
atggatacat tagtgttgtc tattctttgt ctttgatgaa ggttataaaa aaaataaact   7860
atccgattta tgatgtgaat aattacaagg ctgtgacgtt agatttctca tggctggcta   7920
aatatgatag cgattatggt tattataata aaaaatcatt ttctacagat atttcaatca   7980
ttaatttgaa cacgggggga atagaattat ttttatcctt agacgaaatg ctaaagagaa   8040
ctaattttaa atgtaatatt gatgttgaac atgtggtcaa tcattttatg tttgctcccg   8100
atggacgttc cgttatgttc atacatcgat actatacacc taaaggaaag cgtgaaaggt   8160
taatacattg gaatttaata aatgataatg ttcgagtcct aataaatgaa tcgattatta   8220
```

```
gtcattgttg ttggaatggg aatgatgaaa ttataggttt ttttggtgca gaaatagatt   8280
cgctaaatta ttatagattg tcaattgaat cctgtaatac agagaaattg ttttttgatg   8340
caagaaaata ttctgatgga catcctacta tagttcataa tagatatatt atatctgata   8400
cttacccaga taaaaataga attaaaaagt tgtttgttta tgaccttgtc aaaaatgatt   8460
atcgcgagct tggattattt tatgagtcat tgagtttttt ttcttattct cgatgtgact   8520
tacatccaag gatctcggtt gataatagat ttttgtttgt tgattcagtt cactcaggga   8580
aaagaaaact atattttatg aggagtggta tttgtgagtg atgttctagt atctttaatt   8640
atagtttgct ttaatgcaga gaagtatatt gaaaaatctc ttttggcatt tattaatcaa   8700
gatgttggat tagataaatt tgaattgatt attgtagatg gggattcatc tgataataca   8760
atatctattg ttcaggatgt tttttctaaa catagcaaca ttaagcataa aattatcaat   8820
aataaaaaaa gaactcttgc tacgggttgg aatattgggg tgctagaagc taatggtaag   8880
tttgtgtgta gagttgatgc acatagtgat attccaaata actatatatc taaattatta   8940
gatgattatt ttaatattat gcagtttgat gatagcgttg ttggtgttgg aggtgtatta   9000
actaattctt ataaaactaa gtttggttca attgtagcgg atttttatgc atcgaaattt   9060
ggtgttggta attctccatt taggtgcgta gacaaaaata atcgactaaa aaaaacagat   9120
acggctgtct ttgctttata taataaagat gtgttttttg atgttggact ttttaatgaa   9180
gtattagata gaaatcaaga tattgatttt cataagagag ttttaagcaa taatttgtca   9240
ttatatacag ataatagttt atttgttgag tattatgtta gagataattt taaagatttc   9300
ataaagaaag gttttcttga tggtttttgg gttgttatgt ctggagcata ttattttaga   9360
catatagtgc cacttttttt tgttttgtat ttaattgtat ctttttctct tttctttgct   9420
actggtgatt atatatattt atcttttttta tttttttatt ttcttatttc tattttgttt   9480
tcaattcgag atgggcgaag ttttataggt agagtatttc ttccttttat atttttgtct   9540
tatcatattt cttatggatg tggatcgtta ttatcttttt tgaaaaggta ttttaaatga   9600
aaaattttat tccttttgcg ttacctgaaa ttggcgaaga agaaattgca gaggtaattg   9660
actctttacg ttcaggttgg attacgacag gtcctaaggc taagcaattt gaacaagaat   9720
tttctaatta cctaggagcg aacgttcaat cattagctgt taactctgct acgtcgggct   9780
tacatttggc tcttgaagct gttggcgtaa agccgggaga ccaagttatt gtcccatcat   9840
atacattcac tgctactgcc gaaattgtca ggtaccttgg tgctgatcct gtaattgttg   9900
atgtagatcg taaaacattt aatatatcag ttgatgccat tgagaaggct attactaatg   9960
aaacaaaggc gattattcca gtacacttcg ctggattagc ttgtgacatg gattcaatct  10020
tatcaattgc taaaaaatat gacctaaagg ttgtcgagga tgccgctcat gcatttccta  10080
caacatataa aggaagtaag ataggaacgc ttgattcaga tgctacggtt tttagcttct  10140
acgccaataa aactatgaca accggtgaag gcggaatggt tgtttcaaaa aataaagata  10200
taattgagcg ttgtaaggta atgcgtttac atggaatcag tcgtgacgct tttgaccggt  10260
accagtctaa aactccttct tggttttatg aggttgtagc tccagggttt aaatacaata  10320
tgcctgatat ctgtgcggca atcggtattc atcaacttag aaagatcgat gattttcaga  10380
aaaaacgtca acgaatggca aaaatttacg atgatgcgtt aaaagaattg ccacttgaat  10440
tgcctgaatg gcctactaat gctagtgata ttcatgcttg gcatctatat cctatccgct  10500
taaaaactga ttcggctatt aatcgcgatg attttattaa gaagttatca gatcttggaa  10560
```

```
ttggttgttc tgtccatttt ataccgttgc ataagcaacc ggtttggcgt gatacatata  10620
atttgaacgc cagtgacttt ccagtttctg aggagtgtta tttaaatgaa atatctattc  10680
ctctttatac taaaatgacg gatcaagatc agttgttcgt tatcaaatcg attagacaat  10740
tatttatgta atggtatttt atattaaatg aaacgtattt ttgatgttat cgtggcaggc  10800
ttaggcctgc tttttctatt tcctgttttt atcattgtgt caatgttaat tgttgctgat  10860
tctaaagggg gggttttttt taggcagtat agagttggga gatttgggaa agattttagg  10920
atacataaat ttagaacgat gtttatcgat tcagaaaaaa aaggacggat aacagttggt  10980
caagatgctc gggtaaccag agttggatgg tatttacgga agtacaaaat cgatgagctt  11040
cctcaattga tagatgttct ttctggaaca atgagtttgg ttggcccaag accggaagtg  11100
agggagttta ttgatgagta tcctgatgat ataagggaaa aagttttatc ggttaggcca  11160
gggataactg acttagcatc tatagaaatg gtagatgaaa atgagatttt gtctagttat  11220
gatgacccac gtagggctta tatagatata attcttccaa tcaagcaaag atattattta  11280
gattatgttg ctaacaattc agtaaagtat gattgtgtga taatttggaa aactattatt  11340
aagattttgt cgcgataata aggtagtgta ggatgattga tagaatattg gagctgccaa  11400
gaattgttaa gagaggtatc atcatctgca ttgatgtagt tatggtgata ttctcatttt  11460
ggttgtctta ttggttgagg cttgatgagc aaacggcttt tcttagtgca ccgatgtggt  11520
ttgctgcagc tattcttacc atatttaccg tgtttatatt tatcaggatt gggctttatc  11580
gggcagtctt acggtatgtt agtgcaaaga taatgttgct aataccagtt ggtattctgg  11640
cctcaacgtt atctcttgtc gttatatcat attcgctatc cataatgttg ccgcgcactg  11700
ttgtcggaat ttattttttg gtttttactt tactgacatc aggctctaga ttgcttttta  11760
gaatgatact taactatgga gttaagggta gtgcgcctgt tttgatttat ggcgctggtg  11820
aatctggccg acaattattg ccagcattaa tgcaggcaaa agaatatttt cctgtggcat  11880
ttgtggatga taatcctcgc ttgcataagg ctgtcattca tggtgtaaca gtttatccct  11940
cggataaact gagttacctt gtagatcgct atggtataaa gaaaattctt ttggcgatgc  12000
cgagcgtcag taagtcacaa aggcagaaag tgattactcg tttagagcat ctaccgtgtg  12060
aagttctctc tattccgggt atggtcgatt tagtcgaagg tcgagcacaa atcagtaatc  12120
taaaaaaagt atcgattgat gacttactag gtcgtgatcc ggttgctcct gatgccaaat  12180
tgatggccga aaacattact ggcaaagccg ttatggtcac tggggcggga ggctcgatcg  12240
gctctgagct ttgtcgtcaa attgttcgat ataagccggc caaattggtt ctatttgaac  12300
tgtctgaata tgccctctac gctattgaga aagagctctc ggcgctgtgt gacaaagaag  12360
ttttgaatgt tccagtgatc cctctgttgg gctcggtgca gcgtcagaat cgcttacaga  12420
tggtgatgaa gtcctttggt attcaaacgg tttatcatgc ggccgcttat aaacatgtgc  12480
ctctggttga gcataatgtg gtggaagggg tacgtaataa cgtgtttggt accttgtact  12540
gcgctgagtc agcgatcgaa agtggcgttg aaacttttgt gttgatttcc accgataaag  12600
cggtgcgccc gaccaacact atggggacaa ctaagcgtct ggccgaattg gtattgcagg  12660
ctttgtctgc acggcaaagc caaactcgct tttgtatggt gcgatttggt aatgtactcg  12720
gttcttcggg ctctgtcgtg ccgttgtttg aaaaacagat tgcccaaggt gggccagtta  12780
ccttgactca tcgtgacatt attcgctatt tcatgacaat tccggaagca tcacagttgg  12840
tgattcaagc gggggcgatg gggcatggcg gcgatgtctt tgtcttagac atgggcgatc  12900
cggtcaagat ttatgactta gccaaacgca tgatccggtt aagtggcttg agtgtacggg  12960
```

```
atgataaaaa tccagatggc gatattgcca ttgaagttac gggattacgt ccaggtgaga  13020

aactgtatga agaattactg attggtgatt cagttcaagg tacctctcat ccacgaatta  13080

tgacggccaa cgaagtgatg ctaccgtggc aggatctatc gctcttactt aaagagctgg  13140

atcaagcttg tcatgacttt gatcatgagc gaattcgcag tttgttgtta caagcaccag  13200

cggcattcaa tccaactgat gatatttgcg atctagtttg gcagcagaaa aaatcgctgt  13260

tatcacaagc gagcaatgtc attcgcctgt gattgcttag gtttaacctt ccacaccaat  13320

tcttcacctc tcttacaaat ccccgctagg cggtacatcg tgaccgcctt taccctgatg  13380

cctgctcttt aacaaacagg acatcagtgt atgtttaaac cttttagcgc cgaatttttc  13440

ggcactttct ggctggttct gggtggctgt ggtagcgcct tgatctctgc tgctttccca  13500

cagttaggta taggcttttt gggcgtggcg ttggcgtttg gtctgacagt agtcaccatg  13560

gcttatgcgg tcgggcacat ctctggtgcg cattttaacc ccgcggtgac cttgggtctg  13620

tgggccggtg gacgctttcc tgcagcgcgc gtgttacctt                        13660
```

<210> SEQ ID NO 17
<211> LENGTH: 12540
<212> TYPE: DNA
<213> ORGANISM: Plesiomonas shigelloides
<220> FEATURE:
<221> NAME/KEY: misc_feature
<223> OTHER INFORMATION: GenBank Accession No. AF285970, Plesiomonas shigelloides related sequences, Plesiomonas shigelloides O antigen gene cluster, complete sequence

<400> SEQUENCE: 17

```
attcttaaca cattgataag taatgggttt atttaatgtc aaaagcatct gaaccacaac    60

agactcctta tctgatccca caaggggctt atcccgtcta tatgccaaaa gcagaggatg   120

aaatcgatct tttcgagctt ttaagcacct tgtggaagaa aaagtgggtg attttatttg   180

tcacattgct gactacagga ttagcggcag tgtatgcctt taccgcaaaa gagcagtgga   240

cagcaaaaac ttatattcag gcaccacgta ttgctgaact agggagttat cttaaatttc   300

gtcaagcgta tgcccgaatt ttaaatcaac cgttagatac gagtgctttg gctaatgggt   360

tgttttctga tttgattttg attgctgaat caccagacac caaatttaaa tttttagagc   420

gaactgagta ttataaaaag gaaacacaga gtttatcctc tgagcaagat aagaaaattt   480

ggttagctga gcaagcgaaa aaaggccttg tgattacgcc accaaaggaa aaagaaaata   540

taagttacta cacaatacaa gcatcggcag attcagcgca agaggcatat aaactactac   600

aggggtatct aaaggatgtt aataatcaag ctgtaacatt aagtcttgat gagtttgatc   660

aaaacatcaa cactctttta gttagtttaa agaaagaagt taatgatatc gatttccaga   720

aaaaagcaga aaaactggat cagatagcat atattcagcg agatttaact acagcagagc   780

aagcgggtat tactgattat cgttctagta aaaatggctt tgataatgcg caaagtagct   840

ataagttctt gctcggtgaa aaactgttgt cagcagagct gaaagcaact aaagacgctc   900

ctattattta tccttttaga tattatgaag tgaagcgtca aattgatgag ttagaaggga   960

tgttacgcga taatattcag gcacaagcat atcgatatca aatgaagcca tctgagccag  1020

ttataaaaga caaacccaac aaagcattaa ttttgattct tggtgcatta ctaggggcaa  1080

tgtttgctat agttggtaca ttagtttatg cgacattaaa agataaaacc aagttagatt  1140

aaactgggtt acgtattgtt gtgtcaatgc gaaatagatg ttctatgtgc actttataat  1200

ggataagaaa atgaaattcg atactttgaa tgcgaaaatt gggattatag gccttggtta  1260
```

```
tgttggattg cctcttgctg ttgagtttgg aaagaaagta acgacgattg gatttgatat   1320
taataagtct cgtattgatg aattgcgaaa tggtcacgat agtacattag agtgctcaaa   1380
tttagagttg ttagaagcaa ctaaattgac gtacgcctgt tcattagatg cactaaaaga   1440
gtgtaatgta tttattgtaa ctgttccaac tccaattgat aaacataaac agccagatct   1500
aacacctcta attaaagcat ctgaaacatt gggtaagata ataaagaaag gcgatgttat   1560
tatttatgag tcaacagttt accctggagc gacagaagaa gattgtatac cagttgtaga   1620
gaaagtatca ggtcttaagt ttaatattga ttttttgcc ggttattcac ctgagcgtat    1680
taatcctggg gataaagagc atcgtgtaac taatatcctt aaggtgacca gtggatctac   1740
accggatgtt gctgagtatg tagatcagct atataaatta ataattactg tcggtacgca   1800
taaagcatca tcgataaaag tagcagaggc tgcaaaagta attgaaaaca cgcagcgaga   1860
tgtcaatatt gcattgatta atgagttatc tattatattt aataagttag ggattgatac   1920
cttagaggtt cttgaggctg caggtacgaa gtggaatttt ttacctttta ggcccggttt   1980
agtaggtggc cactgtatag gtgtagatcc ttattatctt acacataaag cgcaaagtgt   2040
cggctatcat ccagagatga ttttagccgg acgtcgttta aatgatagta tggggcagta   2100
tgtcgtttcc cagttagtca aaaaaatgtt gaaacaacgg attcaagttg aaggggcgaa   2160
tgtgttagtg atggggctta catttaaaga gaattgccca gatctacgaa acactaaagt   2220
gattgatatt atttcagagt taaaagaata caatatcaat atagatatta tagatccatg   2280
gtgttctacc gatgaggcac aacatgaata tggattaact ttatgtgaag atcctaaagt   2340
taatcattat gatgcaataa ttatcgctgt tgcacacaat gagtttcgcg agatgggaga   2400
gagcgctatt cgtgcattag gtaaagacga gcacgttttg ttcgatttaa aatatgtgct   2460
tgataaaaaa agtatcgata tgcgcttgta agagtgatta aaaaaatcaa atcctctttg   2520
atatgataca cctcagcatt ttatgctagg tttagcactt gattaatata catggatatt   2580
tatatgtctc gctatgaaga gattacacag cagttaattt tttcaccgaa aacttggtta   2640
attactggtg tcgctggctt tataggatca aatcttttag aaaagttact taaattaaac   2700
caggttgtta ttgggttaga taacttttcc acgggacatc aatataatct tgatgaagtt   2760
aaaacattag tttccactga acagtggagt cgattttgct ttatagaagg tgatattcga   2820
gatctcacta cctgtgagca agttatgaaa ggtgttgatc atgtcttaca tcaggctgcg   2880
ctaggttctg tacctcgttc aattgttgat cctataacaa ccaatgcaac taatattact   2940
ggatttttga atatcttaca tgcggctaaa aatgcacaag tacaaagttt tacttatgct   3000
gcatcaagct caacttatgg agatcatccc gcactaccaa aagtagagga aaacattggt   3060
aatccacttt ctccttatgc agttactaaa tatgttaacg agatttatgc tcaggtatat   3120
gctcgaacat atggttttaa aactattgga ttacgttatt ttaatgtatt tggtcgtcgt   3180
caagatccta atggagctta tgctgcagta attccaaaat ggacagcagc aatgcttaaa   3240
ggtgatgacg tatatattaa tggcgatggt gaaacgagtc gtgatttttg ttatatagat   3300
aatgttatac aaatgaatat attatctgca ttagcgaagg acagtgctaa agataatata   3360
tataatgttg cagttggtga tagaacaacg ttaaatgaat tatctggtta catttatgat   3420
gagcttaatt taattcacca tatcgataaa ttgagcatta agtatagaga gtttagatct   3480
ggagatgtta ggcattctca ggctgatgtt actaaggcta tagatttact aaagtataga   3540
ccaaatataa aaatcagaga gggattacga ctttcaatgc cgtggtatgt gagattttta   3600
```

```
aaaggctaaa ttatattaac atgaataaat aatctatttc acctctgtta ttaatgcagg   3660
ggtgaaaatc catgtgttta ttctaaatgg tcagtgtatg tttagaaaaa tgattgatgc   3720
aggtggtaca tttttactta aagcaatatt tcaaatagga gtttttgttt atttcgcaca   3780
tgtgtcagat attactacat ttggtattat tagctatgtg tttactgttt attggtttgt   3840
gcttaacttc tctgattatg gatttagaac aaaattagtg aaagatattt ctgataatag   3900
ttattctgca tcagaattat tatccagaag tgatggagtt aaaacatatg ttttttttctt   3960
catttttata atcttcatgt tttattctta tgtttctgat tcaatttcat taactctgct   4020
tgtttatatt tcatctgcat attttgtttg tatttcaagt ggtagattta gcttgctaca   4080
ggctgttggt cggtttagat gtgaattata tataaatatc tactcaacaa ttatatatat   4140
tgggtgtaat ttatttttat ctctgtttat cgaacctcta tattatagtg cgatatcaat   4200
attcatatac tcaatttcgc ttttggtttt ctcatcacat aaatgcaatg tgccatgttt   4260
tcatataaaa agaccaagtc ttttagttta taaagatttt ttggatgcaa ctccgttcgc   4320
tattctggtg ttactaaatg ttgttttatc tagtattgac ctttttatat taaaagaata   4380
tttctcttat aatagtgttg ctatatatca ggtggtaact agggttaata ccggtctaat   4440
gatagtgttt aatgttattt atactgtttt attgccttca ttttcttatt atctgaaaaa   4500
ttctgaatgg ggtaatataa ggaaattaca acgatatata tcactgttag tcttattact   4560
atgtttatgc tattattttt ttggcatcta tttcgtaggg atattgtttg gtgatgagta   4620
taaggtaata tcttctgcaa catttttgat aatgtttatg gctcttatta aatataattt   4680
ttggctaata aatgaacttt atcttgtgtg tagtggaaat caaagcgagc gagttaaatc   4740
gtattgtatt ggtgtggtca tttcaatagc ggtttttcttt tattttatac ctcggtatgg   4800
atggagtggg gcggtttttg gaagtgccat tgcaacatta gtaattggaa tattttatat   4860
tatttctgtg aaaaaagatt gtgggaaaat tcttcatgat aagtattcac taatgatgat   4920
ctttgtccca atttctttt attttattat taatggtcag tagcggttgt tatattaatc   4980
tgttgttgtt ttatatcgtt ccattaatat gtttagactc gattggaagt ctaataaagg   5040
ttaagtatgt taatatacct atatcctgta cttttgttat ttaatatcct tccggttttt   5100
ttttatggac aaatgaactc tgatttagag cgtttttttg gagttcctat tggctatatt   5160
tcagatctaa tattttattt ctttgttgct ttaacatcta taataacgtt gaggtttcac   5220
gtttctctgt ggacaaagaa attattattt ttaggcatca tattcctgat ttatatcagc   5280
attcagatgt tgttgttatc agcggatatc tcaggtgtcg taattttatt atcgtttttt   5340
tctaatttta tagctttggt tcttttggta tcattttgca ttggtaaaga tgagctttat   5400
ttaactcatt cggttagaaa tataaatgtt gtaatgtgtt ttggtattat ctgtggagtt   5460
gtaaaattat ttattggtta ttctgaagat agtaatttta tagtttattt aaatagaaat   5520
gccaccgcaa ttatagtagt gtgcttttat tgtgtatatt catactttta tcgtggtcga   5580
aagtcttggt atgtatcatc tgtattgtac tctctgttct ttctttttct agatagccga   5640
gcaggaataa tatcatttgc tatatcgttg tttttttgttt ttcttcagtt aacaaagaag   5700
gaaaagttat taatatcatt gttttttgtt cctcttctaa ctttaggtat ttcttttact   5760
gatataggca ctcgtcttga acgaatgctg tcttcgtcac aggttatatt ctctggtggt   5820
aacactctta caaaaagtca gaatgattat cgtcgagttg agttagtatt tattggggtt   5880
gatgttttaa aagaaaatta tttaattggc actggattag gtgttgcaaa ttatgtaaag   5940
gctatagata aaaagttttt aggaagtacc aactttgggt tggcgcataa tttttattta   6000
```

```
tcttattcgg ctcagttagg gattattggt tttattttgc ttatttctgt attttatata   6060

atgctgtctc caatttttaa atgcggaggg tatattggta aagggtgcgt ttttgctttg   6120

gctttctatg tcttttttaa tgagtatata ttgacgccag cgatatatat ttatatttct   6180

atttttttat cggtggtttt tatacgtaat tctaggatga gaatatgttg ttagaatatg   6240

ttgaaagaaa aatttcctta gccttgagta agtatcctaa ggtaagggat gttattaagt   6300

tcttttattt atatatcgca tcattattcg gaattatttt gaataaaaat aagacggtta   6360

ttcaatcaaa aatatacgag atttcaattg atgattctga agaatcattt tttggctatt   6420

atgaccatag tccaatgagc tctaatgggc ggtacgtatt gttccactct agtgcgttta   6480

gcactaaacg acacccaaag aaagttaagt atatatctat ttgcgtaaaa gaccttctta   6540

ataacaaagt ttataagcta tatgatacgc gagcatttaa ttggcagcag ggaagccgat   6600

taatgtggat tgatgatgac aatataattt ttaatgacta tgaaaataat ggatacatta   6660

gtgttgtcta ttctttgtct ttgatgaagg ttataaaaaa aataaactat ccgatttatg   6720

atgtgaataa ttacaaggct gtgacgttag atttctcatg gctggctaaa tatgatagcg   6780

attatggtta ttataataag aaatcatttt ctacagatat ttcaatcatt aatttgaaca   6840

cgggcggaat agaattattt ttatccttag acgaaatgct aaagagaact aattttaaat   6900

gtaatattga tgttgaacat gtggtcaatc attttatgtt tgctcccgat ggacgttccg   6960

ttatgttcat acatcgatac tatacaccta aaggaaagcg tgaaaggtta atacattgga   7020

atttaataaa tgataatgtt cgagtcctaa taaatgaatc gattattagt cattgttgtt   7080

ggaatgggaa tgatgaaatt ataggttttt ttggtgcaga aatagattcg cttaattatt   7140

atagattgtc aattgaatcc tgtaatacag agaaattgtt ttttgatgca agaaaatatt   7200

ctgatggaca tcctactata gttcataata gatatattat atctgatact tacccagata   7260

aaaatagaat taaaaagttg tttgtttatg accttgtcaa aaatgattat cgcgagcttg   7320

gattgtttta tgagtcaatg agtttttttt cttattctcg atgtgactta catccaagga   7380

tctcggttga taatagattt ttgtttgttg attcagttca ctcagggaaa agaaaactat   7440

attttatgag gagtggtatt tgtgagtgat gttctagtat ctttaattat agtttgcttt   7500

aatgcagaga agtatattga aaaatctctt ttggcattta ttaatcaaga tgttggatta   7560

gataaatttg aattgattat tgtagatggg gattcatctg ataatacaat atctattgtt   7620

caggatgttt tttctaaaca tagtaacatt aagcataaaa ttatcaataa taaaaaaaga   7680

actcttgcta cgggttggaa tattggggtg ctagaagcta atggtaagtt tgtgtgtaga   7740

gttgatgcac atagtgatat tccaaataac tatatatcta aattattaga tgattatttt   7800

aatattatgc agtttgatga tagcgttgtt ggtgttggag gtgtattaac taattcttat   7860

aaaactaagt ttggttcaat tgtagcggat ttttatgcat ctaaatttgg tgttggtaat   7920

tctccattta ggtgcgtaga caaaaataat cgactaaaaa aaacagatac ggctgtcttt   7980

gctttatata ataaagatgt gtttttttgat gttggacttt ttaatgaagt attagataga   8040

aatcaagata ttgattttca taagagagtt ttaagcaata atttttcatt atatacagat   8100

aatagtttat ttgttgagta ttatgttaga gataatttta aagatttcat aaagaaaggt   8160

tttcttgatg gtttttgggt tgttatgtct ggagcatatt attttagaca tatcgtgcca   8220

cttttttttg ttttgtattt aattgtatct ttttctcttt tctttgctac tggtgattat   8280

atatatttat ctttcttatt ttcttatttt cttatttcta ttttgttttc aattcgagat   8340
```

```
gggcgaagtt ttataggtaa agtatttctt ccttttatat ttttgtctta tcatatttct   8400
tatggatgtg gatcgttatt atcttttttg aaaaggtatt ttaaatgaaa aattttattc   8460
cttttgcgtt acctgaaatt ggcgaagaag aaattgcaga ggtaattgac tctttacgtt   8520
caggttggat tacgacaggt cctaaggcta agcaatttga acaagaattt tctaattacc   8580
taggagcgaa cgttcaatca ttagctgtta actctgctac gtcgggctta catttggctc   8640
ttgaagctgt tggcgtaaaa cctggagacc aagttattgt cccatcatat acattcactg   8700
ctactgccga aattgtcagg taccttggtg ctgatcctgt aattgttgat gtagatcgta   8760
aaacatttaa tatatcagtt gatgccattg agaaggctat tactaataaa acaaaggcga   8820
ttattccagt acacttcgct ggattagctt gtgacatgga ttcaatctta tcaattgcta   8880
aaaaatatga cctaaaggtt gtcgaggatg ccgctcatgc atttcctaca acatataaag   8940
gaagtaagat aggaacgctt gattcagatg ctacggtttt tagcttctac gccaataaaa   9000
ctatgacaac cggtgaaggc ggaatggttg tttcaaaaaa taaagatata attgagcgtt   9060
gtaaggtaat gcgtttacat ggaatcagtc gtgacgcttt tgaccggtac cagtctaaaa   9120
ctccttcttg gttttatgag gttgtagctc cagggtttaa atacaatatg cctgatatct   9180
gtgcggcaat cggtattcat caacttagaa agatcgatga ttttcagaaa aaacgtcaac   9240
gaatggcaaa aatttacgat gatgcgttaa aagaattgcc acttgaattg cctgaatggc   9300
ctactaatgc tagtgatatt catgcttggc atctatatcc tatccgctta aaaactgatt   9360
cggctattaa tcgcgatgat tttattaaga agttatcaga tcttggaatt ggttgttctg   9420
tccattttat accgttgcat aagcaaccgg tttggcgtga tacatataat ttgaacgcca   9480
gtgactttcc agtttctgag gagtgttatt taaatgaaat atctattcct ctttatacta   9540
aaatgacgga tcaagatcag ttgttcgtta tcgaatcgat tagacaatta tttatgtaat   9600
ggtattttat attaaatgaa acgtattttt gatgttatcg tggcaggctt aggcctgctt   9660
tttctatttc ctgtttttat cattgtgtca atgttaattg ttgctgattc taaagggagt   9720
gtttttttta ggcagtatag agttgggaga tttgggaaag attttaggat acataaattt   9780
agaacgatgt ttatcgattc agaaaaaaaa ggacggataa cagttggtca agatgctcgg   9840
gtaaccagag ttggatggta tttacggaag tacaaaatcg atgagctgcc tcaattgata   9900
gatgttcttt ctggaacaat gagtttggtt ggcccaagac cggaagtgag ggagtttatt   9960
gatgagtatc ctgatgatat aagggaaaaa gttttatcgg ttaggccagg gataactgac  10020
ttagcatcta tagaaatggt agatgaaaat gagattttgt ctagttatga tgacccacgt  10080
agggcttata tagatataat tcttccaatc aagcaaagat attatttgga ttatgttgct  10140
aacaattcag taaagtatga ttgtgtgata atttggaaaa ctattattaa gatttttgtcg 10200
cgataataag gtagtgtagg atgattgata gaatattgga gctgccaaga attgttaaga  10260
gaggtatcat catctgcatt gatgtagtta tggtgatatt ctcattttgg ttgtcttatt  10320
ggttgaggct tgatgagcaa acggcttttc ttagtgcacc gatgtggttt gctgcagcta  10380
ttcttaccat atttaccgtg tttatattta tcaggattgg gctttatcgg gcagtcttac  10440
ggtatgttag tgcaaagata atgttgctaa tatcagttgg tattctggcc tcaacgttat  10500
ctcttgtcgt tatatcatat tcgctatcca taatgttgcc gcgcactgtt gtcggaattt  10560
attttttggt tttactttta ctgacatcag gctctagatt gctttttaga atgatactta  10620
actatggagt taagggtagt gcgcctgttt tgatttatgg cgctggtgaa tctggccgac  10680
aattattgcc agcattaatg caggcaaaag aatattttcc tgtggcattt gtggatgata  10740
```

```
atcctcgctt gcataaggcc gtcattcatg gtgtaacagt ttatccctcg gataaactga  10800

gttacctagt agatcgctat ggtataaaga aaattctttt ggcgatgccg agcgtcagta  10860

agtcacaaag gcagaaagtg attactcgtt tagagcattt accgtgtgaa gttctctcta  10920

ttccgggcat ggtcgattta gtcgaaggtc gagcacaaat cagtaatctc aaaaaagtat  10980

cgattgatga cttgctaggc cgtgatccag ttgctcctga tgccaaattg atggcggaga  11040

acattacagg caaagcagtt atggtcactg gggcgggagg atcgatcggc tctgagcttt  11100

gtcgtcaaat tgttcgatat aagccagcca aattggttct atttgaactg tctgaatatg  11160

ccctgtatgc cattgagaaa gagctatcga cgctgtgtga taaagaaggt ttggatgtct  11220

cagtgatccc tctgttgggc tcggtgcagc gtcagaatcg cttacagatg gtgatgaagt  11280

cctttggtat tcaaacggtt tatcatgcgg ctgcttataa acatgtgcct ctggttgagc  11340

ataatgtggt ggaaggggtg cgtaataatg tgtttggtac cttgtactgc gctgagtcgg  11400

cgatcgatag tggcgttgaa acctttgtgt tgatttccac cgataaagcg gtgcggccga  11460

ccaacactat ggggacaacc aagcgcctgg ctgagttggt attgcaggcg ttgtctgcac  11520

ggcaaagcaa aacccgtttt tgtatggtgc gatttggtaa tgtgctggga tcctcgggct  11580

cagttgtacc attgtttgaa aagcagattg cccaaggtgg gccagttacc ctgactcatc  11640

gtgacattat tcgctatttt atgacaattc ctgaagcatc gcagttggtg attcaagcgg  11700

gggcgatggg gcatggcggc gatgtctttg tcttagacat gggcgatccg gttaagattt  11760

atgacttagc caaacgcatg atccggttaa gtggcttgac tgtgcgggat gataaaaatc  11820

cagatggcga tattgccatt gaagttacgg gattacgtcc aggtgagaaa ctgtatgaag  11880

aattactgat tggtgattca gttcaaggta cctctcatcc acgaattatg acggccaacg  11940

aagtgatgct accgtggcag gatctatcgc tcttacttaa agagctggat caagcctgtc  12000

atgactttga tcatgagcgc attcgcagct tattgttaca agcaccagcg gcattcaatc  12060

caactgatga tatttgcgat ctagtttggc agcagaaaaa atcgctgtta tcacaagcga  12120

gcaatgtcat acgcctgtga ttgtttagat ttaaccttcc acaccaattc ttcacctctc  12180

ttacaaatcc ccgctaggcg gttcatcgtg accgccttta ccctgatgtc agctctttaa  12240

caaacaggac atcagtgtat gtttaaacct tttagcgccg aatttttcgg tactttctgg  12300

ctggttctgg gtggctgtgg tagcgccttg atctctgctg ctttccctca gttaggtatt  12360

ggctttttgg gcgtggcgtt ggcttttggt ctgacagtag tcaccatggc ttatgcggtc  12420

gggcatatct ccggagcgca ttttaacccc gcggtgacct tgggtctgtg ggccggtgga  12480

cgcttccctg cggcgcgcgt gttaccttac atcatcgctc aggttatcgg cggtattgcc  12540
```

<210> SEQ ID NO 18
<211> LENGTH: 14991
<212> TYPE: DNA
<213> ORGANISM: Plesiomonas shigelloides
<220> FEATURE:
<221> NAME/KEY: misc_feature
<223> OTHER INFORMATION: GenBank Accesion No. AB025970, Plesiomonas shigelloides related sequences, Plesiomonas shigelloides gene for ORF1P, ORF2P, ORF3P, ORF4P, ORF5P, ORF6P, ORF7P, ORF8P, ORF9P, ORF10P, and ORF11P

<400> SEQUENCE: 18

```
aagcttgatc aaatagctca tattcagcga gatttaacaa ctgcggaaca agccggaatc     60

attgattatc gctctagcaa aggcggcttc gataatgcgc aaagtagcta taagttcttg    120
```

-continued ctcggcgaaa aactgttatc agcagagcta aaagcaacta aagatgcgcc aattatttac 180
ccatttagat attacgaagt gaaacgtcaa attgatgagt tagaaggaat gttacgcgat 240
aacattcagg cgcaagcata tcgatatcaa atgaagccat ctgagccagt tataaaagac 300
aaacccaaca aagcattaat tttgattctt ggtgcattac taggggcaat gtttgctata 360
gttggtacat tagtttatgc gacattaaaa gataaaacca agttagatta aactgggtta 420
cgtattgttg tgtcaatgcg aaatagatgt tctatgtgca ctttataatg gataagaaaa 480
tgaaattcga tactttgaat gcgaaaattg ggattatagg ccttggttat gttggattgc 540
ctcttgctgt tgagtttgga aagaaagtaa cgacgattgg atttgatatt aataagtctc 600
gtattgatga attgcgaaat ggtcacgata gtacattaga gtgctcaaat ttagagttgt 660
tagaagcaac taaattgacg tacgcctgtt cattagatgc actaaaagag tgtaatgtat 720
ttattgtaac tgttccaact ccaattgata aacataaaca gccagatcta acacctctaa 780
ttaaagcatc tgaaacattg ggtaagataa taaagaaagg cgatgttatt atttatgagt 840
caacagttta ccctggagcg acagaagaag attgtatacc agttgtagag aaagtatcag 900
gtcttaagtt taatattgat ttttttgccg gttattcacc tgagcgtatt aatcctgggg 960
ataaagagca tcgtgtaact aatatcctta aggtgaccag tggatctaca ccggatgttg 1020
ctgagtatgt agatcagcta tataaattaa taattactgt cggtacgcat aaagcatcat 1080
cgataaaagt agcagaggct gcaaaagtaa ttgaaaacac gcagcgagat gtcaatattg 1140
cattgattaa tgagttatct attatattta ataagttagg gattgatacc ttagaggttc 1200
ttgaggctgc aggtacgaag tggaattttt tacctttag gcccggttta gtaggtggcc 1260
actgtatagg tgtagatcct tattatctta cacataaagc gcaaagtgtc ggctatcatc 1320
cagagatgat tttagccgga cgtcgtttaa atgatagtat ggggcagtat gtcgtttccc 1380
agttagtcaa aaaaatgttg aaacaacgga ttcaagttga aggggcgaat gtgttagtga 1440
tggggcttac atttaaagag aattgcccag atctacgaaa cactaaagtg attgatatta 1500
tttcagagtt aaaagaatac aatatcaata tagatattat agatccatgg tgttctaccg 1560
atgaggcaca acatgaatat ggattaactt tatgtgaaga tcctaaagtt aatcattatg 1620
atgcaataat tatcgctgtt gcacacaatg agtttcgcga gatgggagag agcgctattc 1680
gtgcattagg taaagacgag cacgttttgt tcgatttaaa atatgtgctt gataaaaaaa 1740
gtatcgatat gcgcttgtaa gagtgattaa aaaaatcaaa tcctctttga tatgatacac 1800
ctcagcattt tatgctaggt ttagcacttg attaatatac atggatattt atatgtctcg 1860
ctatgaagag attacacagc agttaatttt ttcaccgaaa acttggttaa ttactggtgt 1920
cgctggcttt ataggatcaa atcttttaga aaagttactt aaattaaacc aggttgttat 1980
tgggttagat aacttttcca cgggacatca atataatctt gatgaagtta aaacattagt 2040
ttccactgaa cagtggagtc gattttgctt tatagaaggt gatattcgag atctcactac 2100
ctgtgagcaa gttatgaaag gtgttgatca tgtcttacat caggctgcgc taggttctgt 2160
acctcgttca attgttgatc ctataacaac caatgcaact aatattactg gatttttgaa 2220
tatcttacat gcggctaaaa atgcacaagt acaaagtttt acttatgctg catcaagctc 2280
aacttatgga gatcatcccg cactaccaaa agtagaggaa aacattggta atccactttc 2340
tccttatgca gttactaaat atgttaacga gatttatgct caggtatatg ctcgaacata 2400
tggttttaaa actattggat tacgttattt taatgtattt ggtcgtcgtc aagatcctaa 2460
tggagcttat gctgcagtaa ttccaaaatg gacagcagca atgcttaaag gtgatgacgt 2520

```
atatattaat ggcgatggtg aaacgagtcg tgatttttgt tatatagata atgttataca   2580
aatgaatata ttatctgcat tagcgaagga cagtgctaaa gataatatat ataatgttgc   2640
agttggtgat agaacaacat taaatgaatt atctggttac atttatgatg agcttaattt   2700
aattcaccat atcgataaat tgagcattaa gtatagagag tttagatctg gagatgttag   2760
gcattctcag gctgatgtta ctaaggctat agatttacta cagtatagac caaatataaa   2820
aatcagagag ggattacgac tttcaatgcc gtggtatgtg agatttttaa aaggctaaat   2880
tatattaaca tgaataaata atctatttca cctctgttat taatgcaggg gtgaaaatct   2940
atgtgtttat tctaaatggt cagtgtatgt ttagaaaaat gattgatgca ggtggtacat   3000
ttttacttaa agcaatattt caaataggag tttttgttta tttcgcacat gtgtcagata   3060
ttactacatt tggtattatt agttatgtgt ttactgttta ttggtttgtg cttaacttct   3120
ctgattatgg atttagaaca aaattagtga aagatatttc tgataatagt tattctgcat   3180
cagaattatt atccagaagt gatggagtta aaacatatgt ttttttcttc atttttataa   3240
tcttcatgtt ttattcttat gtttctgatt caatttcatt aactctgctt gtttatattt   3300
catctgcata ttttgtttgt atttcaagtg gtagatttag cttgctacag gctgttggtc   3360
ggtttagatg tgaattatat ataaatatct actcaacaat tatatatatt gggtgtaatt   3420
tatttttatc tctgtttatc gaacctctat attatagtgc gatatcaata ttcatatact   3480
caatttcgct tttggttttc tcatcacata aatgcaatgt gccatgtttt catataaaaa   3540
gaccaagtct tttagtttat aaagattttt tggatgcaac tccgttcgct attctggtgt   3600
tactaaatgt tgttttatct agtattgacc tttttatatt aaaagaatat ttctcttata   3660
atagtgttgc tatatatcag gtggtaacta gggttaatac cggtctaatg atagtgttta   3720
atgttattta tactgtttta ttgccttcat tttcttatta tctgaaaaat tctgaatggg   3780
gtaatataag gaaattacaa cgatatatat cactgttagt cttattacta tgtttatgct   3840
attatttttt tggcatctat ttcgtaggga tattgtttgg tgatgagtat aaggtaatat   3900
cttctgcaac atttttgata atgtttatgg ctcttattaa atataatttt tggctaataa   3960
atgaacttta tcttgtgtgt agtggaaatc aaagcgagcg agttaaatcg tattgtattg   4020
gtgtggtcat ttcaatagcg gttttctttt attttatacc tcggtatgga tggagtgggg   4080
cggtttttgg aagtgccatt gcaacattag taattggaat attttatatt atttctgtga   4140
aaaaagattg tgggaaaatt cttcatgata agtattcact aatgatgatc tttgtcccaa   4200
ttttctttta ttttattatt aatggtcagt agcggttgtt atattaatct gttgttgttt   4260
tatatcgttc cattaatatg tttagactcg attggaagtc taataaaggt taagtatgtt   4320
aatataccta tatcctgtac ttttgttatt taatatcctt ccggtttttt tttatggaca   4380
aatgaactct gatttagagc gttttttttgg agttcctatt ggctatattt cagatttaat   4440
attttatttc tttgttgctt taacatctat aataacgttg aggtttcacg tttctctgtg   4500
gacaaagaaa ttattatttt taggcatcat attcctgatt tatatcagca ttcagatgtt   4560
gttgttatca gcggatatct caggtgtcgt aattttatta tcgttttttt ctaattttat   4620
agctttggtt cttttggtat cattttgcat tggtaaagat gagctttatt taactcattc   4680
ggttagaaat ataaatgttg taatgtgttt tggtattatc tgtggagttg taaaattatt   4740
tattggttat tctgaagata gtaattttat agtttattta aatagaaatg ccaccgcaat   4800
tatagtagtg tgcttttatt gtgtatattc atacttttat cgtggtcgaa agtcttggta   4860
```

```
tgtctcatct gtattgtact ctctgttctt tctttttcta gatagccgag caggaataat   4920
atcatttgct atatcgttgt tttttgtttt tcttcagtta acaaagaagg aaaagttatt   4980
aatatcattg ttttttgttc ctcttctaac tttaggtatt tcttttactg atataggcac   5040
tcgtcttgaa cgaatgctgt cttcgtcaca ggttatattc tctggtggta acactcttac   5100
aaaaagtcag aatgattatc gtcgagttga gttagtattt attggggttg atgttttaaa   5160
agaaaattat ttaattggca ctggattagg tgttgcaaat tatgtaaagg ctatagataa   5220
aaagttttta ggaagtacca actttgggtt ggcgcataat ttttatttat cttattcggc   5280
tcagttaggg attattggtt ttattttgct tatttctgta ttttatataa tgctgtctcc   5340
aatttttaaa tgcggagggt atattggtaa agggtgcgtt tttgctttgg ctttctatgt   5400
ctttttaat gagtatatat tgacgccagc gatatatatt tatatttcta tttttttatc    5460
ggtggttttt atacgtaatt ctaggatgag aatatgttgt tagaatatgt tgaaagaaaa   5520
atttccttag ccttgagtaa gtatcctaag gtaagggatg ttattaagtt cttttattta   5580
tatatcgcat cattattcgg aattattttg aataaaaata agacggttat tcaatcaaaa   5640
atatacgaga tttcaattga tgattctgaa gaatcatttt ttggctatta tgaccatagt   5700
ccaatgagct ctaatgggcg gtacgtattg ttccactcta gtgcgtttag cactaaacga   5760
cacccaaaga aagttaagta tatatctatt tgcgtaaaag accttcttaa taacaaagtt   5820
tataagctat atgatacgcg agcatttaat tggcagcagg gaagccgatt aatgtggatt   5880
gatgatgaca atataatttt taatgactat gaaaataatg gatacattag tgttgtctat   5940
tctttgtctt tgatgaaggt tataaaaaaa ataaactatc cgatttatga tgtgaataat   6000
tacaaggctg tgacgttaga tttctcatgg ctggctaaat atgatagcga ttatggttat   6060
tataataaaa aatcattttc tacagatatt tcaatcatta atttgaacac gggcggaata   6120
gaattatttt tatccttaga cgaaatgcta aagagaacta attttaaatg taatattgat   6180
gttgaacatg tggtcaatca ttttatgttt gctcccgatg gacgttccgt tatgttcata   6240
catcgatact atacacctaa aggaaagcgt gaaaggttaa tacattggaa tttaataaat   6300
gataatgttc gagtcctaat aaatgaatcg attattagtc attgttgttg gaatgggaat   6360
gatgaaatta taggtttttt tggtgcagaa atagattcgc ttaattatta tagattgtca   6420
attgaatcct gtaatacaga gaaattgttt tttgatgcaa gaaaatattc tgatggacat   6480
cctactatag ttcataatag atatattata tctgatactt acccagataa aaatagaatt   6540
aaaaagttgt ttgtttatga ccttgtcaaa aatgattatc gcgagcttgg attgttttat   6600
gagtcaatga gtttttttc ttattctcga tgtgacttac atccaaggat ctcggttgat    6660
aatagatttt tgtttgttga ttcagttcac tcagggaaaa gaaaactata ttttatgagg   6720
agtggtattt gtgagtgatg ttctagtatc tttaattata gtttgcttta atgcagagaa   6780
gtatattgaa aaatctcttt tggcatttat taatcaagat gttggattag ataaatttga   6840
attgattatt gtagatgggg attcatctga taatacaata tctattgttc agaatgtttt   6900
ttctaaacat agtaacatta agcataaaat tatcaataat aaaaaaagaa ctcttgctac   6960
gggttggaat attggggtgc tagaagctaa tggtaagttt gtgtgtagag ttgatgcaca   7020
tagtgatatt ccaaataact atatatctaa attattagat gattatttta atattatgca   7080
gtttgatgat agcgttgttg gtgttggagg tgtattaact aattcttata aaactaagtt   7140
tggttcaatt gtagcggatt tttatgcatc gaaatttggt gttggtaatt ctccatttag   7200
gtgcgtagac aaaaataatc gactaaaaaa aacagatacg gctgtctttg ctttatataa   7260
```

```
taaagatgtg tttttgatg ttggactttt taatgaagta ttagatagaa atcaagatat   7320
tgattttcat aagagagttt taagcaataa tttgtcatta tatacagata atagtttatt   7380
tgttgagtat tatgttagag ataattttaa agatttcata aagaaaggtt ttcttgatgg   7440
tttttgggtt gttatgtctg gagcatatta ttttagacat atcgtgccac ttttttttgt   7500
tttgtattta attgtatctt tttctctttt ctttgctact ggtgattata tatatttatc   7560
tttcttattt tcttatttc ttatttctat tttgttttca attcgagatg ggcgaagttt   7620
tataggtaaa gtatttcttc cttttatatt tttgtcttat catatttctt atggatgtgg   7680
atcgttatta tctttttga aaaggtattt taaatgaaaa atttttattcc ttttgcgtta   7740
cctgaaattg gcgaagaaga aattgcagag gtaattgact ctttacgttc aggttggatt   7800
acgacaggtc ctaaggctaa gcaatttgaa caagaatttt ctaattacct aggagcgaac   7860
gttcaatcat tagctgttaa ctctgctacg tcgggcttac atttggctct tgaagctgtt   7920
ggcgtaaaac ctggagacca agttattgtc ccatcatata cattcactgc tactgccgaa   7980
attgtcaggt accttggtgc tgatcctgta attgttgatg tagatcgtaa aacatttaat   8040
atatcagttg atgccattga gaaggctatt actaataaaa caaaggcgat tattccagta   8100
cacttcgctg gattagcttg tgacatggat tcaatcttat caattgctaa aaaatatgac   8160
ctaaaggttg tcgaggatgc cgctcatgca tttcctacaa catataaagg aagtaagata   8220
ggaacgcttg attcagatgc tacggttttt agcttctacg ccaataaaac tatgacaacc   8280
ggtgaaggcg gaatggttgt ttcaaaaaat aaagatataa ttgagcgttg taaggtaatg   8340
cgtttacatg gaatcagtcg tgacgctttt gaccggtacc agtctaaaac tccttcttgg   8400
ttttatgagg ttgtagctcc agggtttaaa tacaatatgc ctgatatctg tgcggcaatc   8460
ggtattcatc aacttagaaa gatcgatgat tttcagaaaa aacgtcaacg aatggcaaaa   8520
atttacgatg atgcgttaaa agaattgcca cttgaattgc ctgaatggcc tactaatgct   8580
agtgatattc atgcttggca tctatatcct atccgcttaa aaactgattc ggctattaat   8640
cgcgatgatt ttattaagaa gttatcagat cttggaattg gttgttctgt ccattttata   8700
ccgttgcata agcaaccggt ttggcgtgat acatataatt tgaacgccag tgactttcca   8760
gtttctgagg cgtgttattt aaatgaaata tctattcctc tttatactaa aatgacggat   8820
caagatcagt tgttcgttat cgaatcgatt agacaattat ttatgtaatg gtattttata   8880
ttaaatgaaa cgtatttttg atgttatcgt ggcaggctta ggcctgcttt ttctatttcc   8940
tgtttttatc attgtgtcaa tgttaattgt tgctgattct aaagggagtg ttttttttag   9000
gcagtataga gttgggagat ttgggaaaga ttttaggata cataaattta gaacgatgtt   9060
tatcgattca gaaaaaaaag gacggataac agttggtcaa gatgctcggg taaccagagt   9120
tggatggtat ttacggaagt acaaaatcga tgagctgcct caattgatag atgttctttc   9180
tggaacaatg agtttggttg gcccaagacc ggaagtgagg gagtttattg atgagtatcc   9240
tgatgatata agggaaaaag ttttatcggt taggccaggg ataactgact tagcatctat   9300
agaaatggta gatgaaaatg agattttgtc tagttatgat gacccacgta gggcttatat   9360
agatataatt cttccaatca agcaaagata ttatttggat tatgttgcta acaattcagt   9420
aaagtatgat tgtgtgataa tttggaaaac tcttattaag attttgtcgc gataataagg   9480
tagtgtagga tgattgatag aatattggag ctgccaagaa ttgttaagag aggtatcatc   9540
atctgcattg atgtagttat ggtgatattc tcattttggt tgtcttattg gttgaggctt   9600
```

```
gatgagcaaa cggcttttct tagtgcaccg atgtggtttg ctgcagctat tcttaccata   9660
tttaccgtgt ttatatttat caggattggg ctttatcggg cagtcttacg gtatgttagt   9720
gcaaagataa tgttgctaat atcagttggt attctggcct caacgttatc tcttgtcgtt   9780
atatcatatt cgctatccat aatgttgccg cgcactgttg tcggaattta tttttggtt   9840
ttacttttac tgacatcagg ctctagattg ctttttagaa tgatacttaa ctatggagtt   9900
aagggtagtg cgcctgtttt gatttatggc gctggtgaat ctggccgaca attattgcca   9960
gcattaatgc aggcaaaaga atattttcct gtggcatttg tggatgataa tcctcgcttg  10020
cataaggccg tcattcatgg tgtaacagtt tatccctcgg ataaactgag ttacctagta  10080
gatcgctatg gtataaagaa aattcttttg gcgatgccga gcgtcagtaa gtcacaaagg  10140
cagaaagtga ttactcgttt agagcattta ccgtgtgaag ttctctctat tccgggcatg  10200
gtcgatttag tcgaaggtcg agcacaaatc agtaatctca aaaaagtatc gattgatgac  10260
ttgctaggcc gtgatccagt tgctcctgat gccaaattga tggcggagaa cattacaggc  10320
aaagcagtta tggtcactgg ggcgggagga tcgatcggct ctgagctttg tcgtcaaatt  10380
gttcgatata agccagccaa attggttcta tttgaactgt ctgaatatgc cctgtatgcc  10440
attgagaaag agctatcgac gctgtgtgat aaagaaggtt tggatgtctc agtgatccct  10500
ctgttgggct cggtgcagcg tcagaatcgc ttacagatgg tgatgaagtc ctttggtatt  10560
caaacggttt atcatgcggc tgcttataaa catgtgcctc tggttgagca taatgtggtg  10620
gaaggggtgc gtaataatgt gtttggtacc ttgtactgcg ctgagtcggc gatcgatagt  10680
ggcgttgaaa cctttgtgtt gatttccacc gataaagcgg tgcggccgac caacactatg  10740
gggacaacca agcgcctggc tgagttggta ttgcaggcgt tgtctgcacg gcaaagcaaa  10800
acccgttttt gtatggtgcg atttggtaat gtgctgggat cctcgggctc agttgtacca  10860
ttgtttgaaa agcagattgc ccaaggtggg ccagttaccc tgactcatcg tgacattatt  10920
cgctatttta tgacaattcc tgaagcatcg cagttggtga ttcaagcggg ggcgatgggg  10980
catggcggcg atgtctttgt cttagacatg ggcgatccgg ttaagattta tgacttagcc  11040
aaacgcatga tccggttaag tggcttgact gtgcgggatg ataaaaaatcc agatggcgat  11100
attgccattg aagttacggg attacgtcca ggtgagaaac tgtatgaaga attactgatt  11160
ggtgattcag ttcaaggtac ctctcatcca cgaattatga cggccaacga agtgatgcta  11220
ccgtggcagg atctatcgct cttacttaaa gagctggatc aagcctgtca tgactttgat  11280
catgagcgca ttcgcagctt attgttacaa gcaccagcgg cattcaatcc aactgatgat  11340
atttgcgatc tagtttggca gcagaaaaaa tcgctgttat cacaagcgag caatgtcata  11400
cgcctgtgat tgtttagatt taaccttcca caccaattct tcacctctct tacaaatccc  11460
cgctaggcgg ttcatcgtga ccgcctttac cctgatgtca gctctttaac aaacaggaca  11520
tcagtgtatg tttaaacctt ttagcgccga atttttcggt actttctggc tggttctggg  11580
tggctgtggt agcgccttga tctctgctgc tttccctcag ttaggtattg gctttttggg  11640
cgtggcgttg gcttttggtc tgacagtagt caccatggct tatgcggtcg ggcatatctc  11700
cggagcgcat tttaaccccg cggtgacctt gggtctgtgg gccggtggac gcttccctgc  11760
ggcgcgcgtg ttaccttaca tcatcgctca ggttatcggc ggtattgccg ctgcggcagt  11820
gctgtatggt atcgccagcg gtaaggcggg gtttgatgcg acaaccagcg gctttgcagc  11880
taatggctat ggcattcact caccaggcgg ttatgcgtta agcgcctgta tgctgagcga  11940
gtttgtcctc agtgcgtttt ttgtcatcgt gatccacggg gcgacagaaa aacgcgctcc  12000
```

```
tgcgggcttt gcgccgttgg cgattggtct gacgctgacc atcattcatt tggtgagcat  12060
ccctgtcacc aatacctcgg ttaaccctgc gcgtagtatc gcggcggcag ttttccaagg  12120
tacttgggcg ttagatcagt tgtggatgtt ttgcttgatc ccatcattag gcggaattgc  12180
cggtggtctg atttaccgcg cattgctggc gcgtccggct gaagcataaa actgagacaa  12240
tcatttaaag aggaaaggtg ttggagtgat ccggcgcctt tctttttttt atggcttttt  12300
ttggggatag gtcaggggat attggtcaga tacagaatgg atgtgtcagt cggcaaccta  12360
ggcatcgaca caaaaaaagg cggcataaat gccgcctgaa ttggctacag aatatcgtat  12420
aaacgatgtc tgtgatcaca aagataaaat agcatcaaca aaaaaacggc aattcggtgt  12480
gtgttacgaa gccatgcaga cagcacttaa atgggcggta actgcatggc ttttttagct  12540
tatttgaacg ggtaagtaat ataaccgcgt tccatttttt cttgttttac atcgtaatcg  12600
cttggtacgt cattcgcagc gatgaagccg tagaagatgt aacccagcag agtcaggatt  12660
gagccgtaga acacggcagt ctgaccacaa gcgtacacac cgtagatact gtagatggca  12720
gcgaaagcac ccaccacggc accaatcttc cattggctag cactgacgtg gtttttacgc  12780
agcataacaa acagaccagt ttgagacagt acgtatggca ccatgttgat gaacactgac  12840
aggttcagca gggtattgaa ctgttgtacg gtgttcggag aaatactcat ggttgccagc  12900
agcaactcca gcaccagcat gatcagcata ccggcgatag gtgcgttgta tttgttcatt  12960
ttgccgaaga tgcttgggaa cagcttcatt tgcgctgccg cccaagatac ttgcgcgtta  13020
gtgaactgcc aagccagcag agaaccgata caggcgatga tggccagagc acaaatcact  13080
tggcccacaa acggtgtgaa catcatgctg aataccagac cgaacggcgc actggatttc  13140
gccagttcag cgttaggcac gataccctga attacggtag ttgacgcgat gtacacgata  13200
gccacggaaa cggtcgccag cataacggcc agtggtacgg tttttttctgg gttacgaacg  13260
gcgccggagt tagcacctgc agtttcaatc cccaagaagg cccacagagt cagagcgata  13320
ccggaagaga tcccgtccat agtgccaacg tggtgtgggt tccagccggc ggcgaacagt  13380
tcaggtttga accagaacca accgatgatg gacagaccca ccacaggaat gatgatcccc  13440
catacagtta cgctggaaat accaccggtg tatttaggac cccagaagtt agctaccatg  13500
gtcaacacca gaacgcccac gacaccccag aaagcgtgta ctgcagattc agataaccat  13560
gggaagaaag gtttcatgta gccaaccgca gatacggcaa tcgccaccgc actgatgacc  13620
aagcaaatat aataggtata agacgcgatg aagaaggagg acttaccgtg cgcttcttgt  13680
gagtaggcag acataccgcc atcacggtga cagaacatac cgcattttgc gtaagtgtaa  13740
gcgatacaca gcgcacccac ggtagtgacc agccaggaga gcatggtaat accacctgta  13800
ccggcgaggt tagccggcag catgataata ccggagccca tcatgtttac tgttaccagc  13860
acagtgaggc ccataagccc cattttgtta tcatctgaag atgccataaa atttatctct  13920
ttattcgata aacttaatat ttattcatcc aaagtcacta aaatatgcac aggatgtgca  13980
taactgagga tgaggaaccc ttatttgttg ctgcagcgaa aacccacacc aaggatgtta  14040
ataaatgaga taacggcgca ggaataatac cgttattgca tttatgtttt tgctgaaaat  14100
aaggccatta atgttgatgc gtgaataaac atttctggct cgatatacat cccgtatatg  14160
agttggttta ttttttaaca cagctgcata gggaagaaaa taaaggtcga gaaaatcgga  14220
ttgtgccttg tgtcgcgtaa ttatttatga atttatgaat aatcagtaat cctgacgaaa  14280
agtcgttatt gtatgtaatc atctttaagt gtaatttcac gcaaccagat gtttctttcc  14340
```

```
ttgcgccgcc agcgctttgt tttatgtgtt gaaataatct tttctgtaac cgcgcgtaat  14400

ttatcctttc ctctctttat tttgtgtatt tcgttgtaca taagtggtgt ttatttatgc  14460

atgtcattta ttgatggttt attgctgcgt actgaatgaa gtgtaacttg gtagaaaaag  14520

aaggctgaat gtttattgcc tcctgtttca ggttatgaca atgaatgctc tatttgtaca  14580

gttaacttta cgtcatttga taatgtcatt tactgtgcca gcgtaatttt attaatggcg  14640

tgctgtcggg caatttggtt ttcggcgcct taataaaata ttccgcgatc aatatcacaa  14700

atagcatttt cattaggaaa ttaaatatca attttctgcg gataggctgg gcgcactatt  14760

gagcgataaa acgctgtgaa aatagcgatt ggcagcattg cgttgcctgt atttatctcg  14820

tttgccggat ttttatgcat ttgagtgcgc agccgccgtg ccgcccatac atgctctatc  14880

ttttactgtg ggtctcaca tattccaccg ttattacatg tgatggctat tactcgttgt  14940

gctggcgtgt tggcgagcgg atgcagagcg tggcaagcag agccggtcga c          14991


<210> SEQ ID NO 19
<211> LENGTH: 27
<212> TYPE: DNA
<213> ORGANISM: Artificial Sequence
<220> FEATURE:
<223> OTHER INFORMATION: Description of artificial sequence: putative
      promoter, -35 and -10 consensus sequence of AF294823 (SEQ ID NO:7
      positions 1645-1671)
<220> FEATURE:
<221> NAME/KEY: modified_base
<222> LOCATION: (7)..(21)
<223> OTHER INFORMATION: n=g, a, c, or t
<220> FEATURE:
<221> NAME/KEY: misc_feature
<222> LOCATION: (7)..(21)
<223> OTHER INFORMATION: n is a, c, g, or t

<400> SEQUENCE: 19

attaccnnnn nnnnnnnnnn ntatagt                                        27


<210> SEQ ID NO 20
<211> LENGTH: 14
<212> TYPE: DNA
<213> ORGANISM: Artificial Sequence
<220> FEATURE:
<223> OTHER INFORMATION: Description of artificial sequence: region of
      pWR102 plasmid upstream of wbgT gene containing left inverted
      repeat (IRL) of IS91

<400> SEQUENCE: 20

cctactcgat cagc                                                      14


<210> SEQ ID NO 21
<211> LENGTH: 19
<212> TYPE: DNA
<213> ORGANISM: Artificial Sequence
<220> FEATURE:
<223> OTHER INFORMATION: Description of artificial sequence: region of
      pWR101 plasmid downstream of wbgZ gene containing right inverted
      repeat (IRR) and target sequence of IS91

<400> SEQUENCE: 21

ggttgcgttc atcgatagg                                                 19


<210> SEQ ID NO 22
<211> LENGTH: 14
<212> TYPE: DNA
<213> ORGANISM: Artificial Sequence
<220> FEATURE:
<223> OTHER INFORMATION: Description of artificial sequence: a portion
```

```
      of the pWR101 cosmid downstream from gene wbgZ containing IRL of
      IS91 and target sequence; region of pWR101 plasmid downstream of
      wbgZ gene containing left inverted repeat (IRL) of IS91

<400> SEQUENCE: 22

cctactcggg ggtt                                                     14
```